United States Patent
Sarkar et al.

(10) Patent No.: US 10,495,648 B2
(45) Date of Patent: Dec. 3, 2019

(54) METHODS OF TREATING LIVER FIBROSIS

(71) Applicant: GILEAD SCIENCES, INC., Foster City, CA (US)

(72) Inventors: Nandita Amartya Kumar Sarkar, Foster City, CA (US); Ren Y. Xu, Foster City, CA (US); Biao Li, Fremont, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 16/006,615

(22) Filed: Jun. 12, 2018

(65) Prior Publication Data

US 2019/0004066 A1  Jan. 3, 2019

Related U.S. Application Data

(60) Provisional application No. 62/518,696, filed on Jun. 13, 2017, provisional application No. 62/575,830, filed on Oct. 23, 2017.

(51) Int. Cl.

| | |
|---|---|
| *A61K 48/00* | (2006.01) |
| *C07H 21/04* | (2006.01) |
| *C07H 21/02* | (2006.01) |
| *G01N 33/68* | (2006.01) |
| *C12Q 1/6883* | (2018.01) |
| *C12Q 1/6809* | (2018.01) |

(52) U.S. Cl.
CPC ....... *G01N 33/6893* (2013.01); *C12Q 1/6809* (2013.01); *C12Q 1/6883* (2013.01); *C12Q 2600/112* (2013.01); *C12Q 2600/118* (2013.01); *C12Q 2600/158* (2013.01); *C12Q 2600/178* (2013.01)

(58) Field of Classification Search
CPC .......................... A61K 31/713; C12N 2310/11
See application file for complete search history.

(56) References Cited

U.S. PATENT DOCUMENTS

2014/0004521 A1   1/2014  Yeh et al.

FOREIGN PATENT DOCUMENTS

| WO | WO-2010/055488 A2 | 5/2010 |
|---|---|---|
| WO | WO-2011/027332 A2 | 3/2011 |
| WO | WO-2013007387 A1 | 1/2013 |
| WO | WO-2013071169 A1 | 5/2013 |
| WO | WO-2013112741 A1 | 8/2013 |
| WO | WO-2018231851 A1 | 12/2018 |

OTHER PUBLICATIONS

Charlton, M et al. The Association of Circulating MicroRNAs (miRs) with Liver Fibrosis Stage and the Impact of Selonsertib Treatment in Patients with NASHat the International Liver Congress (ILC) of the European Association for the Study of the Liver (EASL) Apr. 11-15, 2018, Paris, France-Abstract FRI-463.
Charlton, M. et al."The Association of Circulating MicroRNAs (miRs) With Liver Fibrosis Stage and the Impact of Selonsertib Treatment in Patients With NASH" at the International Liver Congress™, Apr. 11-15, 2018, Paris, France-Poster FRI-463.
Written Opinion for PCT/US2018/037137 dated Nov. 13, 2018.
International Searching Authority at the European Patent Office, International Search Report and Written Opinion for PCT International Application No. PCT/US2018/037137, dated Nov. 13, 2018, 22 pages.
Murakami, et al., Comprehensive analysis of microRNA expression patterns in hepatocellular carcinoma and non-tumorous tissues, Oncogene, Apr. 1, 2006, pp. 2537-2545, vol. 25, No. 17.
Zhang, et al., Upregulation of miR-15b in NAFLD models and in the serum of patients with fatty liver disease, Diabetes Research and Clinical Practice, Mar. 1, 2013, pp. 327-334, vol. 99, No. 3.
Buzzetti, et al., Noninvasive Assessment of Fibrosis in Patients with Nonalcoholic Fatty Liver Disease, International Journal of Endocrinology, Jan. 22, 2015, 9 pages.
Kleiner, et al., Design and Validation of a Histological Scoring System for Nonalcoholic Fatty Liver Disease, Hepatology, Jun. 2005, pp. 1313-1321, vol. 41, No. 6.

*Primary Examiner* — Amy H Bowman

(57) ABSTRACT

The present application provides methods of diagnosing, treating, and/or monitoring a liver disease or condition in a human.

28 Claims, 1 Drawing Sheet

Specification includes a Sequence Listing.

Fig.1: Differential Expression of miR-136-5P and miR-125b in Patients With Advanced Fibrosis at Week 24

Fig 2: Differential Expression of miR-122-5p, miR-34a-5p, and miR-1260b in patients With Fibrosis Improvement, Worsening and No Change

METHODS OF TREATING LIVER FIBROSIS

CROSS-REFERENCES TO RELATED APPLICATIONS

This application claims benefit and priority to U.S. Provisional Application No. 62/518,696, filed Jun. 13, 2017, and U.S. Provisional Application No. 62/575,830, filed Oct. 23, 2017, each of which is incorporated herein in its entirety for all purposes.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 1215P2C_ST25.txt. The text file is 22 KB, and was created on Jun. 11, 2018, and is being submitted electronically via EFS-Web.

FIELD

Described herein are, generally, methods relating to liver fibrosis.

BACKGROUND OF THE INVENTION

Nonalcoholic steatohepatitis (NASH) is a liver inflammation condition caused by a buildup of fat in the liver and can lead to liver fibrosis. Current methods of determining whether a patient has NASH and/or fibrosis and current methods of monitoring NASH and/or fibrotic progression typically require a liver biopsy, which is an invasive surgery that requires significant resources and may not be an ideal tool for most patients. There is a need for developing diagnostic procedures or methods to reduce invasive surgeries.

BRIEF SUMMARY OF THE INVENTION

Provided herein are methods of diagnosing, treating, and monitoring a liver disease or condition in a human.

In some embodiments, provided are methods of diagnosing a liver disease or condition in a human. In some embodiments, provided are methods of treating a liver disease or condition in a human. In some embodiments, provided are methods of monitoring a liver disease or condition in a human. In some embodiments, provided are methods of detecting the levels of one or more miRNAs.

In some embodiments, provided are methods of diagnosing a liver disease or condition in a human, the method comprising detecting levels of one or more microRNAs (miRNAs) in the human. In some embodiments, provided are methods of treating a liver disease or condition in a human in a human, the method comprising detecting levels of one or more microRNAs (miRNAs) in the human and administering one or more therapeutic agents to the human. In some embodiments, provided are methods of monitoring a liver disease or condition in a human, the method comprising detecting levels of one or more microRNAs (miRNAs) in the human. In some embodiments, provided are methods of detecting the levels of one or more miRNAs, the method comprising detecting levels of one or more miRNAs in a first sample from a human. In some embodiments, provided are method of treating a liver disease or condition in a human, the method comprising administering one or more therapeutic agents to the human where the human has been identified as having a change in the levels of one or more miRNAs.

DETAILED DESCRIPTION OF THE INVENTION

I. General

Figure 1:
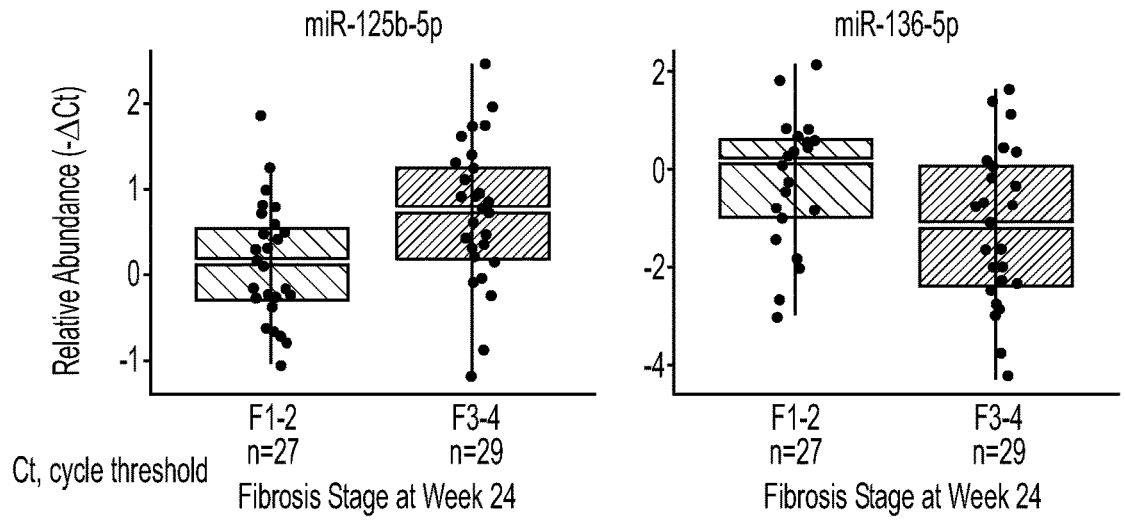
FIG. 1: Diagrams showing differential expression of miR-136-5P (right panel) and miR-125b-5p (left panel) in patients with advanced fibrosis at week 24.
Figure 2:
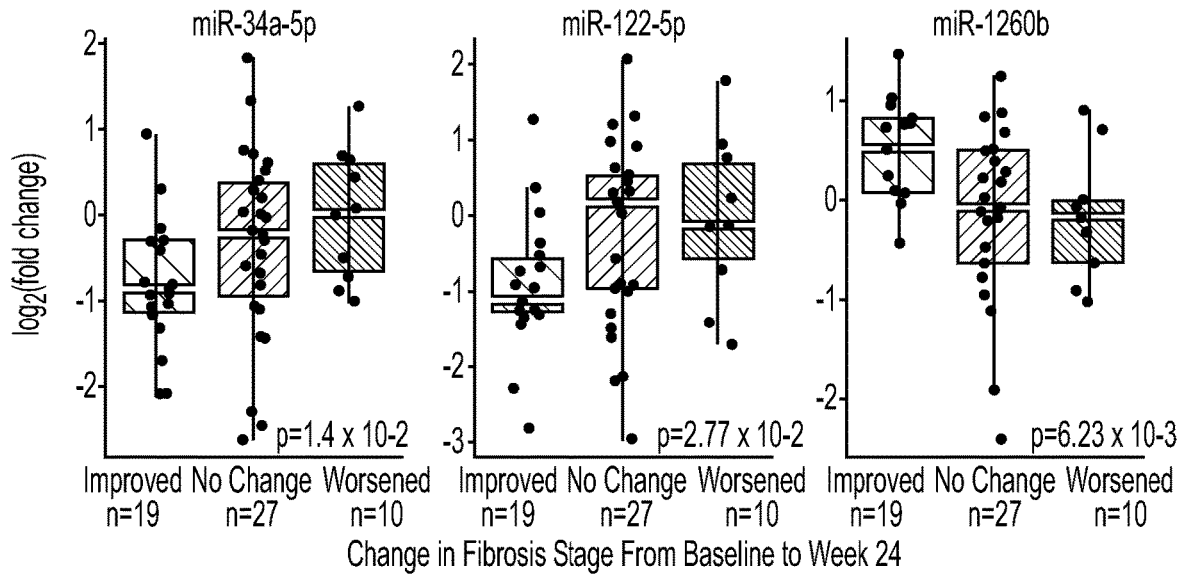
FIG. 2: Diagrams showing differential expression of miR-34a-5p (left panel), miR-122-5p (middle panel), and miR-1260b (right panel) in patients with fibrosis improvement, worsening and no change.

The following description sets forth exemplary methods, parameters and the like. It should be recognized, however, that such description is not intended as a limitation on the scope of the present disclosure but is instead provided as a description of exemplary embodiments.

II. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference. The headings provided herein are for convenience only and not as limitation in any way.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "some embodiments," "one embodiment," "an embodiment," "another embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention.

Thus, the appearances of the foregoing phrases in various places throughout this specification are not necessarily all referring to the same embodiment. Furthermore, the particular features, structures, or characteristics may be combined in any suitable manner in one or more embodiments.

A "control" sample or value refers to a sample that serves as a reference, usually a known reference, for comparison to a test sample. For example, a test sample can be taken from a test condition, e.g., in the presence of a test compound or in the presence of a liver disease or condition, and compared to samples from known conditions, e.g., in the absence of the test compound (negative control), or in the presence of a known compound (positive control), or in the absence of the liver disease or condition. A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

Described herein, a "control" such as a "control sample" may be used to correlate and compare the results obtained in the methods described herein from a test sample, in particular a sample from a subject to be diagnosed, herein also referred to simply as "sample". Typically, "control levels" are levels that are found in one or more healthy subjects and a "control sample" is obtained from a healthy subject, wherein the term "healthy subject" refers to a subject not having a liver disease or condition. A "control level" can be determined by measuring a sufficiently large number of control samples. In some embodiments, the control level is determined by measuring at least 2, at least 3, at least 5, at least 8, at least 12, at least 20, at least 30, at least 50, or at least 100 control samples.

As used herein, the terms "increase" or "decrease" generally refer to a change in the level of microRNA (miRNA) between two samples. An "increased" is typically "statistically significant", and may include an increase that is 1.1, 1.2, 1.5, 2, 3, 4, 5, 6, 7, 8, 9, 10, 15, 20, 30, or more times (e.g., 500, 1000 times) (including all integers and decimal points in between and above 1, e.g., 1.5, 1.6, 1.7. 1.8, etc.) that produced by another sample.

A "decrease" is typically "statistically significant" and may include a decrease that is 1.1, 1.2, 1.5, 2, 3, 4, 5, 6, 7, 8, 9, 10, 15, 20, 30, or more times (e.g., 500, 1000 times) (including all integers and decimal points in between and above 1, e.g., 1.5, 1.6, 1.7. 1.8, etc.) that produced by another sample. In some embodiments, a decreased level is represented with a negative value (e.g., −1.1 or −1.1 fold). In some embodiments, a decreased level is represented with a decimal less than 1 (e.g., 0.4 or 0.4-fold).

As used herein, the terms "level" or "levels" refer to the concentration or amount of miRNA. In one embodiment, the increase or decrease in the "level" of miRNA may refer to the quantified and normalized concentration of miRNA.

As used herein, the terms "microRNA" or "miRNA" refers to small non-coding ribonucleic acid (RNA) molecules typically comprising less than 25 nucleotides.

As used herein, the terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

As used herein, a polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

As used herein, the terms "homology" or "identity" or "similarity" refers to sequence similarity between two peptides or between two nucleic acid molecules. Homology can be determined by comparing a position in each sequence that may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention. In one embodiment, the homologous peptide is one that shares the same functional characteristics as those described, including one or more of the adaptive mutations.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example, those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE;

Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/blast/Blast.cgi, last accessed on Jul. 15, 2011. Biologically equivalent polynucleotides are those having the specified percent homology and encoding a polypeptide having the same or similar biological activity.

As used herein, the term "a homolog of a nucleic acid" refers to a nucleic acid having a nucleotide sequence having a certain degree of homology with the nucleotide sequence of the nucleic acid or complement thereof. A homolog of a double stranded nucleic acid is intended to include nucleic acids having a nucleotide sequence that has a certain degree of homology with or with the complement thereof. In one aspect, homologs of nucleic acids are capable of hybridizing to the nucleic acid or complement thereof.

As used herein, the term "sample" refers generally to a fluid from a human. Non-limiting examples of a sample include bile, blood, blood plasma, serum, breast milk, feces, pus, saliva, sebum, semen, sweat, tears, urine, and vomit. In some embodiments, the sample is serum.

As used herein, the term "subject" refers to a mammalian subject. Exemplary subjects include, but are not limited to humans, monkeys, dogs, cats, mice, rats, cows, horses, goats and sheep. In some embodiments, the subject is human. In some embodiments, the subject has a liver disease or condition and can be treated as described herein. In some embodiments, the subject has liver fibrosis. In some embodiments, the human has stage 3 or stage 4 (F3-4) liver fibrosis. In some embodiments, the subject has NASH. In some embodiments, the subject has NAFLD. In some embodiments, the subject has liver inflammation. In some embodiments, the subject has a NAS of 5 or above. In some embodiments, the subject has three or more features of metabolic syndrome (e.g., elevated blood pressure, abdominal obesity, elevated fasting plasma glucose, high serum triglycerides, and low high-density lipoprotein cholesterol). In some embodiments, the subject has a serum alanine aminotransferase (ALT) level between 1.5-fold to 5-fold of upper limit of normal (ULN). In some embodiments, the subject has a liver stiffness by FibroScan (Echosens®, Paris, France) of between 7 kPa and 12 kPa. In some embodiments, the subject has one or more correlates described in Buzzeti et al., International Journal of Endocrinology, 2015:1-9, the contents of which are incorporated herein as their entireties.

As used herein, the term "suspected" when referencing a patient refers to the potential for a patient to have a certain liver disease or condition based on a correlate. In some embodiments, the suspected patient has obesity. In some embodiments, the suspected patient has a BMI (body mass index) of 25 kg/m$^2$ or higher. In some embodiments, the suspected patient has triglycerides levels of 150 mg/dl or higher. In some embodiments, the suspected patient has insulin resistance. In some embodiments, the suspected patient has three or more features of metabolic syndrome (e.g., elevated blood pressure, abdominal obesity, elevated fasting plasma glucose, high serum triglycerides, and low high-density lipoprotein cholesterol). In some embodiments, the suspected patient has type 2 diabetes mellitus.

As used herein, the term "correlate" refers to a scoring system, clinical parameter, biomarker, or the like, that may be used to determine a disease or condition. For example, NAS is a scoring system correlate to that determines stages of NAFLD.

As used herein, the term "treatment," "treating," or similar language refers to a process to (1) delay onset of a disease that is causing clinical symptoms; (2) inhibiting a disease, that is, arresting the development of clinical symptoms; and/or (3) relieving the disease, that is, causing the regression of clinical symptoms or the severity thereof.

As used herein, the term "liver disease or condition" refers any one or more of the following: liver fibrosis, nonalcoholic steatohepatitis (NASH), non-alcoholic fatty liver disease (NAFLD), or liver inflammation.

As used herein, the term "liver fibrosis" refers an excessive accumulation of scar tissue.

As used herein, the term "NAS" refers to the NAFLD Activity Score, which is a scoring system for NAFLD.

As used herein, "Fibrosis Score" refers to a scoring system for fibrosis described by Kleiner et al. (2005), Design and validation of a histological scoring system for nonalcoholic fatty liver disease. Hepatology, 41: 1313-1321. doi: 10.1002/hep.20701.

As used herein, the term "one or more" refers to any integer between 1 and 150. For example, "one or more" may refer to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150.

III. Methods of Diagnosing a Liver Disease or Condition

Provided herein include methods of diagnosing a liver disease or condition in a human. In some embodiments, a method of diagnosing a liver disease or condition in a human, the method comprising detecting levels of one or more microRNAs (miRNAs) in the human. In some embodiments, provided is a method of diagnosing a liver disease or condition in a human, the method comprising detecting levels of one or more microRNAs (miRNAs) in a first sample from the human, wherein the levels of one or more miRNAs are correlated with a liver disease or condition. In some embodiments, the liver disease or condition is liver fibrosis, nonalcoholic steatohepatitis (NASH), non-alcoholic fatty liver disease (NAFLD) and/or liver inflammation.

In some embodiments, provided is a method of diagnosing a liver disease or condition in a human, the method comprising detecting levels of one or more microRNAs (miRNAs) in a first sample from the human, wherein one or more of the levels of one or more miRNAs are correlated with a liver disease or condition and the one or more miRNAs are selected from any miRNA panel described herein.

In some embodiments, the one or more miRNAs are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, and hsa-miR-127-3p.

In some embodiments, the method of diagnosing comprises detecting levels of one or more miRNAs in a first sample obtained from the human wherein the levels of one or more miRNAs are correlated with a liver disease or condition.

In some embodiments, the method further comprises administering one or more therapeutic agents to the human.

In some embodiments, the method further includes detecting levels of one or more miRNAs in a second sample obtained from the human, and comparing the levels of the one or more miRNAs in the second sample to the levels of the one or more miRNAs in the first sample, wherein a change in the levels of one or more miRNAs in the second sample compared to the levels of one or more miRNAs in the first sample is correlated with a liver disease or condition. In some embodiments, the first sample is obtained from the human prior to the second sample obtained from the human. In some embodiments, the first sample is obtained from the human 12 hours, 24 hours, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 1 month, 2 months, 3 months, 4 months, 5 months, 6 months, 7 months, 8 months, 9 months, 10 months, 11 months, 12 months, 1 year, 2 years, 3 years, 4 years, or 5 years prior to the second sample obtained from the human. In some embodiments, the first sample is obtained from the human prior to administering one or more therapeutic agents to the human and the second sample is obtained from the human after administering one or more therapeutic agents to the human.

In some embodiments, the method of diagnosing comprises detecting levels of the one or more miRNAs in a first sample obtained from the human, and comparing the levels of the one or more miRNAs in the first sample to control levels of the one or more miRNAs, wherein a change in one or more of the levels of the one or more miRNAs in the first sample compared to the control levels is correlated with a liver disease or condition. In some embodiments, the control levels of the one or more miRNAs are the levels of the one or more miRNAs in one or more control samples.

In some embodiments, provided is a method of diagnosing a liver disease or condition in a human, the method comprising (a) detecting levels of one or more miRNAs in a first sample obtained from the human, (b) optionally administering one or more therapeutic agents to the human, and (c) detecting levels of the one or more miRNAs in a second sample obtained from the human; wherein a change in one or more of the levels of one or more miRNAs in the second sample compared to the levels of one or more miRNAs in the first sample is correlated with a liver disease or condition.

In some embodiments, the one or more miRNAs detected in any method described herein are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, and hsa-miR-127-3p.

In some embodiments, the one or more miRNAs detected in any method described herein are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, and hsa-miR-324-3p.

In some embodiments, the one or more miRNAs detected in any method described herein are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132.

In some embodiments, the one or more miRNAs detected in any method described herein are selected from the group consisting of hsa-miR-15b, hsa-miR-17, hsa-miR-451, hsamiR-15a, has-miR-19b, hsa-miR-483-3p, hsa-miR-499-3p, hsa-miR-181d, hsa-miR-124, and hsa-miR-34a.

In some embodiments, the one or more miRNAs detected in any method described herein include at least one miRNA selected from the group consisting of hsa-miR-451, hsa-miR-124, and hsa-miR-34a; and at least one miRNA selected from the group consisting of hsa-miR-15b, hsa-miR-17, hsa-miR-15a, has-miR-19b, hsa-miR-483-3p, hsa-miR-499-3p, and hsa-miR-181d. In some embodiments, the one or more miRNAs further include at least one miRNA selected from the group consisting of hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-125b, hsa-miR-362-5p, hsa-miR-512-3p, hsa-miR-485-3p, hsa-miR-132, hsa-miR-92a, hsa-let-7b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-18 b, hsa-miR-493, hsa-miR-10a, hsa-miR-10b, hsa-miR-139-5p, hsa-miR-326, hsa-miR-423-3p, hsa-miR-187, and hsa-miR-127-3p.

In some embodiments, the one or more miRNAs comprise one or more miRNAs selected from the group consisting of hsa-miR-146a-5p, hsa-miR-146b-5p, hsa-miR-151a-5p, hsa-miR-223-3p, hsa-miR-590-5p, hsa-miR-155-5p, and hsa-miR-222-3p.

In some embodiments, the one or more miRNAs comprise hsa-miR-29a-3p, hsa-miR-125b-5p, and hsa-miR-150-5p.

In some embodiments, the one or more miRNAs comprise one or more miRNAs selected from the group consisting of hsa-miR-222-3p, hsa-miR-320d, hsa-miR-10b-5p, hsa-miR-139-5p, hsa-miR-143-3p, hsa-miR-338-3p, hsa-miR-326, hsa-miR-874-3p, hsa-miR-29b-3p, hsa-let-7i-5p, hsa-miR-30a-5p, hsa-miR-320c, hsa-miR-342-3p, hsa-miR-192-5p, hsa-miR-29c-3p, hsa-miR-32-5p, hsa-miR-185-5p, hsa-miR-324-3p, hsa-miR-375, and hsa-miR-93-5p.

In some embodiments, the change in the levels of the one or more miRNAs is an increase in the level of a first miRNA among the one or more miRNAs or a decrease in the level of a second miRNA among the one or more miRNAs, or both. In some embodiments, an increase in the level of miRNA in the first sample compared to that of the control sample (i.e., control level) is correlated to a liver disease or condition in a human. In some embodiments, a decrease in the level of miRNA in the first sample compared to that of the control sample (i.e., control level) is correlated to a liver disease or condition in a human. In some embodiments, an increase in the level of miRNA in the second sample compared to that of the first sample is correlated to a liver disease or condition in a human. In some embodiments, a decrease in the level of miRNA in the second sample compared to that of the first sample is correlated to a liver disease or condition in a human. In some embodiments, an increase in the level of a first miRNA and a decrease in the level of a second miRNA are correlated to a liver disease or condition in a human.

In some embodiments, an increase in the level of miRNA of at least a 1-fold change is correlated to a liver disease or condition in a human. In some embodiments, an increase in the level of miRNA of at least a 2-fold change is correlated to a liver disease or condition in a human. In some embodiments, an increase in the level of miRNA of at least a 3-fold change is correlated to a liver disease or condition in a human.

In some embodiments, a decrease in the level of miRNA of at least a 0.6-fold (i.e., −1.7 fold) change is correlated to a liver disease or condition in a human. In some embodiments, a decrease in the level of miRNA of at least a 0.5-fold (i.e., −2 fold) change is correlated to a liver disease or condition in a human. In some embodiments, a decrease in the level of miRNA of at least a 0.4-fold (i.e., −2.5 fold) change is correlated to a liver disease or condition in a human.

In some embodiments, an increase in the level of a first miRNA at least a 1-fold change and a decrease in the level of a second miRNA of at least a 0.6-fold change is correlated to a liver disease or condition in a human. In some embodiments, an increase in the level of a first miRNA of at least a 2-fold change and a decrease in the level of a second miRNA of at least a 0.5-fold change is correlated to a liver disease or condition in a human. In some embodiments, an increase in the level of a first miRNA of at least a 3-fold change and a decrease in the level of a second miRNA f of at least a 0.4-fold change is correlated to a liver disease or condition in a human.

In some embodiments, the change includes an increase in the level of the first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, and hsa-miR-378 in the second sample compare to the first sample or in the first sample compared to the control levels.

In some embodiments, the change includes a decrease in the level of the second miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, and hsa-miR-127-3p in the second sample compare to the first sample or in the first sample compared to the control levels.

In some embodiments, the change includes an increase of the level of the first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, and hsa-miR-378 in the second sample compared to the first sample or in the first sample compared to the control levels and/or a decrease of the level of the second miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, and hsa-miR-127-3p in the second sample compared to the first sample or in the first sample compared to the control levels.

In some embodiments, the change comprises an increase of the level of the first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, and hsa-miR-18b in the second sample compared to the first sample or in the first sample compared to the control levels and/or a decrease of the level of the second miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, and hsa-miR-324-3p in the second sample compared to the first sample or in the first sample compared to the control levels.

In some embodiments, the change comprises an increase of the level of the first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, and hsa-miR-424 in the second sample compared to the first sample or in the first sample compared to the control levels and/or a decrease of the level of the second miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132 in the second sample compared to the first sample or in the first sample compared to the control levels.

In some embodiments, the change includes an increase of the first miRNA selected from the group consisting of hsa-miR-15b, hsa-miR-17, hsa-miR-451, hsa-miR-15a, and has-miR-19b in the second sample compared to the first sample or in the first sample compared to the control levels.

In embodiments, the change includes a decrease of the second miRNA selected from the group consisting of hsa-miR-483-3p, hsa-miR-499-3p, hsa-miR-181d, hsa-miR-124, and hsa-miR-34a in the second sample compared to the first sample or in the first sample compared to the control levels In some embodiments, the change comprises an increase of the level of the first miRNA selected from the group consisting of hsa-miR-15b, hsa-miR-17, hsa-miR-451, hsa-miR-15a, and has-miR-19b in the second sample compared to the first sample or in the first sample compared to the control levels and/or a decrease of the level of the second miRNA selected from the group consisting of hsa-miR-483-3p, hsa-miR-499-3p, hsa-miR-181d, hsa-miR-124, and hsa-miR-34a in the second sample compared to the first sample or in the first sample compared to the control levels In some embodiments, provided is a method of diagnosing a liver disease or condition in a human, the method comprising (a) detecting levels of one or more miRNAs in a first sample obtained from the human, (b) administering one or more therapeutic agents to the human, and (c) detecting levels of one or more miRNAs in a second sample obtained from the human; wherein a change in one or more of the levels of the one or more miRNAs in the second sample compared to those of the first sample are correlated with a liver disease or condition wherein the change comprises an increase of the level of a first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, and hsa-miR-424 in the second sample compared to the first sample and/or a decrease of the level of a second miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132 in the second sample compared to the first sample.

In some embodiments, provided is a method of diagnosing a liver disease or condition in a human, the method comprising (a) detecting levels of one or more miRNAs in a first sample obtained from the human, (b) administering one or more therapeutic agents to the human, and (c) detecting levels of one or more miRNAs in a second sample obtained from the human; wherein a change in one or more of the levels of the one or more miRNAs are correlated with a liver disease or condition wherein the change comprises an increase of at least 2-fold the level of a first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, and hsa-miR-424 in the second sample compared to the first sample and/or a decrease of at least 0.5-fold the level of a second miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132 in the second sample compared to the first sample.

IV. Methods of Treating a Liver Disease or Condition

Also provided herein are methods of treating a liver disease or condition in a human. In some embodiments, a method of treating a liver disease or condition in a human, the method comprising detecting levels of one or more microRNAs (miRNAs) in the human and administering one or more therapeutic agents to the human. In some embodiments, provided is a method of treating a liver disease or condition in a human, the method comprising detecting levels of one or more microRNAs (miRNAs) in the human and administering one or more therapeutic agents to the human, wherein the levels of one or more miRNAs are correlated with a liver disease or condition. In some embodiments, the liver disease or condition is liver fibrosis, non-alcoholic steatohepatitis (NASH), non-alcoholic fatty liver disease (NAFLD) and/or liver inflammation. Other liver diseases that can be treated using the miRNAs of the present invention include, but are not limited to, primary biliary cholangitis, and primary sclerosing cholangitis. In some embodiments, the liver disease or condition is primary biliary cholangitis or primary sclerosing cholangitis. In some embodiments, the liver disease or condition is primary biliary cholangitis. In some embodiments, the liver disease or condition is primary sclerosing cholangitis.

In some embodiments, provided is a method of treating a liver disease or condition in a human, the method comprising detecting levels of one or more microRNAs (miRNAs) in a first sample from the human and administering one or more therapeutic agents to the human, wherein the levels of one or more miRNAs are correlated with a liver disease or condition and the one or more miRNAs are selected from any miRNA panel described herein.

In some embodiments, provided herein is a therapeutic agent for use in a method of treating a liver disease or condition in a human, the method comprising detecting levels of one or more microRNAs (miRNAs) in a first sample from the human, and administering one or more therapeutic agents to the human, wherein the one or more miRNAs are selected from any miRNA panel described herein.

In some embodiments, provided is a method of treating a liver disease or condition in a human, the method comprising detecting levels of one or more microRNAs (miRNAs) in a first sample from the human for diagnosing a liver disease or condition in the human and administering one or more therapeutic agents effective in the treatment of a liver disease or condition to the human, if a liver disease or condition is diagnosed in the human, wherein the one or more miRNAs are selected from any miRNA panel described herein.

In some embodiments, provided herein is a therapeutic agent effective in the treatment of a liver disease or condition for use in a method of treating a liver disease or condition in a human, the method comprising detecting levels of one or more microRNAs (miRNAs) in a first sample from the human for diagnosing a liver disease or condition in the human, and administering one or more therapeutic agents effective in the treatment of a liver disease or condition to the human, if a liver disease or condition is diagnosed in the human, wherein the one or more miRNAs are selected from any miRNA panel described herein.

In some embodiments, the one or more miRNAs detected in any method described herein are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, hsa-miR-127-3p, hsa-miR-136-5p, hsa-miR-30a-5p, hsa-miR-29c-3p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-222-3p, hsa-miR-365a-3p, hsa-miR-22-5p, hsa-miR-505-3p, hsa-miR-885-5p, hsa-miR-107, hsa-miR-100-5p, hsa-miR-155-5p, and hsa-miR-874-3p.

In some embodiments, the method of treating comprises detecting levels of one or more miRNAs in a first sample obtained from the human wherein the levels of one or more miRNAs are correlated with a liver disease or condition.

In some embodiments, the method further comprises detecting levels of one or more miRNAs in a second sample obtained from the human, and comparing the levels of the one or more miRNAs in the second sample to the levels of the one or more miRNAs in the first sample, wherein a change in one or more of the levels of one or more miRNAs in the second sample compared to the levels of one or more miRNAs in the first sample is correlated with a liver disease or condition. In some embodiments, the first sample is obtained from the human prior to the second sample from the human. In some embodiments, the first sample is obtained from the human 12 hours, 24 hours, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 1 month, 2 months, 3 months, 4 months, 5 months, 6 months, 7 months, 8 months, 9 months, 10 months, 11 months, 12 months, 1 year, 2 years, 3 years, 4 years, or 5 years prior to the second sample obtained from the human. In some embodiments, the first sample is obtained from the human prior to administering one or more therapeutic agents to the human and the second sample is obtained from the human after administering one or more therapeutic agents to the human.

In some embodiments, the method of treating comprises detecting levels of the one or more miRNAs in a first sample obtained from the human, comparing the levels of the one or more miRNAs in the first sample to control levels of the one or more miRNAs, and administering one or more therapeutic agents to the human, wherein a change in one or more of the levels of the one or more miRNAs in the first sample compared to the control levels is correlated with a liver disease or condition. In some embodiments, the control levels of the one or more miRNAs are the levels of the one or more miRNAs in one or more control samples.

In some embodiments, the one or more miRNAs detected in any method described herein are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, and hsa-miR-324-3p.

In some embodiments, the one or more miRNAs detected in any method described herein are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132.

In some embodiments, the one or more miRNAs detected in any method described herein are selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, hsa-miR-375, hsa-miR-1260b, hsa-miR-365a-3p, hsa-miR-215-5p, hsa-miR-194-5p, hsa-let-7i-5p, hsa-miR-122-5p, hsa-miR-192-5p, hsa-miR-222-3p, hsa-miR-378a-3p, hsa-miR-30a-5p, hsa-miR-365a-3p, hsa-miR-22-5p, hsa-miR-505-3p, hsa-miR-320d, hsa-miR-885-5p, hsa-miR-107, hsa-miR-100-5p, hsa-miR-148a-3p, hsa-miR-155-5p, hsa-miR-146a-5p, hsa-miR-125b-5p, hsa-miR-139-5p, hsa-miR-874-3p, and hsa-miR-10b-5p.

In some embodiments, the one or more miRNAs detected in any method described herein are selected from the group consisting of hsa-miR-505-3p, hsa-miR-29a-3p, hsa-miR-215-5p, hsa-miR-148a-3p, hsa-miR-99a-5p, hsa-miR-885-5p, hsa-miR-122-5p, hsa-miR-34a-5p, hsa-miR-365a-3p, hsa-miR-194-5p, and hsa-miR-155-5p.

In some embodiments, the one or more miRNAs detected in any method described herein are selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, and hsa-miR-375.

In some embodiments, the one or more miRNAs detected in any method described herein comprise hsa-miR-34a-5p; and at least one miRNA selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, and hsa-miR-375.

In some embodiments, the one or more miRNAs detected in any method described herein are selected from the group consisting of hsa-miR-125b-5p, hsa-miR-34a-5p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-122-5p, hsa-miR-192-5p and hsa-miR-222-3p.

In some embodiments, the one or more miRNAs detected in any method described herein comprise hsa-miR-1260b; and optionally at least one miRNA selected from the group consisting of hsa-miR-125b-5p, hsa-miR-34a-5p, hsa-miR-378a-3p, hsa-miR-99a-5p, hsa-miR-365a-3p, hsa-miR-215-5p, hsa-miR-194-5p, hsa-let-7i-5p, hsa-miR-122-5p, hsa-miR-192-5p and hsa-miR-222-3p.

In some embodiments, the one or more miRNAs detected in any method described herein are selected from the group consisting of hsa-miR-125b-5p, hsa-miR-29a-3p, hsa-miR-378a-3p, hsa-miR-30a-5p, hsa-miR-34a-5, hsa-miR-99a-5p, hsa-miR-192-5p, hsa-miR-365a-3p, hsa-miR-22-5p, hsa-miR-505-3p, hsa-miR-320d, hsa-miR-215-5p, hsa-miR-122-5p, hsa-miR-194-5p, hsa-miR-885-5p, and hsa-miR-107.

In some embodiments, the one or more miRNAs detected in any method described herein are selected from the group consisting of hsa-miR-122-5p, hsa-miR-125b-5p, hsa-miR-365a-3p, hsa-miR-192-5p, hsa-miR-215-5p, hsa-miR-885-5p, hsa-miR-505-3p, hsa-miR-194-5p, hsa-miR-99a-5p, hsa-miR-34a-5p, hsa-miR-378a-3p.

In some embodiments, the one or more miRNAs detected in any method described herein are selected from the group consisting of hsa-miR-29a-3p, hsa-miR-146a-5p, hsa-miR-125b-5p, and hsa-miR-150-5p. In some embodiments, the one or more miRNAs include hsa-miR-29a-3p, hsa-miR-146a-5p, hsa-miR-125b-5p, and hsa-miR-150-5p.

In some embodiments, the one or more miRNAs detected in any method described herein are selected from the group consisting of hsa-miR-222-3p, hsa-miR-10b-5p, hsa-miR-139-5p, and hsa-miR-8743-p. In some embodiments, the one or more miRNAs include hsa-miR-222-3p, hsa-miR-10b-5p, hsa-miR-139-5p, and hsa-miR-8743-p.

In some embodiments, the one or more miRNAs comprise one or more miRNAs selected from the group consisting of hsa-miR-146a-5p, hsa-miR-146b-5p, hsa-miR-151a-5p, hsa-miR-223-3p, hsa-miR-590-5p, hsa-miR-155-5p, and hsa-miR-222-3p.

In some embodiments, the one or more miRNAs comprise hsa-miR-29a-3p, hsa-miR-125b-5p, and hsa-miR-150-5p.

In some embodiments, the one or more miRNAs comprise one or more miRNAs selected from the group consisting of hsa-miR-222-3p, hsa-miR-320d, hsa-miR-10b-5p, hsa-miR-139-5p, hsa-miR-143-3p, hsa-miR-338-3p, hsa-miR-326, hsa-miR-874-3p, hsa-miR-29b-3p, hsa-let-7i-5p, hsa-miR-30a-5p, hsa-miR-320c, hsa-miR-342-3p, hsa-miR-192-5p, hsa-miR-29c-3p, hsa-miR-32-5p, hsa-miR-185-5p, hsa-miR-324-3p, hsa-miR-375, and hsa-miR-93-5p.

In some embodiments, the method described herein further includes performing a magnetic resonance elastography (MRE) on the human prior to administering one or more therapeutic agents to the human.

In some embodiments, provided is a method of treating a liver disease or condition in a human, wherein the human has increased levels of one or more miRNAs selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, and hsa-miR-378 in a second sample compared to a first sample or in a first sample compared to control levels.

In some embodiments, provided is a method of treating a liver disease or condition in a human, wherein the human has decreased levels of one or more miRNAs selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, and hsa-miR-127-3p in a second sample compared to a first sample or in a first sample compared to control levels.

In some embodiments, provided is a method of treating a liver disease or condition in a human, the method comprising (a) detecting levels of one or more miRNAs in a first sample obtained from the human, (b) administering one or more therapeutic agents to the human, and (c) detecting levels of the one or more miRNAs in a second sample obtained from the human; wherein a change in one or more of the levels of the one or more miRNAs in the second sample compared to the levels of the one or more miRNAs in the first sample is correlated with a liver disease or condition, and wherein the one or more miRNAs are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, hsa-miR-127-3p, hsa-miR-136-5p, hsa-miR-30a-5p, hsa-miR-29c-3p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-222-3p, hsa-miR-365a-3p, hsa-miR-22-5p, hsa-miR-505-3p, hsa-miR-885-5p, hsa-miR-107, hsa-miR-100-5p, hsa-miR-155-5p, and hsa-miR-874-3p.

In some embodiments, the one or more miRNAs detected in any method described herein are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, and hsa-miR-324-3p.

In some embodiments, the one or more miRNAs detected in any method described herein are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132.

In some embodiments, the one or more miRNAs detected in any method described herein are selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, hsa-miR-375, hsa-miR-1260b, hsa-miR-365a-3p, hsa-miR-215-5p, hsa-miR-194-5p, hsa-let-7i-5p, hsa-miR-122-5p, hsa-miR-192-5p, hsa-miR-222-3p, hsa-miR-378a-3p, hsa-miR-30a-5p, hsa-miR-365a-3p, hsa-miR-22-5p, hsa-miR-505-3p, hsa-miR-320d, hsa-miR-885-5p, hsa-miR-107, hsa-miR-100-5p, hsa-miR-148a-3p, hsa-miR-155-5p, hsa-miR-146a-5p, hsa-miR-125b-5p, hsa-miR-139-5p, hsa-miR-874-3p, and hsa-miR-10b-5p.

In some embodiments, the one or more miRNAs detected in any method described herein are selected from the group consisting of hsa-miR-505-3p, hsa-miR-29a-3p, hsa-miR-215-5p, hsa-miR-148a-3p, hsa-miR-99a-5p, hsa-miR-885-5p, hsa-miR-122-5p, hsa-miR-34a-5p, hsa-miR-365a-3p, hsa-miR-194-5p, and hsa-miR-155-5p.

In some embodiments, the one or more miRNAs detected in any method described herein are selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, and hsa-miR-375.

In some embodiments, the one or more miRNAs detected in any method described herein comprise hsa-miR-34a-5p; and at least one miRNA selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, and hsa-miR-375.

In some embodiments, the one or more miRNAs detected in any method described herein are selected from the group consisting of hsa-miR-125b-5p, hsa-miR-34a-5p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-122-5p, hsa-miR-192-5p and hsa-miR-222-3p.

In some embodiments, the one or more miRNAs detected in any method described herein comprise hsa-miR-1260b; and optionally at least one miRNA selected from the group consisting of hsa-miR-125b-5p, hsa-miR-34a-5p, hsa-miR-378a-3p, hsa-miR-99a-5p, hsa-miR-365a-3p, hsa-miR-215-5p, hsa-miR-194-5p, hsa-let-7i-5p, hsa-miR-122-5p, hsa-miR-192-5p and hsa-miR-222-3p.

In some embodiments, the one or more miRNAs detected in any method described herein are selected from the group consisting of hsa-miR-125b-5p, hsa-miR-29a-3p, hsa-miR-378a-3p, hsa-miR-30a-5p, hsa-miR-34a-5, hsa-miR-99a-5p, hsa-miR-192-5p, hsa-miR-365a-3p, hsa-miR-22-5p, hsa-miR-505-3p, hsa-miR-320d, hsa-miR-215-5p, hsa-miR-122-5p, hsa-miR-194-5p, hsa-miR-885-5p, and hsa-miR-107.

In some embodiments, the one or more miRNAs detected in any method described herein are selected from the group consisting of hsa-miR-122-5p, hsa-miR-125b-5p, hsa-miR-365a-3p, hsa-miR-192-5p, hsa-miR-215-5p, hsa-miR-885-5p, hsa-miR-505-3p, hsa-miR-194-5p, hsa-miR-99a-5p, hsa-miR-34a-5p, and hsa-miR-378a-3p.

In some embodiments, the one or more miRNAs are selected from the group consisting of hsa-miR-29a-3p, hsa-miR-146a-5p, hsa-miR-125b-5p, and hsa-miR-150-5p. In some embodiments, the one or more miRNAs include hsa-miR-29a-3p, hsa-miR-146a-5p, hsa-miR-125b-5p, and hsa-miR-150-5p.

In some embodiments, the one or more miRNAs detected in any method described herein are selected from the group consisting of hsa-miR-222-3p, hsa-miR-10b-5p, hsa-miR-139-5p, and hsa-miR-8743-p. In some embodiments, the one or more miRNAs detected in any method described herein include hsa-miR-222-3p, hsa-miR-10b-5p, hsa-miR-139-5p, and hsa-miR-8743-p.

In some embodiments, the method described herein further includes performing a magnetic resonance elastography (MRE) on the human prior to administering one or more therapeutic agents to the human.

In some embodiments, the change in the levels of the one or more miRNAs is an increase in the level of a first miRNA among the one or more miRNAs or a decrease in the level of a second miRNA among the one or more miRNAs, or both. In some embodiments, an increase in the level of miRNA in the first sample compared to that of the control level is correlated to a liver disease or condition in a human. In some embodiments, a decrease in the level of miRNA in the first sample compared to that of the control level is correlated to a liver disease or condition in a human. In some embodiments, an increase in the level of miRNA in the second sample compared to that of the first sample is correlated to a liver disease or condition in a human. In some embodiments, a decrease in the level of miRNA in the second sample compared to that of the first sample is correlated to a liver disease or condition in a human. In some embodiments, an increase in the level of a first miRNA and a decrease in the level of a second miRNA is correlated to a liver disease or condition in a human.

In some embodiments, an increase in the level of miRNA of at least a 1-fold change is correlated to a liver disease or condition in a human. In some embodiments, an increase in the level of miRNA of at least a 2-fold change is correlated to a liver disease or condition in a human. In some embodiments, an increase in the level of miRNA of at least a 3-fold change is correlated to a liver disease or condition in a human.

In some embodiments, a decrease in the level of miRNA of at least a 0.6-fold change is correlated to a liver disease or condition in a human. In some embodiments, a decrease in the level of miRNA of at least a 0.5-fold change is correlated to a liver disease or condition in a human. In some embodiments, a decrease in the level of miRNA of at least a 0.4-fold change is correlated to a liver disease or condition in a human.

In some embodiments, an increase in the level of a first miRNA of at least a 1-fold change and a decrease in the level of a second miRNA of at least a 0.6-fold change is correlated to a liver disease or condition in a human. In some embodiments, an increase in the level of a first miRNA of at least a 2-fold change and a decrease in the level of a second miRNA of at least a 0.5-fold change is correlated to a liver disease or condition in a human. In some embodiments, an increase in the level of a first miRNA of at least a 3-fold change and a decrease in the level of a second miRNA of at least a 0.4-fold change is correlated to a liver disease or condition in a human.

In some embodiments, the change includes an increase in the level of the first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, and hsa-miR-378 in the first sample compared to the control levels or in the second sample compared to the first sample.

In some embodiments, the change includes a decrease in the level of the second miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, and hsa-miR-127-3p in the first sample compared to the control levels or in the second sample compared to the first sample.

In some embodiments, the change includes an increase of the level of the first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, and hsa-miR-378 in the second sample compared to the first sample or in the first sample compared to the control levels and/or a decrease of the level of the second miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, and hsa-miR-127-3p in the second sample compared to the first sample or in the first sample compared to the control levels.

In some embodiments, the change comprises an increase of the level of the first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, and hsa-miR-18b in the second sample compared to the first sample or in the first sample compared to the control levels and/or a decrease of the level of the second miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, and hsa-miR-324-3p in the second sample compared to the first sample or in the first sample compared to the control levels.

In some embodiments, the change comprises an increase of the level of the first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, and hsa-miR-424 in the second sample compared to the first sample or in the first sample compared to the control sample and/or a decrease of the level of the second miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132 in the second sample compared to the first sample or in the first sample compared to the control levels.

In some embodiments, the change comprises an increase of the level of the first miRNA selected from the group consisting of hsa-miR-125b-5p, hsa-miR-29a-3p, hsa-miR-150-5p, hsa-miR-30a-5p, hsa-miR-34a-5p, hsa-miR-29c-3p, hsa-miR-378a-3p, hsa-miR-99a-5p, and hsa-miR-375 in the second sample compared to the first sample or in the first sample compared to the control levels and/or a decrease of the level of the second miRNA hsa-miR-136-5p in the second sample compared to the first sample or in the first sample compared to the control levels.

In some embodiments, an increase in the level of the first miRNA comprising hsa-miR-125b-5p, hsa-miR-29a-3p, hsa-miR-150-5p, hsa-miR-30a-5p, hsa-miR-34a-5p, hsa-miR-29c-3p, hsa-miR-378a-3p, hsa-miR-99a-5p, hsa-miR-375 or any combination thereof in the second sample compared to the first sample or in the first sample compared to the control levels indicates the human has stage 3-4 liver fibrosis.

In some embodiments, a decrease in the level of the second miRNA comprising hsa-miR-136-5p in the second sample compared to the first sample or in the first sample compared to the control levels indicates the human has stage 3-4 liver fibrosis.

In some embodiments, the human is likely to receive a liver transplant when diagnosed with stage 3-4 liver fibrosis.

In some embodiments, no change or a decrease in the level of the first miRNA comprising hsa-miR-125b-5p, hsa-miR-29a-3p, hsa-miR-150-5p, hsa-miR-30a-5p, hsa-miR-34a-5p, hsa-miR-29c-3p, hsa-miR-378a-3p, hsa-miR-99a-5p, hsa-miR-375 or any combination thereof in the second sample compared to the first sample or in the first sample compared to the control levels indicates the human has stage 1-2 liver fibrosis.

In some embodiments, no change or an increase in the level of the second miRNA comprising hsa-miR-136-5p in the second sample compared to the first sample or in the first sample compared to the control levels indicates the human has stage 1-2 liver fibrosis.

In some embodiments, the human is likely to change lifestyle when diagnosed with stage 1-2 liver fibrosis. Lifestyle changes include, but are not limited to, dietary modifications (e.g., caloric restriction, carbohydrate restriction, and/or fat restriction) and increased physical activity.

In some embodiments, an increase in the level of one or more miRNAs selected from the group consisting of hsa-miR-125b-5p, hsa-miR-34a-5p, hsa-miR-378a-3p, hsa-miR-99a-5p, hsa-miR-365a-3p, hsa-miR-215-5p, hsa-miR-194-5p, hsa-miR-122-5p, and hsa-miR-192-5p indicates a progression (i.e., worsening) in fibrosis stage. In some embodiments, a decrease in the levels of one or more miRNAs selected from the group consisting of hsa-miR-1260b, hsa-let-7i-5p, and hsa-miR-222-3p indicates a progression in fibrosis stage. A skilled practitioner or physician in the field would select appropriate one or more therapeutic agents or treatment regimen for such patients.

In some embodiments, a decrease in the levels of one or more miRNAs selected from the group consisting of hsa-miR-125b-5p, hsa-miR-34a-5p, hsa-miR-378a-3p, hsa-miR-99a-5p, hsa-miR-365a-3p, hsa-miR-215-5p, hsa-miR-194-5p, hsa-miR-122-5p, and hsa-miR-192-5p indicates a regression (i.e., an improvement) in fibrosis stage. In some embodiments, an increase in the levels of one or more miRNAs selected from the group consisting of hsa-miR-1260b, hsa-let-7i-5p, and hsa-miR-222-3p indicates a regression in fibrosis stage. A skilled practitioner or physician in the field would select appropriate one or more therapeutic agents or treatment regimen for such patients.

In some embodiments, provided is a method of treating a liver disease or condition in a human, the method comprising (a) detecting levels of one or more miRNAs in a first sample obtained from the human, (b) administering one or more therapeutic agents to the human, and (c) detecting levels of one or more miRNAs in a second sample obtained from the human; wherein a change in one or more of the levels of one or more miRNAs is correlated with a liver disease or condition, wherein the change in one or more of the levels of one or more miRNAs comprise an increase of the level of the first miRNA including hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424 or any combination thereof in the second sample compared to the first sample and/or a decrease of the level of the second miRNA including hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132 or any combination thereof in the second sample compared to the first sample.

Also provided herein are methods of treating a liver disease or condition in a human, the method comprising administering one or more therapeutic agents to the human, where the human has been identified as having a change in one or more of the levels of one or more miRNAs selected from any miRNA panel described herein.

In some embodiments, provided herein is a therapeutic agent for use in a method of treating a liver disease or condition in a human, the method comprising administering one or more therapeutic agents to the human, where the human has been identified as having a change in one or more of the levels of one or more miRNAs selected from any miRNA panel described herein In some embodiments, the one or more miRNAs are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, hsa-miR-127-3p, hsa-miR-136-5p, hsa-miR-30a-5p, hsa-miR-29c-3p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-222-3p, hsa-miR-365a-3p, hsa-miR-22-5p, hsa-miR-505-3p, hsa-miR-885-5p, hsa-miR-107, hsa-miR-100-5p, hsa-miR-155-5p, and hsa-miR-874-3p.

In some embodiments, the change is identified by comparing the levels of the one or more miRNAs in a second sample from the human to the levels of the one or more miRNAs in a first sample from the human.

In some embodiments, the change is identified by comparing the levels of the one or more miRNAs in a first sample from the human to control levels of the one or more miRNAs. In some embodiments, the control levels of the one or more miRNAs are the levels of the one or more miRNAs in one or more control samples.

In some embodiments, the one or more miRNAs are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, and hsa-miR-324-3p.

In some embodiments, the one or more miRNAs are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132.

In some embodiments, the one or more miRNAs are selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, hsa-miR-375, hsa-miR-1260b, hsa-miR-365a-3p, hsa-miR-215-5p, hsa-miR-194-5p, hsa-let-7i-5p, hsa-miR-122-5p, hsa-miR-192-5p, hsa-miR-222-3p, hsa-miR-378a-3p, hsa-miR-30a-5p, hsa-miR-365a-3p, hsa-miR-22-5p, hsa-miR-505-3p, hsa-miR-320d, hsa-miR-885-5p, hsa-miR-107, hsa-miR-100-5p, hsa-miR-148a-3p, hsa-miR-155-5p, hsa-miR-146a-5p, hsa-miR-125b-5p, hsa-miR-139-5p, hsa-miR-874-3p, and hsa-miR-10b-5p.

In some embodiments, the one or more miRNAs are selected from the group consisting of hsa-miR-505-3p, hsa-miR-29a-3p, hsa-miR-215-5p, hsa-miR-148a-3p, hsa-miR-99a-5p, hsa-miR-885-5p, hsa-miR-122-5p, hsa-miR-34a-5p, hsa-miR-365a-3p, hsa-miR-194-5p, and hsa-miR-155-5p.

In some embodiments, the one or more miRNAs are selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, and hsa-miR-375.

In some embodiments, the one or more miRNAs comprise hsa-miR-34a-5p; and at least one miRNA selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, and hsa-miR-375.

In some embodiments, the one or more miRNAs are selected from the group consisting of hsa-miR-125b-5p, hsa-miR-34a-5p, hsa-miR-378a-3p, hsa-miR-99a-5p, hsamiR-1260b, hsa-miR-365a-3p, hsa-miR-215-5p, hsa-miR-194-5p, hsa-let-7i-5p, hsa-miR-122-5p, hsa-miR-192-5p and hsa-miR-222-3p.

In some embodiments, the one or more miRNAs comprise hsa-miR-1260b; and optionally at least one miRNA selected from the group consisting of hsa-miR-125b-5p, hsa-miR-34a-5p, hsa-miR-378a-3p, hsa-miR-99a-5p, hsa-miR-365a-3p, hsa-miR-215-5p, hsa-miR-194-5p, hsa-let-7i-5p, hsa-miR-122-5p, hsa-miR-192-5p and hsa-miR-222-3p.

In some embodiments, the one or more miRNAs are selected from the group consisting of hsa-miR-125b-5p, hsa-miR-29a-3p, hsa-miR-378a-3p, hsa-miR-30a-5p, hsa-miR-34a-5, hsa-miR-99a-5p, hsa-miR-192-5p, hsa-miR-365a-3p, hsa-miR-22-5p, hsa-miR-505-3p, hsa-miR-320d, hsa-miR-215-5p, hsa-miR-122-5p, hsa-miR-194-5p, hsa-miR-885-5p, and hsa-miR-107.

In some embodiments, the one or more miRNAs are selected from the group consisting of hsa-miR-122-5p, hsa-miR-125b-5p, hsa-miR-365a-3p, hsa-miR-192-5p, hsa-miR-215-5p, hsa-miR-885-5p, hsa-miR-505-3p, hsa-miR-194-5p, hsa-miR-99a-5p, hsa-miR-34a-5p, hsa-miR-378a-3p.

In some embodiments, the one or more miRNAs are selected from the group consisting of hsa-miR-29a-3p, hsa-miR-146a-5p, hsa-miR-125b-5p, and hsa-miR-150-5p. In some embodiments, the one or more miRNAs include hsa-miR-29a-3p, hsa-miR-146a-5p, hsa-miR-125b-5p, and hsa-miR-150-5p.

In some embodiments, the one or more miRNAs are selected from the group consisting of hsa-miR-222-3p, hsa-miR-10b-5p, hsa-miR-139-5p, and hsa-miR-8743-p. In some embodiments, the one or more miRNAs include hsa-miR-222-3p, hsa-miR-10b-5p, hsa-miR-139-5p, and hsa-miR-8743-p.

In some embodiments, the one or more miRNAs comprise one or more miRNAs selected from the group consisting of hsa-miR-146a-5p, hsa-miR-146b-5p, hsa-miR-151a-5p, hsa-miR-223-3p, hsa-miR-590-5p, hsa-miR-155-5p, and hsa-miR-222-3p.

In some embodiments, the one or more miRNAs comprise hsa-miR-29a-3p, hsa-miR-125b-5p, and hsa-miR-150-5p.

In some embodiments, the one or more miRNAs comprise one or more miRNAs selected from the group consisting of hsa-miR-222-3p, hsa-miR-320d, hsa-miR-10b-5p, hsa-miR-139-5p, hsa-miR-143-3p, hsa-miR-338-3p, hsa-miR-326, hsa-miR-874-3p, hsa-miR-29b-3p, hsa-let-7i-5p, hsa-miR-30a-5p, hsa-miR-320c, hsa-miR-342-3p, hsa-miR-192-5p, hsa-miR-29c-3p, hsa-miR-32-5p, hsa-miR-185-5p, hsa-miR-324-3p, hsa-miR-375, and hsa-miR-93-5p.

In some embodiments, the method further comprising performing a magnetic resonance elastography (MRE) on the human prior to the administering step. In some embodiments, the human has been identified as having a liver disease or condition by MRE prior to the administering step.

In embodiments, the change in the levels of the one or more miRNAs is an increase in the level of a first miRNA among the one or more miRNAs or a decrease in the level of a second miRNA among the one or more miRNAs or both.

In embodiments, the increase in the level of the first miRNA among the one or more miRNAs is between 1-fold and 3-fold (e.g., 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3-fold) and the decrease in the level of the second miRNA among the one or more miRNAs is between 0.4-fold and 0.6-fold (e.g., 0.4, 0.5, 0.6-fold).

In embodiments, the change includes an increase in the level of the first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, and hsa-miR-378 in the second sample compared to the first sample or in the first sample compared to the control levels; and/or a decrease in the level of the second miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, and hsa-miR-127-3p in the second sample compared to the first sample or in the first sample compared to the control levels.

In embodiments, the change includes an increase in the level of the first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, and hsa-miR-18b in the second sample compared to the first sample or in the first sample compared to the control levels; and/or a decrease in the level of the second miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, and hsa-miR-324-3p in the second sample compared to the first sample or in the first sample compared to the control levels.

In embodiments, the change includes an increase in the level of the first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, and hsa-miR-424 in the second sample compared to the first sample or in the first sample compared to the control sample; and/or a decrease in the level of the second miRNA selected from the group consisting of hsa-miR-483-3p, hsa-miR-499-3p, hsa-miR-181d, hsa-miR-124, hsa-miR-125b, hsa-miR-34a, hsa-miR- 362-5p, hsa-miR-512-3p, hsa-miR-485-3p, and hsa-miR-132 in the second sample compared to the first sample or in the first sample compared to the control levels.

In embodiments, the change includes an increase in the level of the first miRNA selected from the group consisting of hsa-miR-125b-5p, hsa-miR-29a-3p, hsa-miR-150-5p, hsa-miR-30a-5p, hsa-miR-34a-5p, hsa-miR-29c-3p, hsa-miR-378a-3p, hsa-miR-99a-5p, and hsa-miR-375 or in the first sample compared to the control sample; and/or a decrease in the level of the second miRNA comprising hsa-miR-136-5p or in the first sample compared to the control levels.

V. Methods of Monitoring a Liver Disease or Condition

Also provided herein are methods of monitoring a liver disease or condition in a human. In some embodiments, a method of monitoring a liver disease or condition in a human, the method comprising detecting levels of one or more microRNAs (miRNAs) in the human. In some embodiments, provided is a method of monitoring a liver disease or condition in a human, the method comprising detecting levels of one or more microRNAs (miRNAs) in the human, wherein the levels of one or more miRNAs are correlated with a liver disease or condition. In some embodiments, the liver disease or condition is liver fibrosis, nonalcoholic steatohepatitis (NASH), non-alcoholic fatty liver disease (NAFLD) and/or liver inflammation.

In some embodiments, provided is a method of monitoring a liver disease or condition in a human, the method comprising detecting levels of one or more microRNAs (miRNAs) in a first sample obtained from the human, wherein one or more of the levels of one or more miRNAs in the first sample are correlated with a liver disease or condition and the one or more miRNAs are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, hsa-miR-127-3p, hsa-miR-136-5p, hsa-miR-30a-5p, hsa-miR-29c-3p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-222-3p, hsa-miR-365a-3p, hsa-miR-22-5p, hsa-miR-505-3p, hsa-miR-885-5p, hsa-miR-107, hsa-miR-100-5p, hsa-miR-155-5p, and hsa-miR-874-3p.

In some embodiments, the monitoring comprises determining regression, progression, or onset of the liver disease or condition. In some embodiments, the monitoring is performed by comparing one or more of the levels of one or more miRNAs in the second sample to the levels of the one or more miRNAs in the first sample.

In some embodiments, the one or more miRNAs are selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, hsa-miR-375, hsa-miR-1260b, hsa-miR-365a-3p, hsa-miR-215-5p, hsa-miR-194-5p, hsa-let-7i-5p, hsa-miR-122-5p, hsa-miR-192-5p, hsa-miR-222-3p, hsa-miR-378a-3p, hsa-miR-30a-5p, hsa-miR-365a-3p, hsa-miR-22-5p, hsa-miR-505-3p, hsa-miR-320d, hsa-miR-885-5p, hsa-miR-107, hsa-miR-100-5p, hsa-miR-148a-3p, hsa-miR-155-5p, hsa-miR-146a-5p, hsa-miR-125b-5p, hsa-miR-139-5p, hsa-miR-874-3p, and hsa-miR-10b-5p.

In some embodiments, the one or more miRNAs are selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, and hsa-miR-375.

In some embodiments, the one or more miRNAs comprise hsa-miR-34a-5p; and at least one miRNA selected from the group consisting of hsa-miR-125b-5p, hsa-miR-29a-3p, hsamiR-150-5p, hsa-miR-136-5p, hsa-miR-30a-5p, hsa-miR-34a-5p, hsa-miR-29c-3p, hsa-miR-378a-3p, hsa-miR-99a-5p, and hsa-miR-375.

In some embodiments, at least one miRNA is selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, and hsa-miR-375.

In some embodiments, the one or more miRNAs comprise hsa-miR-1260b; and optionally at least one miRNA selected from the group consisting of hsa-miR-125b-5p, hsa-miR-34a-5p, hsa-miR-378a-3p, hsa-miR-99a-5p, hsa-miR-365a-3p, hsa-miR-215-5p, hsa-miR-194-5p, let-7i-5p, hsa-miR-122-5p, hsa-miR-192-5p and hsa-miR-222-3p.

In some embodiments, the one or more miRNAs are selected from the group consisting of hsa-miR-125b-5p, hsa-miR-29a-3p, hsa-miR-378a-3p, hsa-miR-30a-5p, hsa-miR-34a-5, hsa-miR-99a-5p, hsa-miR-192-5p, hsa-miR-365a-3p, hsa-miR-22-5p, hsa-miR-505-3p, hsa-miR-320d, hsa-miR-215-5p, hsa-miR-122-5p, hsa-miR-194-5p, hsa-miR-885-5p, and hsa-miR-107.

In some embodiments, the one or more miRNAs are selected from the group consisting of hsa-miR-122-5p, hsa-miR-125b-5p, hsa-miR-365a-3p, hsa-miR-192-5p, hsa-miR-215-5p, hsa-miR-885-5p, hsa-miR-505-3p, hsa-miR-194-5p, hsa-miR-99a-5p, hsa-miR-34a-5p, hsa-miR-378a-3p.

In some embodiments, the one or more miRNAs are selected from the group consisting of hsa-miR-29a-3p, hsa-miR-146a-5p, hsa-miR-125b-5p, and hsa-miR-150-5p. In some embodiments, the one or more miRNAs comprise hsa-miR-29a-3p, hsa-miR-146a-5p, hsa-miR-125b-5p, and hsa-miR-150-5p.

In some embodiments, the one or more miRNAs are selected from the group consisting of hsa-miR-222-3p, hsa-miR-10b-5p, hsa-miR-139-5p, and hsa-miR-8743-p. In some embodiments, the one or more miRNAs comprise hsa-miR-222-3p, hsa-miR-10b-5p, hsa-miR-139-5p, and hsa-miR-8743-p.

In some embodiments, the one or more miRNAs comprise one or more miRNAs selected from the group consisting of hsa-miR-146a-5p, hsa-miR-146b-5p, hsa-miR-151a-5p, hsa-miR-223-3p, hsa-miR-590-5p, hsa-miR-155-5p, and hsa-miR-222-3p.

In some embodiments, the one or more miRNAs comprise hsa-miR-29a-3p, hsa-miR-125b-5p, and hsa-miR-150-5p.

In some embodiments, the one or more miRNAs comprise one or more miRNAs selected from the group consisting of hsa-miR-222-3p, hsa-miR-320d, hsa-miR-10b-5p, hsa-miR-139-5p, hsa-miR-143-3p, hsa-miR-338-3p, hsa-miR-326, hsa-miR-874-3p, hsa-miR-29b-3p, hsa-let-7i-5p, hsa-miR-30a-5p, hsa-miR-320c, hsa-miR-342-3p, hsa-miR-192-5p, hsa-miR-29c-3p, hsa-miR-32-5p, hsa-miR-185-5p, hsa-miR-324-3p, hsa-miR-375, and hsa-miR-93-5p.

In some embodiments, the method of monitoring further includes performing a magnetic resonance elastography (MRE) on the human in combination with the detecting step.

In some embodiments, the method further comprises administering one or more therapeutic agents to the human.

In some embodiments, a change in one or more of the levels of one or more miRNAs in the second sample compared to the levels of the one or more miRNAs in the first sample is correlated with a change in liver disease or condition.

In some embodiments, the first sample is obtained from the human prior to the second sample from the human. In some embodiments, the first sample is obtained from the human 12 hours, 24 hours, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 1 month, 2 months, 3 months, 4 months, 5 months, 6 months, 7 months, 8 months, 9 months, 10 months, 11 months, 12 months, 1 year, 2 years, 3 years, 4 years, or 5 years prior to the second sample obtained from the human. In some embodiments, the first sample is obtained from the human prior to administering one or more therapeutic agents to the human and the second sample is obtained from the human after administering one or more therapeutic agents to the human.

In some embodiments, the method of monitoring comprises detecting levels of the one or more miRNAs in a first sample obtained from the human, and comparing one or more of the levels of the one or more miRNAs in the first sample to the control levels of the one or more miRNAs, wherein a change in the levels of the one or more miRNAs in the first sample compared to the control levels of the one or more miRNAs is correlated with a liver disease or condition. In embodiments, the control levels of the one or more miRNAs are the levels of the one or more miRNAs in one or more control samples.

In some embodiments, provided is a method of monitoring a liver disease or condition in a human, the method comprising (a) detecting levels of one or more miRNAs in a first sample obtained from the human, (b) optionally administering one or more therapeutic agents to the human, and (c) detecting levels of one or more miRNAs in a second sample obtained from the human; wherein a change in one or more of the levels of one or more miRNAs in the second sample compared to the levels of one or more miRNAs in the first sample is correlated with a change in a liver disease or condition (i.e., effectiveness of the one or more therapeutic agents administered), wherein the one or more miRNAs are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsamiR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, hsa-miR-127-3p, hsa-miR-136-5p, hsa-miR-30a-5p, hsa-miR-29c-3p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-222-3p, hsa-miR-365a-3p, hsa-miR-22-5p, hsa-miR-505-3p, hsa-miR-885-5p, hsa-miR-107, hsa-miR-100-5p, hsa-miR-155-5p, and hsa-miR-874-3p.

In some embodiments, the one or more miRNAs are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, and hsa-miR-324-3p.

In some embodiments, the one or more miRNAs are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132.

In some embodiments, the change in the levels of the one or more miRNAs is an increase in the level of a first miRNA among the one or more miRNAs or a decrease in the level of a second miRNA among the one or more miRNAs, or both.

In some embodiments, an increase in the level of miRNA in the first sample compared to the control level is correlated to a liver disease or condition in a human. In some embodiments, a decrease in the level of miRNA in the first sample compared to the control level is correlated to a liver disease or condition in a human. In some embodiments, an increase in the level of miRNA in the second sample compared to that of the first sample is correlated to a change in a liver disease or condition in a human. In some embodiments, a decrease in the level of miRNA in the second sample compared to that of the first sample is correlated to a change in a liver disease or condition in a human. In some embodiments, an increase in the level of a first miRNA in the second sample compared to that of the first sample and a decrease in the level of a second miRNA in the second sample compared to that of the first sample is correlated to a change in a liver disease or condition in a human.

In some embodiments, an increase in the level of miRNA of at least a 1-fold change is correlated to a change in a liver disease or condition in a human. In some embodiments, an increase in the level of miRNA of at least a 2-fold change is correlated to a change in a liver disease or condition in a human. In some embodiments, an increase in the level of miRNA of at least a 3-fold change is correlated to a change in a liver disease or condition in a human.

In some embodiments, a decrease in the level of miRNA of at least a 0.6-fold change is correlated to a change in a liver disease or condition in a human. In some embodiments, a decrease in the level of miRNA of at least a 0.5-fold change is correlated to a change in a liver disease or condition in a human. In some embodiments, a decrease in the level of miRNA of at least a 0.4-fold change is correlated to a change in a liver disease or condition in a human.

In some embodiments, an increase in the level of a first miRNA of at least a 1-fold change and a decrease in the level of a second miRNA of at least a 0.6-fold change is correlated to a change in a liver disease or condition in a human. In some embodiments, an increase in the level of a first miRNA of at least a 2-fold change and a decrease in the level of a second miRNA of at least a 0.5-fold change is correlated to a change in a liver disease or condition in a human. In some embodiments, an increase in the level of a first miRNA of at least a 3-fold change and a decrease in the level of a second miRNA of at least a 0.4-fold change is correlated to a change in a liver disease or condition in a human.

In some embodiments, provided is a method of monitoring a liver disease or condition in a human, the method comprising (a) detecting levels of one or more miRNAs in a first sample obtained from the human, (b) optionally administering one or more therapeutic agents to the human, and (c) detecting levels of the one or more miRNAs in a second sample obtained from the human; wherein an increase in one or more of the levels of one or more miRNAs in the second sample compared to the levels of one or more miRNAs in the first sample is correlated with a change in a liver disease or condition, wherein the one or more miRNAs are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, and hsa-miR-378.

In some embodiments, provided is a method of monitoring a liver disease or condition in a human, the method comprising (a) detecting levels of one or more miRNAs in a first sample obtained from the human, (b) optionally administering one or more therapeutic agents to the human, and (c) detecting levels of the one or more miRNAs in a second sample obtained from the human; wherein a decrease in one or more of the levels of one or more miRNAs in the second sample compared to the levels of one or more miRNAs in the first sample is correlated with a change in a liver disease or condition, wherein the one or more miRNAs are selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-28-5p, hsa-miR-370, hsa-miR-34c-3p, hsa-miR-181b, hsa-miR-493, hsamiR-10a, hsa-miR-10b, hsa-miR-139-5p, hsa-miR-326, hsa-miR-423-3p, hsa-miR-187, and hsa-miR-127-3p.

In some embodiments, provided is a method of monitoring a liver disease or condition in a human, the method comprising (a) detecting levels of one or more miRNAs in a first sample obtained from the human, (b) optionally administering one or more therapeutic agents to the human, and (c) detecting levels of the one or more miRNAs in a second sample obtained from the human; wherein a change in one or more of the levels of one or more miRNAs in the second sample compared to the levels of one or more miRNAs in the first sample is correlated with a change in a liver disease or condition, wherein the change in the levels of one or more miRNAs comprise an increase of the level of the first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, and hsa-miR-378 in the second sample compared to the first sample and/or a decrease of the level of the second miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-28-5p, hsa-miR-370, hsa-miR-34c-3p, hsa-miR-18b, hsa-miR-493, hsa-miR-10a, hsa-miR-10b, hsa-miR-139-5p, hsa-miR-326, hsa-miR-423-3p, hsa-miR-187, and hsa-miR-127-3p in the second sample compared to the first sample.

In some embodiments, the change in the levels of one or more miRNAs comprise an increase of the level of the first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, and hsa-miR-18b in the second sample compared to the first sample and a decrease of the level of the second miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, and hsa-miR-324-3p in the second sample compared to the first sample.

In some embodiments, the change in the levels of one or more miRNAs comprise an increase of the level of the first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, and hsa-miR-424 in the second sample compared to the first sample and/or a decrease of the level of the second miRNA miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132 in the second sample compared to the first sample.

In some embodiments, the change comprises an increase in the level of the first miRNA comprising hsa-miR-125b-5p, hsa-miR-29a-3p, hsa-miR-150-5p, hsa-miR-30a-5p, hsa-miR-34a-5p, hsa-miR-29c-3p, hsa-miR-378a-3p, hsa-miR-99a-5p, hsa-miR-375 or any combination thereof in the second sample compared to the first sample; and/or a decrease in the level of the second miRNA comprising hsa-miR-136-5p in the second sample compared to the first sample.

In some embodiments, an increase in the level of the first miRNA comprising hsa-miR-125b-5p, hsa-miR-29a-3p, hsa-miR-150-5p, hsa-miR-30a-5p, hsa-miR-34a-5p, hsa-miR-29c-3p, hsa-miR-378a-3p, hsa-miR-99a-5p, hsa-miR-375 or any combination thereof in the second sample compared to the first sample or in the first sample compared to the control level indicates the human has stage 3-4 liver fibrosis.

In some embodiments, a decrease in the level of the second miRNA comprising hsa-miR-136-5p in the second sample compared to the first sample or in the first sample compared to the control sample indicates the human has stage 3-4 liver fibrosis.

In some embodiments, the human is likely to receive liver transplant when diagnosed with stage 3-4 liver fibrosis.

In some embodiments, no change or a decrease in the level of the first miRNA comprising hsa-miR-125b-5p, hsa-miR-29a-3p, hsa-miR-150-5p, hsa-miR-30a-5p, hsa-miR-34a-5p, hsa-miR-29c-3p, hsa-miR-378a-3p, hsa-miR-99a-5p, hsa-miR-375 or any combination thereof in the second sample compared to the first sample or in the first sample compared to the control level indicates the human has stage 1-2 liver fibrosis.

In some embodiments, no change or an increase in the level of the second miRNA comprising hsa-miR-136-5p in the second sample compared to the first sample or in the first sample compared to the control level indicates the human has stage 1-2 liver fibrosis.

In some embodiments, the human is likely to change lifestyle when diagnosed with stage 1-2 liver fibrosis. Lifestyle changes include, but are not limited to, dietary modifications (e.g., caloric restriction, carbohydrate restriction, and/or fat restriction) and increased physical activity.

In some embodiments, an increase in the levels of one or more miRNAs selected from the group consisting of hsa-miR-125b-5p, hsa-miR-34a-5p, hsa-miR-378a-3p, hsa-miR-99a-5p, hsa-miR-365a-3p, hsa-miR-215-5p, hsa-miR-194-5p, hsa-miR-122-5p, and hsa-miR-192-5p indicates a progression (i.e., worsening) in fibrosis stage. In some embodiments, a decrease in the levels of one or more miRNAs selected from the group consisting of hsa-miR-1260b, hsa-let-7i-5p, and hsa-miR-222-3p indicates a progression in fibrosis stage. A skilled practitioner or physician in the field would adjust the treatment regimen (e.g., therapeutic agent) for such patients.

In some embodiments, a decrease in the levels of one or more miRNAs selected from the group consisting of hsa-miR-125b-5p, hsa-miR-34a-5p, hsa-miR-378a-3p, hsa-miR-99a-5p, hsa-miR-365a-3p, hsa-miR-215-5p, hsa-miR-194-5p, hsa-miR-122-5p, and hsa-miR-192-5p indicates a regression (i.e., improvement) in fibrosis stage. In some embodiments, an increase in the levels of one or more miRNAs selected from the group consisting of hsa-miR-1260b, hsa-let-7i-5p, and hsa-miR-222-3p indicates a regression in fibrosis stage. A skilled practitioner or physician in the field would adjust the treatment regimen (e.g., therapeutic agent) for such patients.

In some embodiments, provided is a method of monitoring a liver disease or condition in a human, the method comprising (a) detecting levels of one or more miRNAs in a first sample obtained from the human, (b) optionally administering one or more therapeutic agents to the human, and (c) detecting levels of one or more miRNAs in a second sample obtained from the human; wherein a change in one or more of the levels of one or more miRNAs in the second sample compared to the levels of one or more miRNAs in the first sample is correlated with a change in a liver disease or condition, wherein the change in the levels of one or more miRNAs comprise an increase of the level of the first miRNA comprising hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424 or any combination thereof in the second sample compared to the first sample and/or a decrease of the level of the second miRNA comprising hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132 or any combination thereof in the second sample compared to the first sample.

VI. Methods of Administering Therapeutic Agents

In some embodiments, provided is a method of treating a human in need thereof, comprising (a) detecting of the levels of one or more miRNAs and (b) administering one or more therapeutic agents to the human; wherein one or more miRNAs are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132, wherein the levels of one or more miRNAs determine the one or more therapeutic agents.

VII. Methods of Detecting

Further provided herein are methods of detecting the levels of one or more miRNAs. The methods include detecting levels of one or more miRNAs in a first sample from a human, wherein the one or more miRNAs are selected from any miRNA panel described herein.

In some embodiments, the one or more miRNAs are selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, hsa-miR-127-3p, hsa-miR-136-5p, hsa-miR-30a-5p, hsa-miR-29c-3p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-222-3p, hsa-miR-365a-3p, hsa-miR-22-5p, hsa-miR-505-3p, hsa-miR-885-5p, hsa-miR-107, hsa-miR-100-5p, hsa-miR-155-5p, hsa-miR-874-3p.

In some embodiments, the one or more miRNAs are selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, hsa-miR-375, hsa-miR-1260b, hsa-miR-365a-3p, hsa-miR-215-5p, hsa-miR-194-5p, hsa-let-7i-5p, hsa-miR-122-5p, hsa-miR-192-5p, hsa-miR-222-3p, hsa-miR-378a-3p, hsa-miR-30a-5p, hsa-miR-365a-3p, hsa-miR-22-5p, hsa-miR-505-3p, hsa-miR-320d, hsa-miR-885-5p, hsa-miR-107, hsa-miR-100-5p, hsa-miR-148a-3p, hsa-miR-155-5p, hsa-miR-146a-5p, hsa-miR-125b-5p, hsa-miR-139-5p, hsa-miR-874-3p, and hsa-miR-10b-5p.

In some embodiments, the one or more miRNAs are selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, and hsa-miR-375.

In some embodiments, the one or more miRNAs comprise hsa-miR-34a-5p; and at least one miRNA selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, and hsa-miR-375.

In some embodiments, the one or more miRNAs are selected from the group consisting of hsa-miR-125b-5p, hsa-miR-34a-5p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-122-5p, hsa-miR-192-5p and hsa-miR-222-3p.

In some embodiments, the one or more miRNAs comprise hsa-miR-1260b; and optionally at least one miRNA selected from the group consisting of hsa-miR-125b-5p, hsa-miR-34a-5p, hsa-miR-378a-3p, hsa-miR-99a-5p, hsa-miR-365a-3p, hsa-miR-215-5p, hsa-miR-194-5p, hsa-let-7i-5p, hsa-miR-122-5p, hsa-miR-192-5p and hsa-miR-222-3p.

In some embodiments, the one or more miRNAs are selected from the group consisting of hsa-miR-125b-5p, hsa-miR-29a-3p, hsa-miR-378a-3p, hsa-miR-30a-5p, hsamiR-34a-5, hsa-miR-99a-5p, hsa-miR-192-5p, hsa-miR-365a-3p, hsa-miR-22-5p, hsa-miR-505-3p, hsa-miR-320d, hsa-miR-215-5p, hsa-miR-122-5p, hsa-miR-194-5p, hsa-miR-885-5p, and hsa-miR-107.

In some embodiments, the one or more miRNAs are selected from the group consisting of hsa-miR-122-5p, hsa-miR-125b-5p, hsa-miR-365a-3p, hsa-miR-192-5p, hsa-miR-215-5p, hsa-miR-885-5p, hsa-miR-505-3p, hsa-miR-194-5p, hsa-miR-99a-5p, hsa-miR-34a-5p, hsa-miR-378a-3p.

In some embodiments, the one or more miRNAs are selected from the group consisting of hsa-miR-29a-3p, hsa-miR-146a-5p, hsa-miR-125b-5p, and hsa-miR-150-5p.

In some embodiments, the one or more miRNAs are selected from the group consisting of hsa-miR-222-3p, hsa-miR-10b-5p, hsa-miR-139-5p, and hsa-miR-8743-p.

In some embodiments, the one or more miRNAs comprise one or more miRNAs selected from the group consisting of hsa-miR-146a-5p, hsa-miR-146b-5p, hsa-miR-151a-5p, hsa-miR-223-3p, hsa-miR-590-5p, hsa-miR-155-5p, and hsa-miR-222-3p.

In some embodiments, the one or more miRNAs comprise hsa-miR-29a-3p, hsa-miR-125b-5p, and hsa-miR-150-5p.

In some embodiments, the one or more miRNAs comprise one or more miRNAs selected from the group consisting of hsa-miR-222-3p, hsa-miR-320d, hsa-miR-10b-5p, hsa-miR-139-5p, hsa-miR-143-3p, hsa-miR-338-3p, hsa-miR-326, hsa-miR-874-3p, hsa-miR-29b-3p, hsa-let-7i-5p, hsa-miR-30a-5p, hsa-miR-320c, hsa-miR-342-3p, hsa-miR-192-5p, hsa-miR-29c-3p, hsa-miR-32-5p, hsa-miR-185-5p, hsa-miR-324-3p, hsa-miR-375, and hsa-miR-93-5p.

In some embodiments, the methods of detecting further include performing a magnetic resonance elastography (MRE) on the human.

In some embodiments, the human has a liver disease or condition, is suspected of having a liver disease or condition, or has a risk for a liver disease or condition. In some embodiments, the liver disease or condition is liver fibrosis, nonalcoholic steatohepatitis (NASH), non-alcoholic fatty liver disease (NAFLD) and/or liver inflammation.

In some embodiments, the liver disease or condition is liver fibrosis. In some embodiments, the liver disease or condition is stage 3 or stage 4 (F3-4) liver fibrosis. In some embodiments, the stage of the liver fibrosis is not determined. In some embodiments, the liver disease or condition is nonalcoholic steatohepatitis (NASH). In some embodiments, the liver disease or condition is nonalcoholic fatty liver disease (NAFLD). In some embodiments, the liver disease or condition is liver inflammation. In some embodiments, the human has a NAFLD Activity Score (NAS) of 5 or above. In some embodiments, the human has three or more features of metabolic syndrome, wherein the metabolic syndrome comprises elevated blood pressure, abdominal obesity, elevated fasting plasma glucose, high serum triglycerides, low high-density lipoprotein cholesterol or any combination thereof. In some embodiments, the human has a serum alanine aminotransferase (ALT) level between 1.5-fold to 5-fold of upper limit of normal (ULN). In some embodiments, the human has a serum alanine aminotransferase (ALT) level between 1.5-fold to 5-fold of upper limit of normal (ULN). In some embodiments, the human has a liver stiffness by FibroScan (Echosens®, Paris, France) of between 7 kPa and 12 kPa.

In some embodiments, the methods of detecting further include o detecting levels of the one or more miRNAs from a second sample obtained from the human, and detecting a change in one or more of the levels of the one or more miRNAs in the second sample compared to the levels of the one or more miRNAs in the first sample. In some embodiments, the first sample is obtained from the human prior to the second sample from the human. In some embodiments, the first sample is obtained from the human 12 hours, 24 hours, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 1 month, 2 months, 3 months, 4 months, 5 months, 6 months, 7 months, 8 months, 9 months, 10 months, 11 months, 12 months, 1 year, 2 years, 3 years, 4 years, or 5 years prior to the second sample obtained from the human. In some embodiments, the first sample is obtained from the human prior to administering one or more therapeutic agents to the human and the second sample is obtained from the human after administering one or more therapeutic agents to the human.

In some embodiments, the methods of detecting further include detecting a change in one or more of the levels of the one or more miRNAs in the first sample compared to the control levels of the one or more miRNAs. In some embodiments, the control levels of the one or more miRNAs are the levels of the one or more miRNAs in one or more control samples.

In some embodiments, the change in the levels of the one or more miRNAs is an increase in the level of a first miRNA among the one or more miRNAs or a decrease in the level of a second miRNA among the one or more miRNAs or both.

In some embodiments, the increase in the level of the first miRNA among the one or more miRNAs is between 1-fold and 3-fold (e.g., 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3-fold) and/or the decrease in the level of the second miRNA among the one or more miRNAs is between 0.4-fold and 0.6-fold (e.g., 0.4, 0.5, 0.6-fold).

In some embodiments, an increase in the level of miRNA in the first sample compared to that of the control level is correlated to a liver disease or condition in a human. In some embodiments, a decrease in the level of miRNA in the first sample compared to that of the control level is correlated to a liver disease or condition in a human. In some embodiments, an increase in the level of miRNA in the second sample compared to that of the first sample is correlated to a liver disease or condition in a human. In some embodiments, a decrease in the level of miRNA in the second sample compared to that of the first sample is correlated to a liver disease or condition in a human. In some embodiments, an increase in the level of a first miRNA in the second sample compared to that of the first sample and a decrease in the level of a second miRNA in the second sample compared to that of the first sample is correlated to a liver disease or condition in a human.

In some embodiments, an increase in the level of miRNA of at least a 1-fold change is correlated to a liver disease or condition in a human. In some embodiments, an increase in the level of miRNA of at least a 2-fold change is correlated to a liver disease or condition in a human. In some embodiments, an increase in the level of miRNA of at least a 3-fold change is correlated to a liver disease or condition in a human.

In some embodiments, a decrease in the level of miRNA of at least a 0.6-fold change is correlated to a liver disease or condition in a human. In some embodiments, a decrease in the level of miRNA of at least a 0.5-fold change is correlated to a liver disease or condition in a human. In some embodiments, a decrease in the level of miRNA of at least a 0.4-fold change is correlated to a liver disease or condition in a human.

In some embodiments, at least a 1-fold change and a decrease in the level of a second miRNA of at least a 0.6-fold change is correlated to a liver disease or condition in a human. In some embodiments, an increase in the level of a first miRNA of at least a 2-fold change and a decrease in the level of a second miRNA of at least a 0.5-fold change is correlated to a liver disease or condition in a human. In some embodiments, an increase in the level of a first miRNA of at least a 3-fold change and a decrease in the level of a second miRNA f of at least a 0.4-fold change is correlated to a liver disease or condition in a human.

In some embodiments, the change includes an increase in the level of the first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, and hsa-miR-18b in the second sample compared to the first sample or in the first sample compared to the control level; and/or a decrease in the level of the second miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, and hsa-miR-324-3p in the second sample compared to the first sample or in the first sample compared to the control level.

In some embodiments, the change includes an increase in the level of the first miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, and hsa-miR-424 in the second sample compared to the first sample or in the first sample compared to the control level; and/or a decrease in the level of the second miRNA selected from the group consisting of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132 in the second sample compared to the first sample or in the first sample compared to the control level.

In some embodiments, the change includes an increase in the level of the first miRNA selected from the group consisting of hsa-miR-15b, hsa-miR-17, hsa-miR-451, hsa-miR-15a, and has-miR-19b in the second sample compared to the first sample or in the first sample compared to the control level; and/or a decrease in the level of the second miRNA selected from the group consisting of hsa-miR-483-3p, hsa-miR-499-3p, hsa-miR-181d, hsa-miR-124, and hsa-miR-34a in the second sample compared to the first sample or in the first sample compared to the control level.

In some embodiments, the change includes an increase in the level of the first miRNA selected from the group consisting of hsa-miR-125b-5p, hsa-miR-29a-3p, hsa-miR-150-5p, hsa-miR-30a-5p, hsa-miR-34a-5p, hsa-miR-29c-3p, hsa-miR-378a-3p, hsa-miR-99a-5p, and hsa-miR-375 in the second sample compared to the first sample or in the first sample compared to the control level; and/or a decrease in the level of the second miRNA comprising hsa-miR-136-5p in the second sample compared to the first sample or in the first sample compared to the control level.

VIII. microRNA (miRNA)

In some embodiments, the microRNA (miRNA) is a panel of miRNAs comprising any one or more miRNAs selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, hsa-miR-127-3p, hsa-miR-136-5p, hsa-miR-30a-5p, hsa-miR-29c-3p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-222-3p, hsa-miR-365a-3p, hsa-miR-22-5p, hsa-miR-505-3p, hsa-miR-885-5p, hsa-miR-107, hsa-miR-100-5p, hsa-miR-155-5p, and hsa-miR-874-3p.

In some embodiments, the miRNAs detected or identified in any method described herein includes any 1-116 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, or 116) miRNAs selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, hsa-miR-127-3p, hsa-miR-136-5p, hsa-miR-30a-5p, hsa-miR-29c-3p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-222-3p, hsa-miR-365a-3p, hsa-miR-22-5p, hsa-miR-505-3p, hsa-miR-885-5p, hsa-miR-107, hsa-miR-100-5p, hsa-miR-155-5p, and hsa-miR-874-3p.

In some embodiments, the miRNA detected/identified in any method described herein is a panel of any ten miRNAs selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, hsa-miR-127-3p, hsa-miR-136-5p, hsa-miR-30a-5p, hsa-miR-29c-3p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-222-3p, hsa-miR-365a-3p, hsa-miR-22-5p, hsa-miR-505-3p, hsa-miR-885-5p, hsa-miR-107, hsa-miR-100-5p, hsa-miR-155-5p, and hsa-miR-874-3p.

In some embodiments, the miRNA detected/identified in any method described herein is a panel of any twenty miRNAs selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, and hsa-miR-127-3p, hsa-miR-136-5p, hsa-miR-30a-5p, hsa-miR-29c-3p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-222-3p, hsa-miR-365a-3p, hsa-miR-22-5p, hsa-miR-505-3p, hsa-miR-885-5p, hsa-miR-107, hsa-miR-100-5p, hsa-miR-155-5p, and hsa-miR-874-3p.

In some embodiments, the miRNA detected/identified in any method described herein is a panel of miRNAs comprising any one or more miRNAs selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, and hsa-miR-324-3p.

In some embodiments, the microRNA (miRNA) detected/identified in any method described herein is a panel of miRNAs comprising 1-60 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60) miRNAs selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR- 539, hsa-miR-320d, hsa-miR-523, hsa-miR-28-3p, hsa-miR-219-1-3p, hsa-miR-323-5p, hsa-miR-339-3p, and hsa-miR-324-3p.

In some embodiments, the miRNA detected/identified in any method described herein is a panel of any ten miRNAs selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, and hsa-miR-324-3p.

In some embodiments, the miRNA detected/identified in any method described herein is a panel of any twenty miRNAs selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, and hsa-miR-324-3p.

In some embodiments, the miRNA detected/identified in any method described herein is a panel of miRNA comprising any one or more miRNAs selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132.

In some embodiments, the miRNA detected/identified in any method described herein is a panel of miRNAs comprising any 1-30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) miRNAs selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132.

In some embodiments, the miRNA detected/identified in any method described herein is a panel of any ten miRNAs selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132.

In some embodiments, the miRNA detected/identified in any method described herein is a panel of any twenty miRNAs selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132.

In some embodiments, the miRNA detected/identified in any method described herein is a panel of miRNA comprising hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132.

In some embodiments, the miRNA detected/identified in any method described herein includes one or more miRNAs selected from the group consisting of hsa-miR-15b, hsa-miR-17, hsa-miR-451, hsa-miR-15a, has-miR-19b, hsa-miR-483-3p, hsa-miR-499-3p, hsa-miR-181d, hsa-miR-124, and hsa-miR-34a.

In some embodiments, the miRNA detected/identified in any method described herein is a panel of any 1-10 (e.g., 1, 2, 3, 4, 5, 6, 7, 8, 9, or 10) miRNAs selected from the group consisting of hsa-miR-15b, hsa-miR-17, hsa-miR-451, hsa-miR-15a, has-miR-19b, hsa-miR-483-3p, hsa-miR-499-3p, hsa-miR-181d, hsa-miR-124, and hsa-miR-34a.

In some embodiments, the miRNA detected/identified in any method described herein comprising hsa-miR-15b, hsa-miR-17, hsa-miR-451, hsa-miR-15a, has-miR-19b, hsa-miR-483-3p, hsa-miR-499-3p, hsa-miR-181d, hsa-miR-124, and hsa-miR-34a.

In some embodiments, the miRNA detected/identified in any method described herein includes any 1-34 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34) miRNAs selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, hsa-miR-375, hsa-miR-1260b, hsa-miR-365a-3p, hsa-miR-215-5p, hsa-miR-194-5p, hsa-let-7i-5p, hsa-miR-122-5p, hsa-miR-192-5p, hsa-miR-222-3p, hsa-miR-378a-3p, hsa-miR-30a-5p, hsa-miR-365a-3p, hsa-miR-22-5p, hsa-miR-505-3p, hsa-miR-320d, hsa-miR-885-5p, hsa-miR-107, hsa-miR-100-5p, hsa-miR-148a-3p, hsa-miR-155-5p, hsa-miR-146a-5p, hsa-miR-125b-5p, hsa-miR-139-5p, hsa-miR-874-3p, and hsa-miR-10b-5p.

In some embodiments, the miRNA detected/identified in any method described herein includes a panel of 5 miRNAs selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, hsa-miR-375, hsa-miR-1260b, hsa-miR-365a-3p, hsa-miR-215-5p, hsa-miR-194-5p, hsalet-7i-5p, hsa-miR-122-5p, hsa-miR-192-5p, hsa-miR-222-3p, hsa-miR-378a-3p, hsa-miR-30a-5p, hsa-miR-365a-3p, hsa-miR-22-5p, hsa-miR-505-3p, hsa-miR-320d, hsa-miR-885-5p, hsa-miR-107, hsa-miR-100-5p, hsa-miR-148a-3p, hsa-miR-155-5p, hsa-miR-146a-5p, hsa-miR-125b-5p, hsa-miR-139-5p, hsa-miR-874-3p, and hsa-miR-10b-5p.

In some embodiments, the miRNA detected/identified in any method described herein includes a panel of 10 miRNAs selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, hsa-miR-375, hsa-miR-1260b, hsa-miR-365a-3p, hsa-miR-215-5p, hsa-miR-194-5p, hsa-let-7i-5p, hsa-miR-122-5p, hsa-miR-192-5p, hsa-miR-222-3p, hsa-miR-378a-3p, hsa-miR-30a-5p, hsa-miR-365a-3p, hsa-miR-22-5p, hsa-miR-505-3p, hsa-miR-320d, hsa-miR-885-5p, hsa-miR-107, hsa-miR-100-5p, hsa-miR-148a-3p, hsa-miR-155-5p, hsa-miR-146a-5p, hsa-miR-125b-5p, hsa-miR-139-5p, hsa-miR-874-3p, and hsa-miR-10b-5p.

In some embodiments, the miRNA detected/identified in any method described herein includes a panel of 20 miRNAs selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, hsa-miR-375, hsa-miR-1260b, hsa-miR-365a-3p, hsa-miR-215-5p, hsa-miR-194-5p, hsa-let-7i-5p, hsa-miR-122-5p, hsa-miR-192-5p, hsa-miR-222-3p, hsa-miR-378a-3p, hsa-miR-30a-5p, hsa-miR-365a-3p, hsa-miR-22-5p, hsa-miR-505-3p, hsa-miR-320d, hsa-miR-885-5p, hsa-miR-107, hsa-miR-100-5p, hsa-miR-148a-3p, hsa-miR-155-5p, hsa-miR-146a-5p, hsa-miR-125b-5p, hsa-miR-139-5p, hsa-miR-874-3p, and hsa-miR-10b-5p.

In some embodiments, the miRNA detected/identified in any method described herein includes at least one miRNA selected from the group consisting of hsa-miR-451, hsa-miR-124, and hsa-miR-34a; and/or at least one miRNA selected from the group consisting of hsa-miR-15b, hsa-miR-17, hsa-miR-15a, has-miR-19b, hsa-miR-483-3p, hsa-miR-499-3p, and hsa-miR-181d. In some embodiments, the miRNA may further includes at least one miRNA selected from the group consisting of hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-125b, hsa-miR-362-5p, hsa-miR-512-3p, hsa-miR-485-3p, hsa-miR-132, hsa-miR-92a, hsa-let-7b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, and hsa-miR-127-3p.

In some embodiments, the mRNA detected/identified in any method described herein includes one or more (e.g., 1, 2, 3, 4, 5, 6, 7, 8, 9, 10 or 11) miRNAs selected from the group consisting of hsa-miR-505-3p, hsa-miR-29a-3p, hsa-miR-215-5p, hsa-miR-148a-3p, hsa-miR-99a-5p, hsa-miR-885-5p, hsa-miR-122-5p, hsa-miR-34a-5p, hsa-miR-365a-3p, hsa-miR-194-5p, and hsa-miR-155-5p.

In some embodiments, the miRNA detected/identified in any method described herein includes one or more (e.g., 1, 2, 3, 4, 5, 6, 7, 8, 9, or 10) miRNAs selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, and hsa-miR-375.

In some embodiments, the miRNA detected/identified in any method described herein includes hsa-miR-34a-5p; and at least one miRNA selected from the group consisting of hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, and hsa-miR-375.

In some embodiments, the miRNA detected/identified in any method described herein includes hsa-miR-125b-5p, hsa-miR-34a-5p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-122-5p, hsa-miR-192-5p and hsa-miR-222-3p.

In some embodiments, the miRNA detected/identified in any method described herein includes hsa-miR-1260b; and optionally at least one miRNA selected from the group consisting of hsa-miR-125b-5p, hsa-miR-34a-5p, hsa-miR-378a-3p, hsa-miR-99a-5p, hsa-miR-365a-3p, hsa-miR-215-5p, hsa-miR-194-5p, hsa-let-7i-5p, hsa-miR-122-5p, hsa-miR-192-5p and hsa-miR-222-3p.

In some embodiments, the miRNA detected/identified in any method described herein includes one or more miRNAs selected from the group consisting of miR-125b-5p, hsa-miR-29a-3p, hsa-miR-378a-3p, hsa-miR-30a-5p, hsa-miR-34a-5, hsa-miR-99a-5p, hsa-miR-192-5p, hsa-miR-365a-3p, hsa-miR-22-5p, hsa-miR-505-3p, hsa-miR-320d, hsa-miR-215-5p, hsa-miR-122-5p, hsa-miR-194-5p, hsa-miR-885-5p, and hsa-miR-107.

In some embodiments, the miRNA detected/identified in any method described herein includes one or more miRNAs selected from the group consisting of hsa-miR-122-5p, hsa-miR-125b-5p, hsa-miR-365a-3p, hsa-miR-192-5p, hsa-miR-215-5p, hsa-miR-885-5p, hsa-miR-505-3p, hsa-miR-194-5p, hsa-miR-99a-5p, hsa-miR-34a-5p, and hsa-miR-378a-3p.

In some embodiments, the miRNA detected/identified in any method described herein includes one or more miRNAs selected from the group consisting of hsa-miR-29a-3p, hsa-miR-146a-5p, hsa-miR-125b-5p, and hsa-miR-150-5p. In some embodiments, the miRNA detected/identified in any method described herein includes hsa-miR-29a-3p, hsa-miR-146a-5p, hsa-miR-125b-5p, and hsa-miR-150-5p. In some embodiments, the miRNA detected/identified in any method described herein includes hsa-miR-29a-3p, hsa-miR-146a-5p, hsa-miR-125b-5p, and hsa-miR-150-5p; and optionally at least one miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, hsa-miR-127-3p, hsa-miR-136-5p, hsa-miR-30a-5p, hsa-miR-29c-3p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-222-3p, hsa-miR-365a-3p, hsa-miR-22-5p, hsa-miR-505-3p, hsa-miR-885-5p, hsa-miR-107, hsa-miR-100-5p, hsa-miR-155-5p, and hsa-miR-874-3p.

In some embodiments, the miRNA detected/identified in any method described herein includes one or more miRNAs selected from the group consisting of hsa-miR-222-3p, hsa-miR-10b-5p, hsa-miR-139-5p, and hsa-miR-8743-p. In some embodiments, the miRNA detected/identified in any method described herein includes hsa-miR-222-3p, hsa-miR-10b-5p, hsa-miR-139-5p, and hsa-miR-8743-p. In some embodiments, the miRNA detected/identified in any method described herein includes hsa-miR-222-3p, hsa-miR-10b-5p, hsa-miR-139-5p, and hsa-miR-8743-p; and optionally at least one miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, hsa-miR-127-3p, hsa-miR-136-5p, hsa-miR-30a-5p, hsa-miR-29c-3p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-222-3p, hsa-miR-365a-3p, hsa-miR-22-5p, hsa-miR-505-3p, hsa-miR-885-5p, hsa-miR-107, hsa-miR-100-5p, hsa-miR-155-5p, and hsa-miR-874-3p.

In some embodiments, the miRNA detected/identified in any method described herein includes one or more miRNAs selected from the group consisting of hsa-miR-146a-5p, hsa-miR-146b-5p, hsa-miR-151a-5p, hsa-miR-223-3p, hsa-miR-590-5p, hsa-miR-155-5p, and hsa-miR-222-3p. In some embodiments, the miRNA detected/identified in any method described herein includes hsa-miR-146a-5p, hsa-miR-146b-5p, hsa-miR-151a-5p, hsa-miR-223-3p, hsa-miR-590-5p, hsa-miR-155-5p, and hsa-miR-222-3p. In some embodiments, the miRNA detected/identified in any method described herein includes hsa-miR-146a-5p, hsa-miR-146b-5p, hsa-miR-151a-5p, hsa-miR-223-3p, hsa-miR-590-5p, hsa-miR-155-5p, and hsa-miR-222-3p; and optionally at least one miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, hsa-miR-127-3p, hsa-miR-136-5p, hsa-miR-30a-5p, hsa-miR-29c-3p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-222-3p, hsa-miR-365a-3p, hsa-miR-22-5p, hsa-miR-505-3p, hsa-miR-885-5p, hsa-miR-107, hsa-miR-100-5p, hsa-miR-155-5p, and hsa-miR-874-3p.

In some embodiments, the miRNA detected/identified in any method described herein includes one or more miRNAs selected from the group consisting of hsa-miR-29a-3p, hsa-miR-125b-5p, and hsa-miR-150-5p. In some embodiments, the miRNA detected/identified in any method described herein includes hsa-miR-29a-3p, hsa-miR-125b-5p, and hsa-miR-150-5p. In some embodiments, the miRNA detected/identified in any method described herein includes hsa-miR-29a-3p, hsa-miR-125b-5p, and hsa-miR-150-5p; and optionally at least one miRNA selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsamiR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, hsa-miR-127-3p, hsa-miR-136-5p, hsa-miR-30a-5p, hsa-miR-29c-3p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-222-3p, hsa-miR-365a-3p, hsa-miR-22-5p, hsa-miR-505-3p, hsa-miR-885-5p, hsa-miR-107, hsa-miR-100-5p, hsa-miR-155-5p, and hsa-miR-874-3p.

In some embodiments, the miRNA detected/identified in any method described herein includes one or more miRNAs selected from the group consisting of hsa-miR-222-3p, hsa-miR-320d, hsa-miR-10b-5p, hsa-miR-139-5p, hsa-miR-143-3p, hsa-miR-338-3p, hsa-miR-326, hsa-miR-874-3p, hsa-miR-29b-3p, hsa-let-7i-5p, hsa-miR-30a-5p, hsa-miR-320c, hsa-miR-342-3p, hsa-miR-192-5p, hsa-miR-29c-3p, hsa-miR-32-5p, hsa-miR-185-5p, hsa-miR-324-3p, hsa-miR-375, hsa-miR-93-5p.

In some embodiments, the miRNA detected/identified in any method described herein is a panel of miRNAs comprising hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132, wherein an increase in the level of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, and hsa-miR-424 in a second sample relative to a first sample indicates liver fibrotic regression.

In some embodiments, the microRNA (miRNA) detected/identified in any method described herein is a panel of miRNAs comprising hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132, wherein a decrease of the level of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132 in a second sample relative to a first sample indicates liver fibrotic regression.

In some embodiments, the microRNA (miRNA) detected/identified in any method described herein is a panel of miRNAs comprising hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132, wherein an increase in the level of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, and hsa-miR-424 and a decrease in the level of hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132 in a second sample relative to a first sample indicates liver fibrotic regression.

In some embodiments, the microRNA (miRNA) detected/identified in any method described herein is a panel of miRNAs comprising hsa-miR-125b-5p, hsa-miR-29a-3p, hsa-miR-150-5p, hsa-miR-30a-5p, hsa-miR-34a-5p, hsa-miR-29c-3p, hsa-miR-378a-3p, hsa-miR-99a-5p, hsa-miR-375 or any combination thereof. In some embodiments, an increase in the level of miRNA comprising hsa-miR-125b-5p, hsa-miR-29a-3p, hsa-miR-150-5p, hsa-miR-30a-5p, hsa-miR-34a-5p, hsa-miR-29c-3p, hsa-miR-378a-3p, hsa-miR-99a-5p, hsa-miR-375 or any combination thereof in the second sample compared to the first sample or in the first sample compared to the control sample indicates a stage 3-4 liver fibrosis. In some embodiments, no change or a decrease in the level of miRNA comprising hsa-miR-125b-5p, hsa-miR-29a-3p, hsa-miR-150-5p, hsa-miR-30a-5p, hsa-miR-34a-5p, hsa-miR-29c-3p, hsa-miR-378a-3p, hsa-miR-99a-5p, hsa-miR-375 or any combination thereof in the second sample compared to the first sample or in the first sample compared to the control sample indicates a stage 1-2 liver fibrosis.

In some embodiments, the microRNA (miRNA) detected/identified in any method described herein is a panel of miRNAs comprising hsa-miR-136-5p. In some embodiments, a decrease in the level of miRNA comprising hsa-miR-136-5p in the second sample compared to the first sample or in the first sample compared to the control sample indicates a stage 3-4 liver fibrosis. In some embodiments, no change or an increase in the level of miRNA comprising hsa-miR-136-5p in the second sample compared to the first sample or in the first sample compared to the control sample indicates a stage 1-2 liver fibrosis.

In some embodiments, the microRNA (miRNA) detected/identified in any method described herein is a panel of miRNAs comprising hsa-miR-125b-5p, hsa-miR-34a-5p, hsa-miR-378a-3p, hsa-miR-99a-5p, hsa-miR-365a-3p, hsa-miR-215-5p, hsa-miR-194-5p, hsa-miR-122-5p, hsa-miR-192-5p, hsa-miR-1260b, hsa-let-7i-5p, and hsa-miR-222-3p or any combination thereof.

In some embodiments, an increase in the level of one or more miRNAs selected from the group consisting of hsa-miR-125b-5p, hsa-miR-34a-5p, hsa-miR-378a-3p, hsa-miR-99a-5p, hsa-miR-365a-3p, hsa-miR-215-5p, hsa-miR-194-5p, hsa-miR-122-5p, and hsa-miR-192-5p indicates a worsening in fibrosis stage. In some embodiments, a decrease in the levels of one or more miRNAs selected from the group consisting of hsa-miR-1260b, hsa-let-7i-5p, and hsa-miR-222-3p indicates a worsening in fibrosis stage.

In some embodiments, a decrease in the levels of one or more miRNAs selected from the group consisting of hsa-miR-125b-5p, hsa-miR-34a-5p, hsa-miR-378a-3p, hsa-miR-99a-5p, hsa-miR-365a-3p, hsa-miR-215-5p, hsa-miR-194-5p, hsa-miR-122-5p, and hsa-miR-192-5p indicates an improvement in fibrosis stage. In some embodiments, an increase in the levels of one or more miRNAs selected from the group consisting of hsa-miR-1260b, hsa-let-7i-5p, and hsa-miR-222-3p indicates an improvement in fibrosis stage.

In some embodiments, the present invention provides a microRNA (miRNA) of any of SEQ ID NO:1 to 149.

IX. Therapeutic Agents

In some embodiments, one or more therapeutic agents include, and are not limited to, a(n) ACE inhibitor, Acetyl CoA carboxylase (ACC) inhibitor, Adenosine A3 receptor agonist, Adiponectin receptor agonist, AKT protein kinase inhibitor, AMP-activated protein kinases (AMPK), Amylin receptor agonist, Angiotensin II AT-1 receptor antagonist, Apoptosis signal-regulating kinase 1 (ASK1) inhibitor, Autotaxin inhibitors, Bioactive lipid, Calcitonin agonist, Caspase inhibitor, Caspase-3 stimulator, Cathepsin inhibitor, Caveolin 1 inhibitor, CCR2 chemokine antagonist, CCR3 chemokine antagonist, CCR5 chemokine antagonist, Chloride channel stimulator, CNR1 inhibitor, Cyclin D1 inhibitor, Cytochrome P450 7A1 inhibitor, DGAT1/2 inhibitor, Dipeptidyl peptidase IV inhibitor, Endosialin modulator, Eotaxin ligand inhibitor, Extracellular matrix protein modulator, Farnesoid X receptor agonist, Fatty acid synthase inhibitors, FGF1 receptor agonist, Fibroblast growth factor (FGF-15, FGF-19, FGF-21) ligands, Galectin-3 inhibitor, Glucagon receptor agonist, Glucagon-like peptide 1 agonist, G-protein coupled bile acid receptor 1 agonist, Hedgehog (Hh) modulator, Hepatitis C virus NS3 protease inhibitor, Hepatocyte nuclear factor 4 alpha modulator (HNF4A), Hepatocyte growth factor modulator, HMG CoA reductase inhibitor, IL-10 agonist, IL-17 antagonist, Ileal sodium bile acid cotransporter inhibitor, Insulin sensitizer, integrin modulator, interleukin-1 receptor-associated kinase 4 (IRAK4) inhibitor, Jak2 tyrosine kinase inhibitor, Klotho beta stimulator, 5-Lipoxygenase inhibitor, Lipoprotein lipase inhibitor, Liver X receptor, LPL gene stimulator, Lysophosphatidate-1 receptor antagonist, Lysyl oxidase homolog 2 inhibitor, Matrix metalloproteinases (MMPs) inhibitor, MEKK-5 protein kinase inhibitor, Membrane copper amine oxidase (VAP-1) inhibitor, Methionine aminopeptidase-2 inhibitor, Methyl CpG binding protein 2 modulator, MicroRNA-21 (miR-21) inhibitor, Mitochondrial uncoupler, Myelin basic protein stimulator, NACHT LRR PYD domain protein 3 (NLRP3) inhibitor, NAD-dependent deacetylase sirtuin stimulator, NADPH oxidase inhibitor (NOX), Nicotinic acid receptor 1 agonist, P2Y13 purinoceptor stimulator, PDE 3 inhibitor, PDE 4 inhibitor, PDE 5 inhibitor, PDGF receptor beta modulator, Phospholipase C inhibitor, PPAR alpha agonist, PPAR delta agonist, PPAR gamma agonist, PPAR gamma modulator, Protease-activated receptor-2 antagonist, Protein kinase modulator, Rho associated protein kinase inhibitor, Sodium glucose transporter-2 inhibitor, SREBP transcription factor inhibitor, STAT-1 inhibitor, Stearoyl CoA desaturase-1 inhibitor, Suppressor of cytokine signaling-1 stimulator, Suppressor of cytokine signalling-3 stimulator, Transforming growth factor β (TGF-β), Transforming growth factor β activated Kinase 1 (TAK1), Thyroid hormone receptor beta agonist, TLR-4 antagonist, Transglutaminase inhibitor, Tyrosine kinase receptor modulator, GPCR modulator, nuclear hormone receptor modulator, WNT modulators, or YAP/TAZ modulator.

It is understood that therapeutic agents described herein may inhibit one or more targets and not limited to the specified classes described herein. In some embodiments, one or more therapeutic agents are suitable for treating a liver disease or condition. In some embodiments, one or more therapeutic agents are suitable for treating NASH and/or liver fibrosis. Additional non-limiting examples of therapeutic agents and targets comprise:

ACE inhibitors, such as enalapril;
Acetyl CoA carboxylase (ACC) inhibitors, such as NDI-010976, DRM-01, gemcabene, PF-05175157, QLT-091382;
Adenosine receptor agonists, such as CF-102, CF-101, CF-502, CGS21680;
Adiponectin receptor agonists, such as ADP-355;
Amylin/calcitonin receptor agonists, such as KBP-042;
AMP activated protein kinase stimulators, such as O-304;
Angiotensin II AT-1 receptor antagonists, such as irbesartan;
Apoptosis signal-regulating kinase 1 (ASK1), selonsertib;
Autotaxin inhibitors, such as PAT-505, PAT-048, GLPG-1690, X-165, PF-8380, AM-063;
Bioactive lipids, such as DS-102;
Cannabinoid receptor type 1 (CNR1) inhibitors, such as namacizumab, GWP-42004;
Caspase inhibitors, such as emricasan;
Pan cathepsin B inhibitors, such as VBY-376;
Pan cathepsin inhibitors, such as VBY-825;
CCR2/CCR5 chemokine antagonists, such as cenicriviroc;
CCR2 chemokine antagonists, such as propagermanium;
CCR3 chemokine antagonists, such as bertilimumab;
Chloride channel stimulators, such as cobiprostone;
Diglyceride acyltransferase 2 (DGAT2) inhibitors, such as IONIS-DGAT2Rx;
Dipeptidyl peptidase IV inhibitors, such as linagliptin;
Eotaxin ligand inhibitors, such as bertilimumab;
Extracellular matrix protein modulators, such as CNX-024;
Farnesoid X receptor (FXR) agonists, such as AGN-242266, AKN-083, EDP-305, GNF-5120, GS-9674, LJN-452, LMB-763, obeticholic acid, Px-102, Px-103, M790, M780, M450, M480, PX20606, EYP-001, INT-2228;
Farnesoid X receptor (FXR)/G-protein coupled bile acid receptor 1 (TGR5) agonists, such as INT-767;
Fatty acid synthase inhibitors, such as TVB-2640;
Fibroblast growth factor 19 (rhFGF19)/cytochrome P450 (CYP) 7A1 inhibitors, such as NGM-282;
Fibroblast growth factor 21 (FGF-21) ligand, such as BMS-986171, BMS-986036;
Fibroblast growth factor 21 (FGF-21)/glucagon like peptide 1 (GLP-1) agonist, such as YH-25723;
Galectin-3 inhibitors, such as GR-MD-02;
Glucagon-like peptide 1 (GLP1R) agonists, such as AC-3174, liraglutide, semaglutide;
G-protein coupled bile acid receptor 1 (TGR5) agonists, such as RDX-009, INT-777;
Heat shock protein 47 (HSP47) inhibitors, such as ND-L02-s0201;
HMG CoA reductase inhibitors, such as atorvastatin, fluvastatin, pitavastatin, pravastatin, rosuvastatin, simvastatin;
IL-10 agonists, such as peg-ilodecakin;
Ileal sodium bile acid cotransporter inhibitors, such as A-4250, volixibat potassium ethanolate hydrate (SHP-262), GSK2330672;
Insulin sensitizers, such as, KBP-042, MSDC-0602K, Px-102, RG-125 (AZD4076), VVP-100X;
beta Klotho (KLB)-FGF1c agonist, such as NGM-313;
5-Lipoxygenase inhibitors, such as tipelukast (MN-001);
Lipoprotein lipase inhibitors, such as CAT-2003;
LPL gene stimulators, such as alipogene tiparvovec;

Liver X receptor (LXR) inhibitors, such as PX-L603, PX-L493, BMS-852927, T-0901317, GW-3965, SR-9238;

Lysophosphatidate-1 receptor antagonists, such as BMT-053011, UD-009. AR-479, ITMN-10534, BMS-986020, KI-16198;

Lysyl oxidase homolog 2 inhibitors, such as simtuzumab;

MEKK-5 protein kinase inhibitors, such as selonsertib;

Semicarbazide-Sensitive Amine Oxidase/Vascular Adhesion Protein-1 (SSAO/VAP-1) Inhibitors, such as PXS-4728A;

Methionine aminopeptidase-2 inhibitors, such as ZGN-839;

Methyl CpG binding protein 2 modulators, such as mercaptamine;

Mitochondrial uncouplers, such as 2,4-dinitrophenol;

Myelin basic protein stimulators, such as olesoxime;

NADPH oxidase 1/4 inhibitors, such as GKT-831;

Nicotinic acid receptor 1 agonists, such as ARI-3037MO;

NACHT LRR PYD domain protein 3 (NLRP3) inhibitors, such as KDDF-201406-03, NBC-6;

Nuclear receptor modulators, such as DUR-928;

P2Y13 purinoceptor stimulators, such as CER-209;

PDE 3/4 inhibitors, such as tipelukast (MN-001);

PDE 5 inhibitors, such as sildenafil;

PDGF receptor beta modulators, such as BOT-191, BOT-509;

PPAR agonists, such as elafibranor (GFT-505), MBX-8025, deuterated pioglitazone R-enantiomer, pioglitazone, DRX-065, saroglitazar, IVA-337;

Protease-activated receptor-2 antagonists, such as PZ-235;

Protein kinase modulators, such as CNX-014;

Rho associated protein kinase (ROCK) inhibitors, such as KD-025;

Sodium glucose transporter-2 (SGLT2) inhibitors, such as ipragliflozin, remogliflozin etabonate, ertugliflozin, dapagliflozin, sotagliflozin;

SREBP transcription factor inhibitors, such as CAT-2003, MDV-4463;

Stearoyl CoA desaturase-1 inhibitors, such as aramchol;

Thyroid hormone receptor beta agonists, such as MGL-3196, MGL-3745, VK-2809;

TLR-4 antagonists, such as JKB-121;

Tyrosine kinase receptor modulators, such as CNX-025;

GPCR modulators, such as CNX-023; or

Nuclear hormone receptor modulators, such as Px-102.

In some embodiments, one or more therapeutic agents may be A-4250, AC-3174, acetylsalicylic acid, AK-20, alipogene tiparvovec, aramchol, ARI-3037MO, ASP-8232, bertilimumab, Betaine anhydrous, BI-1467335, BMS-986036, BMS-986171, BMT-053011, BOT-191, BTT-1023, CAT-2003, cenicriviroc, CER-209, CF-102, CGS21680, CNX-014, CNX-023, CNX-024, CNX-025, cobiprostone, colesevelam, dapagliflozin, deuterated pioglitazone R-enantiomer, 2,4-dinitrophenol, DRX-065, DS-102, DUR-928, EDP-305, elafibranor (GFT-505), emricasan, enalapril, ertugliflozin, evogliptin, F-351, GKT-831, GNF-5120, GR-MD-02, selonsertib, GS-9674, hydrochlorothiazide, icosapent ethyl ester, IMM-124-E, INT-767, IONIS-DGAT2Rx, ipragliflozin, Irbesarta, propagermanium, IVA-337, JKB-121, KB-GE-001, KBP-042, KD-025, M790, M780, M450, metformin, sildenafil, LC-280126, linagliptin, liraglutide, LJN-452, LMB-763, MBX-8025, MDV-4463, mercaptamine, MGL-3196, MGL-3745, MSDC-0602K, namacizumab, NC-101, NDI-010976, ND-L02-s0201, NGM-282, NGM-313, NGM-386, NGM-395, norursodeoxycholic acid, 0-304, obeticholic acid, 25HC3S, olesoxime, PAT-505, PAT-048, peg-ilodecakin, pioglitazone, pirfenidone, PRI-724, PX20606, Px-102, PX-L603, PX-L493, PXS-4728A, PZ-235, RDX-009, remogliflozin etabonate, RG-125 (AZD4076), saroglitazar, semaglutide, simtuzumab, solithromycin, sotagliflozin, statins (atorvastatin, fluvastatin, pitavastatin, pravastatin, rosuvastatin, simvastatin), TCM-606F, TEV-45478, tipelukast (MN-001), TLY-012, TRX-318, TVB-2640, UD-009, ursodeoxycholic acid, VBY-376, VBY-825, VK-2809, vismodegib, volixibat potassium ethanolate hydrate (SHP-626), VVP-100X, WAV-301, WNT-974, ZGN-839, or any combination thereof. In some embodiments, the one or more therapeutic agents may be an ACC inhibitor described in WO2013/071169. In some embodiments, the one or more therapeutic agents can be an ASK1 inhibitor described in WO2013/112741. In some embodiments, the one or more therapeutic agents can be an FXR inhibitor described in WO2013/007387.

In some embodiments, the therapeutic agents can include one or more of selonsertib, GS-0976, and GS-9674. In some embodiments, the therapeutic agents can include at least two of selonsertib, GS-0976, and GS-9674. In some embodiments, the therapeutic agents can include selonsertib and GS-0976. In some embodiments, the therapeutic agents can include selonsertib and GS-9674. In some embodiments, the therapeutic agents can include GS-0976 and GS-9674. In some embodiments, the therapeutic agents can include selonsertib, GS-0976, and GS-9674.

X. Combination Correlates

In some embodiments, the methods described herein (i.e. method of diagnosing, method of treating, method of monitoring a liver disease or condition, and method of detecting) may be further combined with any one or more of the following liver disease or condition correlates: Adiponectin, Age, Alanine aminotransferase (ALT), Albumin, Alpha 2 Macroglibulin (A2M), Apolipoprotein B (ApoB)/Apolipoprotein A1 (ApoA1), Aspartate Aminotransferase (AST), Bilirubin, Body mass index (BMI), C4M2, Cholesterol, C-reactive protein (CRP), Cytokeratin-18 (CK-18), Diabetes, Glucose, Glycated Hemoglobulin (Hb Ac1), Haptogobin, Hepatocellular ballooning, Homeostatic Model Assessment-Insulin Resistance (HOMA-IR), Hyaluronic acid (HA), Impaired fasting glycemia (IFG), Insulin, Liver Biopsy, Lobular inflammation, Lumican (LUM), Lysyl Oxidase Like 2 (sLOXL2), Macroglobulin, Magnetic Resonance Elastography (MRE), Magnetic Resonance Imaging-Estimated Proton Density Fat Fraction (MRI-PDFF), P4NP7S, Plasma Pro-C3 (N-terminal type III collagen propeptide), Plasma Pro-C3 (N-terminal type V collagen propeptide), Platelet count, Procollagen type III-terminal peptide (PIIINP), Prothrombin time, Steatosis, Tissue inhibitor of metalloproteinases-1 (TIMP-1), Transforming Growth Factor Beta-Induced Protein (TGFBI), Transient Clastography (Liver Stiffness), Triglycerides, Urea, Waist:Hip ratio, or γ-glutamyl transferase (GGT), or combination(s) thereof.

In some embodiments, the methods described herein (i.e. method of diagnosing, method of treating, method of monitoring a liver disease or condition, and method of detecting) may be further combined with any one or more of the following liver disease or condition scoring systems: Fibrosis-4 (FIB-4), BAAT (Body Mass Index, Age at liver biopsy, Alanine aminotransferase, and serum Triglycerides), Non-Alcoholic Fatty Liver Disease (NAFLD) Fibrosis Score, BARD (Body Mass Index, Aspartate Aminotransferase/Alanine Aminotransferase Ratio, Diabetes), Enhanced Liver Fibrosis (ELF®), Fibrosure®, Fibrotest®, Fibrometer®, or Fibroscan®, or combination(s) thereof.

In some embodiments, the methods described herein (i.e. method of diagnosing, method of treating, method of monitoring a liver disease or condition, and method of detecting) may be further combined with any one or more of the following liver disease or condition scoring systems: Scheuer, Batts-Ludwig, METAVIR, Ishak, Laennec, Brunt, or Kleiner, or combination(s) thereof.

XI. Examples

Example 1

Plasma samples were obtained from 56 subjects suspected of having NASH (sNASH) based on metabolic syndrome, serum ALT, liver stiffness, or NAS score and 39 healthy subjects. The sNASH subjects may be grouped based on NAS scores or Fibrosis stages: 1 subject in NAS 0-2 (3.3%), 12 subjects in NAS 3-4 (40%), 17 subjects in NAS 5-8 (56.7%). 15 (50%) subjects had fibrosis between stages 0 and 2. 15 (50%) subjects had fibrosis between stages 3 and 4.

Total RNA from the plasma samples were isolated using RNA isolation kits. Complementary DNA was synthesized using QuantiMiR kit and 380 miRNAs were measured by qPCR using miRnome Profiler. miRNA expression levels were normalized against U1 spliceosomal RNA. miRNA qPCR analysis was performed. Differential miRNA expression analyses were performed using Significance Analysis Microarray (SAM) method; p-values in multiple comparisons were corrected using the Benjamini-Hochberg method. A random forest classifier was built to distinguish sNASH and health subjects by combining ten miRNAs (hsa-miR-15b, hsa-miR-17, hsa-miR-451, hsa-miR-15a, and hsa-miR-19b, hsa-miR-483-3p, hsa-miR-499-3p, hsa-miR-181d, hsa-miR-124, and hsa-miR-34a) having a p-value less than 0.01 and AUC greater than 0.69. Spearman correlations were calculated between miRNA expression with fibrosis stage and NAS score in sNASH subjects. 97 miRNA were differentially expressed between sNASH and healthy subjects.

A panel of the 10 miRNAs (hsa-miR-15b, hsa-miR-17, hsa-miR-451, hsa-miR-15a, and hsa-miR-19b, hsa-miR-483-3p, hsa-miR-499-3p, hsa-miR-181d, hsa-miR-124, and hsa-miR-34a) have an area under the curve (AUC) of 0.93 for differentiating between sNASH subjects and controls with a sensitivity of 80% and a specificity of 100%.

The following miRNAs correlated with fibrosis and/or NASH: hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-122, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, and hsa-miR-127-3p.

Table 1 summarizes the fold change, p-value, and area under the curve (AUC) for miRNA. The fold change describes the difference in quantity in miRNA between sNASH and controls (i.e. increase or decrease in level of respective miRNA). A fold change greater than 1 generally shows an increase in miRNA concentration, whereas a fold change less than 1 generally shows a decrease in miRNA concentration. The p-value describes the statistical significance of the difference in quantity of miRNA between sNASH and controls (i.e. the significance of the fold change). The AUC describes the probability that the miRNA is not random. In prediction analysis, AUC is the area under the ROC (Receiver operating characteristic) curve. It is a summarized measurement of both sensitivity and specificity of prediction. AUC ranges from 0 to 1. In a balanced data set (i.e. ratio of case/control close to 1), a perfect prediction without classification error would achieve an AUC of 1, while a random prediction without any knowledge about the domain problem would get an AUC of 0.5. An AUC value below 0.5 generally means that the prediction goes to the wrong direction, for example, predicting case as control or vice versa. Generally, an AUC between 0.7 and 1 shows a better prediction than an AUC between 0.6 and 0.7, which shows a better prediction than an AUC between 0.5 and 0.6.

A fold-change greater than 1.10 or less than 0.80, a p-value less than 1.0, and an AUC between 0.5 and 1.0 may be used as a biomarker for NASH and/or fibrosis. In some embodiments, a fold-change greater than 1.70 or less than 0.70, a p-value less than 0.1, and an AUC between 0.6 and 1.0 may be used as a biomarker for NASH and/or fibrosis. In some embodiments, a fold-change greater than 1.90 or less than 0.50, a p-value less than 0.01, and an AUC between 0.68 and 1.0 may be used as a biomarker for NASH and/or fibrosis.

TABLE 1

|  | microRNA | Fold Change | p-Value | AUC |
|---|---|---|---|---|
| SEQ ID NO: 1 | hsa-miR-15b | 4.28 | 1.21E−08 | 0.891 |
| SEQ ID NO: 2 | hsa-miR-17 | 4.99 | 3.71E−07 | 0.852 |
| SEQ ID NO: 3 | hsa-miR-451 | 3.12 | 4.53E−07 | 0.846 |
| SEQ ID NO: 4 | hsa-miR-15a | 3.30 | 1.92E−06 | 0.827 |
| SEQ ID NO: 5 | hsa-miR-20b | 4.47 | 3.26E−06 | 0.819 |
| SEQ ID NO: 6 | hsa-miR-16 | 2.53 | 7.63E−06 | 0.807 |
| SEQ ID NO: 7 | hsa-miR-195 | 2.34 | 9.90E−06 | 0.803 |
| SEQ ID NO: 8 | hsa-miR-25 | 2.52 | 1.16E−05 | 0.799 |
| SEQ ID NO: 9 | hsa-miR-320b | 2.24 | 3.35E−05 | 0.785 |
| SEQ ID NO: 10 | hsa-miR-320c | 2.26 | 5.71E−05 | 0.777 |
| SEQ ID NO: 11 | hsa-miR-101 | 2.81 | 6.22E−05 | 0.775 |
| SEQ ID NO: 12 | hsa-miR-21 | 2.10 | 7.32E−05 | 0.772 |
| SEQ ID NO: 13 | hsa-miR-150 | 1.91 | 1.22E−04 | 0.764 |
| SEQ ID NO: 14 | hsa-miR-20a | 1.96 | 1.22E−04 | 0.763 |
| SEQ ID NO: 15 | hsa-miR-148a | 2.29 | 2.02E−04 | 0.755 |
| SEQ ID NO: 16 | hsa-miR-191 | 1.96 | 3.93E−04 | 0.744 |
| SEQ ID NO: 17 | hsa-miR-106a | 2.04 | 4.35E−04 | 0.742 |
| SEQ ID NO: 18 | hsa-miR-24 | 2.34 | 7.12E−04 | 0.734 |
| SEQ ID NO: 19 | hsa-miR-26b | 2.18 | 7.12E−04 | 0.733 |
| SEQ ID NO: 20 | hsa-miR-424 | 2.07 | 8.52E−04 | 0.729 |
| SEQ ID NO: 21 | hsa-miR-483-3p | 0.26 | 2.83E−04 | 0.75 |
| SEQ ID NO: 22 | hsa-miR-499-3p | 0.43 | 8.40E−04 | 0.73 |
| SEQ ID NO: 23 | hsa-miR-181d | 0.34 | 1.22E−03 | 0.721 |
| SEQ ID NO: 24 | hsa-miR-124 | 0.39 | 3.19E−03 | 0.701 |
| SEQ ID NO: 25 | hsa-miR-125b | 0.41 | 3.63E−03 | 0.698 |
| SEQ ID NO: 26 | hsa-miR-34a | 0.41 | 4.36E−03 | 0.695 |
| SEQ ID NO: 27 | hsa-miR-362-5p | 0.48 | 4.97E−03 | 0.691 |

TABLE 1-continued

| | microRNA | Fold Change | p-Value | AUC |
|---|---|---|---|---|
| SEQ ID NO: 28 | hsa-miR-512-3p | 0.41 | 5.66E−03 | 0.688 |
| SEQ ID NO: 29 | hsa-miR-485-3p | 0.37 | 5.66E−03 | 0.687 |
| SEQ ID NO: 30 | hsa-miR-132 | 0.46 | 6.89E−03 | 0.682 |
| SEQ ID NO: 31 | hsa-miR-92a | 2.06 | 1.02E−03 | 0.726 |
| SEQ ID NO: 32 | hsa-let-7b | 1.85 | 1.22E−03 | 0.72 |
| SEQ ID NO: 33 | hsa-miR-19b | 2.18 | 1.22E−03 | 0.72 |
| SEQ ID NO: 34 | hsa-miR-93 | 2.06 | 1.22E−03 | 0.72 |
| SEQ ID NO: 35 | hsa-miR-19a | 2.01 | 1.22E−03 | 0.72 |
| SEQ ID NO: 36 | hsa-miR-142-3p | 2.00 | 1.44E−03 | 0.717 |
| SEQ ID NO: 37 | hsa-let-7e | 1.98 | 1.52E−03 | 0.715 |
| SEQ ID NO: 38 | hsa-miR-223 | 1.96 | 1.84E−03 | 0.712 |
| SEQ ID NO: 39 | hsa-miR-148b | 2.70 | 2.87E−03 | 0.704 |
| SEQ ID NO: 40 | hsa-miR-30e | 2.07 | 3.54E−03 | 0.699 |
| SEQ ID NO: 41 | hsa-miR-30a | 1.73 | 4.72E−03 | 0.693 |
| SEQ ID NO: 42 | hsa-miR-26a | 1.77 | 4.97E−03 | 0.691 |
| SEQ ID NO: 43 | hsa-let-7a | 1.86 | 5.23E−03 | 0.69 |
| SEQ ID NO: 44 | hsa-miR-30d | 1.78 | 6.12E−03 | 0.685 |
| SEQ ID NO: 45 | hsa-miR-18b | 2.18 | 6.29E−03 | 0.685 |
| SEQ ID NO: 46 | hsa-miR-92b | 0.50 | 1.10E−02 | 0.673 |
| SEQ ID NO: 47 | hsa-miR-135a | 0.54 | 1.31E−02 | 0.669 |
| SEQ ID NO: 48 | hsa-miR-135b | 0.54 | 1.57E−02 | 0.663 |
| SEQ ID NO: 49 | hsa-miR-375 | 0.58 | 1.62E−02 | 0.662 |
| SEQ ID NO: 50 | hsa-miR-181a | 0.55 | 1.70E−02 | 0.661 |
| SEQ ID NO: 51 | hsa-miR-346 | 0.52 | 1.83E−02 | 0.659 |
| SEQ ID NO: 52 | hsa-miR-181c | 0.46 | 2.40E−02 | 0.652 |
| SEQ ID NO: 53 | hsa-miR-539 | 0.42 | 2.41E−02 | 0.652 |
| SEQ ID NO: 54 | hsa-miR-320d | 0.67 | 4.83E−02 | 0.635 |
| SEQ ID NO: 55 | hsa-miR-523 | 0.49 | 6.20E−02 | 0.628 |
| SEQ ID NO: 56 | hsa-miR-28-3p | 0.58 | 6.40E−02 | 0.626 |
| SEQ ID NO: 57 | hsa-miR-219-1-3p | 0.55 | 6.43E−02 | 0.626 |
| SEQ ID NO: 58 | hsa-miR-323-5p | 0.56 | 7.73E−02 | 0.62 |
| SEQ ID NO: 59 | hsa-miR-339-3p | 0.59 | 7.73E−02 | 0.62 |
| SEQ ID NO: 60 | hsa-miR-324-3p | 0.68 | 9.99E−02 | 0.612 |
| SEQ ID NO: 61 | hsa-miR-122 | 2.14 | 1.35E−02 | 0.668 |
| SEQ ID NO: 62 | hsa-miR-27a | 1.81 | 1.45E−02 | 0.667 |
| SEQ ID NO: 63 | hsa-let-7g | 1.81 | 1.49E−02 | 0.666 |
| SEQ ID NO: 64 | hsa-miR-486-5p | 1.74 | 1.54E−02 | 0.665 |
| SEQ ID NO: 65 | hsa-miR-425 | 1.66 | 1.56E−02 | 0.664 |
| SEQ ID NO: 66 | hsa-let-7c | 1.84 | 1.58E−02 | 0.663 |
| SEQ ID NO: 67 | hsa-miR-192 | 1.83 | 2.40E−02 | 0.652 |
| SEQ ID NO: 68 | hsa-miR-18a | 3.33 | 2.42E−02 | 0.652 |
| SEQ ID NO: 69 | hsa-miR-29a | 1.70 | 3.33E−02 | 0.644 |
| SEQ ID NO: 70 | hsa-miR-27b | 1.52 | 3.70E−02 | 0.641 |
| SEQ ID NO: 71 | hsa-let-7f | 1.58 | 4.63E−02 | 0.636 |
| SEQ ID NO: 72 | hsa-miR-151-5p | 1.45 | 5.99E−02 | 0.629 |
| SEQ ID NO: 73 | hsa-let-7d | 2.04 | 6.01E−02 | 0.629 |
| SEQ ID NO: 74 | hsa-miR-146a | 1.48 | 6.70E−02 | 0.625 |
| SEQ ID NO: 75 | hsa-miR-423-5p | 1.63 | 7.57E−02 | 0.621 |
| SEQ ID NO: 76 | hsa-miR-103 | 1.55 | 7.67E−02 | 0.62 |
| SEQ ID NO: 77 | hsa-miR-30c | 1.41 | 1.01E−01 | 0.612 |
| SEQ ID NO: 78 | hsa-miR-23a | 1.34 | 1.23E−01 | 0.605 |
| SEQ ID NO: 79 | hsa-miR-106b | 1.37 | 1.33E−01 | 0.602 |
| SEQ ID NO: 80 | hsa-miR-23b | 1.43 | 1.57E−01 | 0.596 |
| SEQ ID NO: 81 | hsa-miR-151-3p | 1.27 | 2.03E−01 | 0.587 |
| SEQ ID NO: 82 | hsa-miR-185 | 1.41 | 2.71E−01 | 0.577 |
| SEQ ID NO: 83 | hsa-miR-199a-3p | 1.28 | 2.74E−01 | 0.575 |
| SEQ ID NO: 84 | hsa-miR-22 | 1.51 | 3.16E−01 | 0.569 |
| SEQ ID NO: 85 | hsa-miR-378 | 1.12 | 3.99E−01 | 0.558 |
| SEQ ID NO: 86 | hsa-miR-28-5p | 0.60 | 1.09E−01 | 0.609 |
| SEQ ID NO: 87 | hsa-miR-370 | 0.61 | 1.13E−01 | 0.608 |
| SEQ ID NO: 88 | hsa-miR-34c-3p | 0.70 | 1.30E−01 | 0.603 |
| SEQ ID NO: 89 | hsa-miR-181b | 0.65 | 1.30E−01 | 0.603 |
| SEQ ID NO: 90 | hsa-miR-493 | 0.69 | 1.30E−01 | 0.603 |
| SEQ ID NO: 91 | hsa-miR-10a | 0.79 | 1.46E−01 | 0.598 |
| SEQ ID NO: 92 | hsa-miR-10b | 0.78 | 1.57E−01 | 0.596 |
| SEQ ID NO: 93 | hsa-miR-139-5p | 0.77 | 1.85E−01 | 0.59 |
| SEQ ID NO: 94 | hsa-miR-326 | 0.69 | 2.72E−01 | 0.576 |
| SEQ ID NO: 95 | hsa-miR-423-3p | 0.74 | 2.72E−01 | 0.576 |
| SEQ ID NO: 96 | hsa-miR-187 | 0.62 | 2.74E−01 | 0.575 |
| SEQ ID NO: 97 | hsa-miR-127-3p | 0.75 | 2.92E−01 | 0.572 |

Example 2

Plasma samples were obtained from 72 subjects enrolled in the GS-US-384-1497 Gilead study. The study is a phase 2 study evaluating the safety, tolerability, and efficacy of selonsertib (ASK1 inhibitor) alone or in combination with simtuzumab (SIM) in subjects with Nonalcoholic Steatohepatitis (NASH) and fibrosis stages F2-F3. The inclusion criteria included patients with metabolic syndrome, serum ALT≥1.5×ULN and ≤5×ULN, and Fibroscan that measures liver stiffness: ≥7 kPa and <12 kPa, or NAS score greater ≥5 with fibrosis stage 2 to 3.

Total RNA samples were isolated and 301 selected miRNA were measured by qPCR. MiRNA expression levels were normalized using the global mean of all expressed miRNAs. Differential expression analyses were performed using limma method; p-values in multiple comparisons were corrected using the Benjamini-Hochberg method. Spearman correlations were calculated between miRNA expression with fibrosis stage and NAS score at baseline and at week 24.

11 miRNAs (hsa-miR-505-3p, hsa-miR-29a-3p, hsa-miR-215-5p, hsa-miR-148a-3p, hsa-miR-99a-5p, hsa-miR-885-5p, hsa-miR-122-5p, hsa-miR-34a-5p, hsa-miR-365a-3p, hsa-miR-194-5p, hsa-miR-155-5p) with nominal P>0.05 were modulated by SEL treatment, see Table 2 below. The negative folder change indicates that the miRNA is down-regulated by SEL treatment (e.g., hsa-miR-505-3p, hsa-miR-29a-3p, hsa-miR-215-5p, hsa-miR-148a-3p, hsa-miR-99a-5p, hsa-miR-885-5p, hsa-miR-122-5p, hsa-miR-34a-5p, hsa-miR-365a-3p, hsa-miR-194-5p), while the positive folder change indicates that the miRNA is upregulated by SEL treatment (e.g., has-miR-155-5p).

TABLE 2

Eleven miRNAs were modulated by SEL treatment at week 24

| | 6 mg SEL ± SIM | | 18 mg SEL ± SIM | |
|---|---|---|---|---|
| | Fold Change | P-value | Fold Change | P-value |
| miR-365a-3p | −1.65 | 0.001 | — | — |
| miR-34a-5p | −1.54 | 0.004 | −1.33 | 0.03 |
| miR-99a-5p | −1.33 | 0.01 | −1.25 | 0.03 |
| miR-29a-3p | −1.23 | 0.01 | — | — |
| miR-122-5p | −1.42 | 0.01 | — | — |
| miR-194-5p | −1.30 | 0.01 | — | — |
| miR-148a-3p | −1.28 | 0.01 | — | — |
| miR-885-5p | −1.37 | 0.02 | −1.56 | 0.01 |
| miR-505-3p | −1.24 | 0.03 | — | — |
| miR-215-5p | −1.27 | 0.04 | — | — |
| miR-155-5p | — | — | 1.33 | 0.03 |

10 miRNAs (hsa-miR-125b-5p, hsa-miR-29a-3p, hsa-miR-150-5p, hsa-miR-136-5p, hsa-miR-30a-5p, hsa-miR-34a-5p, hsa-miR-29c-3p, hsa-miR-378a-3p, hsa-miR-99a-5p, hsa-miR-375) were associated with fibrosis stages F1-2 vs F3-4 at week 24. Table 3 summarizes the fold change, p-value, and area under the curve (AUC) for miRNAs that is associated with fibrosis stages F1-2 vs F3-4. A fold change greater than 1 generally shows an increase in miR concentration, whereas a fold change less than 1 generally shows a decrease in miR concentration. The p-value describes the statistical significance of the difference in the quantity of miR between F1-2 vs F3-4 (i.e. the significance of the fold change). The AUC describes the probability that the miR is not random. In prediction analysis, AUC is the area under the ROC (Receiver operating characteristic) curve. It is a summarized measurement of both sensitivity and specificity of prediction. AUC ranges from 0 to 1. In a balanced data set (i.e. the ratio of case/control close to 1), a perfect prediction without classification error would achieve an AUC of 1, while a random prediction without any knowledge about the domain problem would get an AUC of 0.5. An AUC value below 0.5 generally means that the prediction goes to the wrong direction, for example, predicting case as control or vice versa. Generally, an AUC between 0.7 and 1 shows a better prediction than an AUC between 0.6 and 0.7, which shows a better prediction than an AUC between 0.5 and 0.6.

A fold-change greater than 1.10 or less than 0.80, a p-value less than 1.0, and an AUC between 0.5 and 1.0 may be used as a biomarker for NASH and/or fibrosis. In some embodiments, a fold-change greater than 1.70 or less than 0.70, a p-value less than 0.1, and an AUC between 0.6 and 1.0 may be used as a biomarker for NASH and/or fibrosis. In some embodiments, a fold-change greater than 1.90 or less than 0.50, a p-value less than 0.01, and an AUC between 0.68 and 1.0 may be used as a biomarker for NASH and/or fibrosis.

Change of expression of 12 miRNAs (hsa-miR-125b-5p, hsa-miR-34a-5p, hsa-miR-378a-3p, hsa-miR-99a-5p, hsa-miR-1260b, hsa-miR-365a-3p, hsa-miR-215-5p, hsa-miR-194-5p, let-7i-5p, hsa-miR-122-5p, hsa-miR-192-5p and hsa-miR-222-3p) from BL to week 24 associated with fibrosis change. Table 4 summarizes the spearman correlations (rho, ρ) to change in stages of fibrosis. The first 10 miRNAs listed in Table 4 are the top 10 miRNAs that are associated with fibrosis change. Spearman's correlation assesses the relationship between two variables. The analysis expresses the strength of the relationship in values between −1 and +1. The positive correlation coefficient indicates positive relationship and a negative correlation coefficient indicates negative relationship (i.e., a positive value indicates that (1) an increase in miRNA level is correlated with worsening of the fibrosis stage and (2) a decrease in miRNA level is correlated with improvement of the fibrosis stage; and a negative value indicates that (1) an increase in miRNA level is correlated with improvement of the fibrosis stage and (2) a decrease in miRNA level is correlated with worsening of the fibrosis stage). A value of 0 indicates no relationship.

16 miRNAs (hsa-miR-125b-5p, hsa-miR-29a-3p, hsa-miR-378a-3p, hsa-miR-30a-5p, hsa-miR-34a-5, hsa-miR-99a-5p, hsa-miR-192-5p, hsa-miR-365a-3p, hsa-miR-22-5p, hsa-miR-505-3p, hsa-miR-320d, hsa-miR-215-5p, hsa-miR-122-5p, hsa-miR-194-5p, hsa-miR-885-5p, miR-107) associated with NAS score at week 24. Table 5 summarizes the spearman correlations (rho, ρ) to NAS score. A Spearman correlation describes a relationship between two variables. A positive rho, ρ values suggests that with increase in NAS score there is an increase in miRNA expression and a negative correlation suggest that with increase in NAS score there is a decrease in miRNA expression Changes of 11 miRNAs (hsa-miR-122-5p, hsa-miR-125b-5p, hsa-miR-365a-3p, hsa-miR-192-5p, hsa-miR-215-5p, hsa-miR-885-5p, hsa-miR-505-3p, hsa-miR-194-5p, hsa-miR-99a-5p, hsa-miR-34a-5p, hsa-miR-378a-3p) Tables 6-7 were associated with changes of other serum biomarkers such as ALT, AST, CK18M65, CK18M30. A Spearman correlation describes a relationship between two variables. A positive rho, ρ values suggests that with increase in ALT, AST, CK18M65 or CK18M30 there is an increase in miRNA expression and a negative correlation suggest that with increase in ALT, AST, CK18M65 or CK18M30 there is a decrease in miRNA expression To identify the most informative subset of miRNAs for each of the three responses in study GS-384-1497—diagnosing baseline (F2 vs. F3) or week 24 (F1,2 vs F3,4) fibrosis stage and monitoring week 24 fibrosis improvement (≥1 stage reduction vs <1 stage reduction), 6 methods were performed and assigned with different scores for a miRNAs being selected. Then the total scores were aggregated across the 6 methods. A miRNA with total score≥3 was selected as most informative for respective endpoint. The 6 methods and the corresponding scores are "univariate logistic regression" (1), "multivariate logistic regression with lasso penalty" (1.5), "multivariate logistic regression with elastic net penalty" (1.5), "random forest with the Boruta algorithm for variable selection" (1), "conditional random forest" (1.5) and "Generalized, Unbiased, Interaction Detection and Estimation (GUIDE)" (2). For diagnosis of fibrosis stage at baseline (or week 24), baseline (or week 24) miRNA levels were used for modelling. For monitoring fibrosis improvement at week 24, both baseline miRNA levels and their fold changes at week 24 were used.

To build a multivariate diagnostic (baseline or week 24 fibrosis stage) or monitoring (week 24 fibrosis improvement) algorithm based on the most informative miRNAs, logistic regression with ridge penalty was conducted. The performance of the algorithm was evaluated using area under ROC curve (AUC).

TABLE 3

Human plasma miRNAs were associated with fibrosis stages at week 24 and could discriminate advanced fibrosis

| miRs | Fold Change (F3-4 vs F1-2) | p-value | AUROC repeated CV (95% CI) |
|---|---|---|---|
| miR-125b-5p | 1.45 | 0.01 | 0.69 | (0.66, 0.71) |
| miR-29a-3p | 1.27 | 0.01 | 0.7 | (0.68, 0.71) |
| miR-136-5p | −2.08 | 0.01 | 0.65 | (0.61, 0.68) |
| miR-30a-5p | 1.37 | 0.02 | 0.65 | (0.62, 0.68) |
| miR-29c-3p | 1.23 | 0.02 | 0.64 | (0.6, 0.66) |
| miR-378a-3p | 1.30 | 0.03 | 0.64 | (0.6, 0.66) |
| miR-34a-5p | 1.60 | 0.03 | 0.64 | (0.6, 0.66) |
| miR-99a-5p | 1.35 | 0.04 | 0.62 | (0.59, 0.65) |
| miR-150-5p | 1.46 | 0.04 | 0.61 | (0.4, 0.63) |
| miR-375 | 1.46 | 0.05 | 0.57 | (0.39, 0.63) |

TABLE 4

Human plasma miRNAs associated with change in fibrosis stage at week 24

| miRs | rs | p-value | AUROC repeated CV (95% CI) |
|---|---|---|---|
| miR-365a-3p | 0.35 | 0.009 | 0.57 | (0.44, 0.67) |
| miR-125b-5p | 0.33 | 0.013 | 0.6 | (0.53, 0.65) |
| miR-34a-5p | 0.33 | 0.014 | 0.55 | (0.45, 0.64) |
| miR-215-5p | 0.30 | 0.025 | 0.59 | (0.46, 0.7) |
| miR-194-5p | 0.30 | 0.025 | 0.55 | (0.51, 0.65) |
| miR-378a-3p | 0.30 | 0.025 | 0.54 | (0.47, 0.63) |
| miR-99a-5p | 0.30 | 0.027 | 0.57 | (0.45, 0.68) |
| miR-1260b | −0.39 | 0.006 | 0.72 | (0.68, 0.74) |
| let-7i-5p | −0.30 | 0.025 | 0.63 | (0.54, 0.73) |
| miR-122-5p | 0.29 | 0.028 | 0.68 | (0.65, 0.7) |
| miR-192-5p | 0.28 | — | — | — |
| miR-222-3p | −0.27 | — | — | — |

TABLE 5

Human plasma miRNAs associated with histological lesions at W24

| miRNA | Correlation to NAS score (rho) p < 0.05 |
|---|---|
| hsa-miR-125b-5p | 0.354862 |
| hsa-miR-29a-3p | 0.323883 |
| hsa-miR-378a-3p | 0.297566 |
| hsa-miR-30a-5p | 0.382422 |
| hsa-miR-34a-5p | 0.387948 |
| hsa-miR-99a-5p | 0.350648 |
| hsa-miR-192-5p | 0.271145 |
| hsa-miR-365a-3p | 0.270603 |
| hsa-miR-22-5p | 0.32295 |

TABLE 5-continued

Human plasma miRNAs associated with histological lesions at W24

| miRNA | Correlation to NAS score (rho) p < 0.05 |
|---|---|
| hsa-miR-505-3p | 0.29463 |
| hsa-miR-320d | 0.284131 |
| hsa-miR-215-5p | 0.317079 |
| hsa-miR-122-5p | 0.299914 |
| hsa-miR-194-5p | 0.277705 |
| hsa-miR-885-5p | 0.264191 |
| hsa-miR-107 | 0.254695 |

TABLE 6 microRNA correlations with ALT and AST baseline and Week 24

| miRNA | CK18M30: Baseline p < 0.001 | CK18M30: Week 24 p < 0.001 | CK18M65: Baseline p < 0.001 | CK18M65: Week 24 p < 0.001 |
|---|---|---|---|---|
| hsa-miR-122-5p | 0.64 | 0.71 | 0.63 | 0.80 |
| hsa-miR-125b-5p | 0.57 | 0.68 | 0.53 | 0.79 |
| hsa-miR-365a-3p | 0.64 | 0.64 | 0.64 | 0.78 |
| hsa-miR-192-5p | 0.64 | 0.62 | 0.59 | 0.67 |
| hsa-miR-215-5p | 0.62 | 0.61 | 0.56 | 0.67 |
| hsa-miR-885-5p | 0.66 | 0.59 | 0.65 | 0.68 |
| hsa-miR-505-3p | 0.60 | 0.64 | 0.63 | 0.77 |
| hsa-miR-194-5p | 0.66 | 0.64 | 0.65 | 0.75 |
| hsa-miR-99a-5p | 0.64 | 0.60 | 0.66 | 0.78 |
| hsa-miR-34a-5p | 0.72 | 0.67 | 0.76 | 0.80 |
| hsa-miR-378a-3p | 0.67 | 0.61 | 0.68 | 0.76 |

TABLE 7 microRNA correlations with CK18M30 and CK18M65 at baseline and Week 24

| miRNA | ALT: Baseline p < 0.001 | ALT: Week 24 p < 0.001 | AST: Baseline p < 0.001 | AST: Week 24 p < 0.001 |
|---|---|---|---|---|
| hsa-miR-122-5p | 0.55 | 0.60 | 0.51 | 0.72 |
| hsa-miR-125b-5p | 0.52 | 0.56 | 0.49 | 0.66 |
| hsa-miR-365a-3p | 0.45 | 0.54 | 0.39 | 0.66 |
| hsa-miR-192-5p | 0.54 | 0.56 | 0.49 | 0.61 |
| hsa-miR-215-5p | 0.55 | 0.55 | 0.47 | 0.62 |
| hsa-miR-885-5p | 0.61 | 0.58 | 0.56 | 0.67 |
| hsa-miR-505-3p | 0.64 | 0.68 | 0.62 | 0.76 |
| hsa-miR-194-5p | 0.60 | 0.59 | 0.56 | 0.69 |
| hsa-miR-99a-5p | 0.57 | 0.61 | 0.63 | 0.76 |
| hsa-miR-34a-5p | 0.54 | 0.55 | 0.61 | 0.73 |
| hsa-miR-378a-3p | 0.49 | 0.56 | 0.51 | 0.66 |

TABLE 8

AUC values of previous known correlates

| | AUC (95% CI) | |
|---|---|---|
| | BL (F2 vs F3) | WK24 (F1-2 vs F3-4) |
| MRE | 0.677 (0.655, 0.693) | 0.783 (0.756, 0.801) |
| FibroScan | 0.679 (0.657, 0.7) | 0.769 (0.746, 0.787) |
| CK18M30 | 0.56 (0.488, 0.68) | 0.573 (0.535, 0.601) |
| ELF | 0.633 (0.587, 0.66) | 0.709 (0.688, 0.726) |
| HYLURAC | 0.631 (0.594, 0.657) | 0.669 (0.639, 0.698) |
| TIMP1 | 0.639 (0.616, 0.657) | 0.638 (0.607, 0.657) |
| PIIINP | 0.521 (0.454, 0.625) | 0.627 (0.603, 0.644) |
| NFS | 0.701 (0.682, 0.715) | 0.678 (0.65, 0.699) |
| APRI | 0.595 (0.559, 0.616) | 0.653 (0.624, 0.672) |

TABLE 9 microRNA sequences

| SEQ ID # | microRNA | Sequence |
|---|---|---|
| SEQ ID NO: 25 | hsa-miR-125b-5p | UCCCUGAGACCCUAACUUGUGA |
| SEQ ID NO: 69 | hsa-miR-29a-3p | UAGCACCAUCUGAAAUCGGUUA |
| SEQ ID NO: 13 | hsa-miR-150-5p | CUGGUACAGGCCUGGGGGACAG |
| SEQ ID NO: 135 | hsa-miR-136-5p | ACUCCAUUUGUUUUGAUGAUGGA |
| SEQ ID NO: 136 | hsa-miR-30a-5p | UGUAAACAUCCUCGACUGGAAG |
| SEQ ID NO: 26 | hsa-miR-34a-5p | UGGCAGUGUCUUAGCUGGUUGU |
| SEQ ID NO: 117 | hsa-miR-29c-3p | UAGCACCAUUUGAAAUCGGUUA |
| SEQ ID NO: 137 | hsa-miR-378a-3p | ACUGGACUUGGAGUCAGAAGGC |
| SEQ ID NO: 102 | hsa-miR-99a-5p | AACCCGUAGAUCCGAUCUUGUG |
| SEQ ID NO: 49 | hsa-miR-375 | UUUGUUCGUUCGGCUCGCGUGA |
| SEQ ID NO: 138 | hsa-miR-1260b | AUCCCACCACUGCCACCAU |
| SEQ ID NO: 139 | hsa-miR-365a-3p | UAAUGCCCCUAAAAAUCCUUAU |
| SEQ ID NO: 140 | hsa-miR-215-5p | AUGACCUAUGAAUUGACAGAC |

TABLE 9-continued microRNA sequences

| SEQ ID # | microRNA | Sequence |
|---|---|---|
| SEQ ID NO: 116 | hsa-miR-194-5p | UGUAACAGCAACUCCAUGUGGA |
| SEQ ID NO: 141 | hsa-let-7i-5p | UGAGGUAGUAGUUUGUGCUGUU |
| SEQ ID NO: 61 | hsa-miR-122-5p | UGGAGUGUGACAAUGGUGUUUG |
| SEQ ID NO: 67 | hsa-miR-192-5p | CUGACCUAUGAAUUGACAGCC |
| SEQ ID NO: 142 | hsa-miR-222-3p | AGCUACAUCUGGCUACUGGGU |
| SEQ ID NO: 85 | hsa-miR-378a-3p | ACUGGACUUGGAGUCAGAAGGC |
| SEQ ID NO: 41 | hsa-miR-30a-5p | UGUAAACAUCCUCGACUGGAAG |
| SEQ ID NO: 143 | hsa-miR-365a-3p | UAAUGCCCCUAAAAAUCCUUAU |
| SEQ ID NO: 114 | hsa-miR-22-5p | AGUUCUUCAGUGGCAAGCUUUA |
| SEQ ID NO: 144 | hsa-miR-505-3p | CGUCAACACUUGCUGGUUUCCU |
| SEQ ID NO: 54 | hsa-miR-320d | AAAAGCUGGGUUGAGAGGA |
| SEQ ID NO: 145 | hsa-miR-885-5p | UCCAUUACACUACCCUGCCUCU |
| SEQ ID NO: 146 | hsa-miR-107 | AGCAGCAUUGUACAGGGCUAUCA |
| SEQ ID NO: 147 | hsa-miR-100-5p | AACCCGUAGAUCCGAACUUGUG |
| SEQ ID NO: 15 | hsa-miR-148a-3p | UCAGUGCACUACAGAACUUUGU |
| SEQ ID NO: 148 | hsa-miR-155-5p | UUAAUGCUAAUCGUGAUAGGGGU |
| SEQ ID NO: 74 | hsa-miR-146a-5p | UGAGAACUGAAUUCCAUGGGUU |
| SEQ ID NO: 25 | hsa-miR-125b-5p | UCCCUGAGACCCUAACUUGUGA |
| SEQ ID NO: 93 | hsa-miR-139-5p | UCUACAGUGCACGUGUCUCCAGU |
| SEQ ID NO: 149 | hsa-miR-874-3p | CUGCCCUGGCCCGAGGGACCGA |
| SEQ ID NO: 92 | hsa-miR-10b-5p | UACCCUGUAGAACCGAAUUUGUG |

Example 3. microRNA Analysis in GS-US-321-0105 and GS-US-321-0106 in Subjects with Natural History of Fibrosis Changes Introduction Previously, MicroRNA (miR) analysis of the GS-US-384-1497 study in patients with NASH and fibrosis stages F3 and F3 identified: Expression of 12 miRs including miRs involved in regulating liver homeostasis was altered after SEL treatment; 10 miRs including miR-34a-5p are associated with hepatic fibrosis stage and can discriminate advance fibrosis with AUC ranging from 0.57-0.70; Changes in 10 miRs are correlated with changes in fibrosis stage. miR-122-5p and miR-34a-5p can distinguish fibrosis improvement with AUC of 70% (95% CI 0.45, 0.64) and 55% (95% CI 0.48, 0.78) respectively.

The miR analysis was expanded to using GS-US-321-0105 and GS-US-321-0106 studies where biopsy proven samples were used from NASH patients. These studies had evaluated the safety and efficacy of Simtuzamab (SIM) in NASH patients. However, SIM was ineffective at reducing fibrosis. It was observed that 20% of the samples had fibrosis improvement, 20% fibrosis regression and for the rest of the subjects the fibrosis remained unchanged. As these samples represented the natural history of fibrosis changes, miR expression was analyzed in these samples.

Objective

Identify the utility of circulating microRNAs (miRs) to detect fibrosis stage and to monitor fibrosis stage change for subjects with NASH.

Samples

Subjects in GS-US-384-1497 phase 2 trials were enrolled with F2-3 Stages of fibrosis and subjects in GS-US-321-0105 phase 2 trial were enrolled with F3 Stage of fibrosis and GS-US-321-0106 phase 2 trial subjects were enrolled with F4 stage of fibrosis.

Screen failed subjects were included in the analysis to ensure the miRs were analyzed in all the fibrosis stages. The samples analyzed after quality control, which excluded samples that were hemolyzed and samples that had overall low expression of miRs.

Methods

Plasma miRs were isolated with spike-in controls using total RNA isolation kit (Exiqon, Denmark). Complementary DNA was synthesized with spike-in control using the Exiqon cDNA synthesis kit and selected plasma miRs (n=157) were measured at BL, W12, and W24 by qPCR using the Exiqon platform (Covance, USA). For the 1497 study, 301 miRs were measured but only 132 miRs were expressed therefore for the 105/106 studies we measured the 132 miRs with 25 additional miRs were measured for the 105/106 study. The data was normalized using Global fit method of normalization.

Results

MiRs Association with SIM

We first confirmed if there any miRs associated with SIM treatment and as expected there were no miRs associated with SIM treatment.

MiRs Correlated with Fibrosis Score

The top miRs that correlated with fibrosis scores are has-miR-34a-5p, has-mR-362-3p, has-miR-32-5p, has-miR-193a-5p, has-miR-21-5p.

miRs are Differentially Expressed at Baseline Between F0 vs F1-4 and F4 vs F0-3

TABLE 11

| miRNA | FC | CI | AUC | p-value |
|---|---|---|---|---|
| | | week 48 | | |
| hsa-miR-362-3p | 1.36 | (1.151, 1.603) | 0.70 | 0.00 |
| hsa-miR-32-5p | 1.21 | (1.060, 1.380) | 0.66 | 0.01 |
| hsa-miR-342-5p | 0.83 | (0.721, 0.946) | 0.66 | 0.01 |
| hsa-miR-21-5p | 1.10 | (1.019, 1.195) | 0.65 | 0.02 |
| hsa-miR-495-3p | 0.67 | (0.459, 0.983) | 0.60 | 0.04 |

TABLE 12

Best performance observed in diagnosing cirrhosis (F4 vs. F0-3) using individual miRNA's and combined best set (AUROC > 0.80)
Global fit normalized data

| | F0-2 vs F3-4 (SIM 105/106) | F0-3 vs F4 (SIM 105/106) | F0-2 vs F3 (SIM 105/106) | F1-2 vs F3-4 (SEL 1497) |
|---|---|---|---|---|
| Best Set[1] | 0.74 (0.73, 0.75)[2] | 0.87 (0.86, 0.88)[3] | 0.72 (0.71, 0.73)[4] | 0.73 (0.7, 0.75)[5] |
| Best Set + NFS + BA | 0.81 (0.8, 0.82) | 0.93 (0.92, 0.94) | 0.8 (0.79, 0.81) | 0.76 (0.74, 0.78) |
| Best Set + mir-34a + A2MACG | 0.75 (0.74, 0.76) | 0.88 (0.87, 0.89) | 0.72 (0.7, 0.74) | 0.72 (0.68, 0.74) |
| Best Set + mir-34a + A2MACG + YKL-40 | 0.75 (0.73, 0.76) | 0.88 (0.87, 0.89) | 0.73 (0.71, 0.74) | 0.71 (0.67, 0.74) |
| Best Set + NFS + BA + mir-34a + A2MACG + YKL-40 | 0.8 (0.79, 0.81) | 0.93 (0.92, 0.94) | 0.81 (0.79, 0.83) | 0.74 (0.7, 0.76) |
| NFS + BA | 0.75 (0.75, 0.76) | 0.81 (0.8, 0.82) | 0.77 (0.76, 0.78) | 0.69 (0.68, 0.71) |
| mir-34a + A2MACG | 0.56 (0.48, 0.62) | 0.62 (0.57, 0.64) | 0.67 (0.65, 0.68) | 0.6 (0.52, 0.64) |
| mir-34a + A2MACG + YKL-40 | 0.56 (0.49, 0.62) | 0.62 (0.49, 0.66) | 0.67 (0.65, 0.7) | 0.57 (0.46, 0.62) |
| Best single marker | 0.7 (0.69, 0.71) hsa-miR-21-5p | 0.84 (0.84, 0.85) has-miR-142-5p | 0.69 (0.68, 0.7) has-let-7g-5p | 0.69 (0.66, 0.7) has-miR-3740-5p |

[1]Best Set criteria: Mean AUC >= 0.65 and select the top 5 markers (if more than 5 markers have mean AUC >= 0.65).
[2]Best set for F0-2 vs F3-4 in SIM 105/106: has-miR-21-5p, has-miR-26b-5p.
[3]Best set for F0-3 vs F4 in SIM 105/106: hsa-miR-142-5p, hsa-miR-99a-5p, hsa-miR-140-5p, hsa-miR-148b-3p, hsa-miR-373-5p.
[4]Best set for F0-2 vs F3 in SIM 105/106: hsa-let-7g-5p, hsa-miR-26b-5p, hsa-miR-374a-5p, hsa-miR-106b-5p, hsa-miR-193a-5p.
[5]Best set for F1-2 vs F3-4 in SEL 1497: hsa-miR-374a-5p, hsa-let-7c-5p, hsa-let-7a-5p, hsa-miR-26a-5p, has-miR-33a-5p.

We evaluated miRs differentially expressed between F0 Vs F1-4 and identified 56 miRs that were significantly different between the two groups. We also evaluated miRs differentially expressed between F4 vs F0-3 and identified 86 significant miRs. We also evaluated miRs associated with Fibrosis stages F1-2 Vs F3-4 at Baseline and W48.

TABLE 10

| | | Baseline | | |
|---|---|---|---|---|
| miRNA | FC | CI | AUC | p-value |
| hsa-miR-21-5p | 1.21 | (1.129, 1.291) | 0.74 | 0.0000 |
| hsa-miR-26b-5p | 0.78 | (0.688, 0.881) | 0.67 | 0.0000 |
| hsa-miR-140-5p | 1.19 | (1.091, 1.304) | 0.66 | 0.0001 |
| hsa-miR-200a-3p | 1.37 | (1.143, 1.653) | 0.64 | 0.0008 |
| hsa-miR-142-5p | 1.18 | (1.069, 1.312) | 0.63 | 0.001 |

In this study we identified miRs to detect fibrosis stage: 56 miRs can significantly differentiate between F0 vs F1-4 stages of fibrosis at BL in 105/106 studies and 86 miRs can significantly differentiate between F4 vs F0-3 stages of fibrosis at BL in 105/106 studies. We also found that 5 miRs at BL and 5 miRs at W48 can significantly differentiate between F1-2 vs F3-4 stages of fibrosis in 105/106 studies. Some of the liver sourced miRs such as miRs-122-5p, miR-99a-5p and miR-34a-5p are correlated with other biomarkers such as CK-18 M65, CK18M30, ALT and AST.

Example 4

Male C57BL/6 mice were administered either control diet (Teklad Global Diet® 2014, Envigo, Indianapolis, Ind.) or commercially available high-fat, high-cholesterol (0.2%) diet (DB 12079B, Research Diets, Inc, New Brunswick, N.J.) with glucose 17.2 g/L and fructose 23.1 g/L in drinking water (FFD). After 280 days, a cohort of FFD-fed mice were administered a selective small-molecule ASK1 inhibitor analog of selonsertib; 0.15% diet admixture) for 90 d. Plasma was collected for miR analysis at the end of the study from lean and FFD mice administered with ASK1i or vehicle control.

Plasma miRNAs were measured by quantitative polymerase chain reaction using miRnome mouse and rat ready-to-use panel (Exiqon A/S, Vedbaek, Denmark); miR panel consisted of 752 miR primer probes. Differential expression levels of miRNAs were calculated using the comparative threshold cycle method (−ΔΔCt), with p-values assessed using Wilcoxon rank test miRNA levels were normalized against 4 derived miRNAs based on their stable expression in all cohorts in the study. MiRNAs with a minimum 2-fold difference in expression and p-value≤0.05 between groups were selected for further analysis; Spearman's correlation coefficient (ρ) was used to evaluate correlations between miR and other measurements 63 plasma miRs were significantly altered by ASK1 inhibition compared with vehicle control group. Table 13 summarizes the fold change, p-value for miRs that are altered by ASK1 inhibition. A fold change greater than 1 generally shows an increase in miR concentration, whereas a fold change less than 1 generally shows a decrease in miR concentration. The p-value describes the statistical significance of the difference in the quantity of miR altered by ASK1 inhibition (i.e. the significance of the fold change).

TABLE 13

Murine miRNA modulated by ASK1 inhibition

| miRNA | Fold change | p values |
|---|---|---|
| mmu-miR-434-5p | 3.51 | 0.046 |
| mmu-miR-330-5p | 2.85 | 0.04 |
| mmu-miR-669d-5p | 2.67 | 0.035 |
| mmu-miR-30b-5p | −2.02 | 0.002 |
| mmu-miR-203-3p | −2.15 | 0.009 |
| mmu-miR-31-5p | −2.21 | 0.011 |
| mmu-miR-1961 | −2.24 | 0.036 |
| mmu-miR-29a-3p | −2.29 | 0.005 |
| mmu-miR-874-3p | −2.3 | 0.004 |
| mmu-miR-99a-5p | −2.32 | 0.007 |
| mmu-miR-125b-5p | −2.38 | 0.029 |
| mmu-miR-149-5p | −2.41 | 0.007 |
| mmu-miR-30a-5p | −2.42 | 0.005 |
| mmu-miR-152-3p | −2.44 | 0.003 |
| mmu-miR-362-3p | −2.45 | 0.035 |
| mmu-miR-378a-5p | −2.54 | 0.004 |

TABLE 13-continued

Murine miRNA modulated by ASK1 inhibition

| miRNA | Fold change | p values |
|---|---|---|
| mmu-miR-130a-3p | −2.56 | 0 |
| mmu-miR-30a-3p | −2.56 | 0.005 |
| mmu-miR-29b-3p | −2.6 | 0.019 |
| mmu-miR-378a-3p | −2.66 | 0.003 |
| mmu-miR-30e-3p | −2.67 | 0.011 |
| mmu-let-7a-1-3p | −2.71 | 0.004 |
| mmu-miR-32-5p | −2.72 | 0.035 |
| mmu-let-7f-1-3p | −2.76 | 0.002 |
| mmu-miR-101a-3p | −2.84 | 0.005 |
| mmu-miR-331-3p | −3.03 | 0.009 |
| mmu-miR-22-5p | −3.07 | 0.002 |
| mmu-miR-671-5p | −3.26 | 0.001 |
| mmu-miR-101b-3p | −3.29 | 0.002 |
| mmu-miR-28a-3p | −3.4 | 0.005 |
| mmu-miR-22-3p | −3.4 | 0 |
| mmu-miR-194-5p | −3.45 | 0.005 |
| mmu-miR-29c-3p | −3.49 | 0.001 |
| mmu-miR-192-5p | −3.63 | 0.001 |
| mmu-miR-1249-3p | −3.63 | 0.023 |
| mmu-miR-2137 | −3.75 | 0 |
| mmu-miR-676-3p | −3.79 | 0.001 |
| mmu-miR-365-3p | −3.8 | 0.001 |
| mmu-miR-34a-5p | −3.85 | 0.007 |
| mmu-miR-744-3p | −3.96 | 0.011 |
| mmu-miR-145a-3p | −4 | 0.006 |
| mmu-miR-148a-3p | −4.02 | 0.002 |
| mmu-let-7f-2-3p | −4.02 | 0.011 |
| mmu-miR-676-5p | −4.12 | 0.015 |
| mmu-miR-192-3p | −4.15 | 0.001 |
| mmu-miR-137-3p | −4.19 | 0.043 |
| mmu-miR-1247-5p | −4.25 | 0.002 |
| mmu-miR-1839-3p | −4.28 | 0.026 |
| mmu-miR-31-3p | −4.29 | 0.003 |
| mmu-miR-671-3p | −4.75 | 0.045 |
| mmu-miR-30d-3p | −4.96 | 0.004 |
| mmu-miR-455-5p | −5.43 | 0.001 |
| mmu-miR-122-5p | −5.58 | 0.005 |
| mmu-miR-101a-5p | −5.68 | 0.004 |
| mmu-miR-194-2-3p | −6.02 | 0.006 |
| mmu-miR-26b-3p | −6.09 | 0.007 |
| mmu-miR-802-5p | −6.36 | 0.002 |
| mmu-miR-1195 | −6.8 | 0.024 |
| mmu-miR-188-3p | −8.53 | 0.008 |
| mmu-miR-193a-3p | −8.71 | 0.003 |
| mmu-miR-455-3p | −8.92 | 0.017 |
| mmu-let-7g-3p | −9.11 | 0.002 |
| mmu-miR-148a-5p | −9.36 | 0.004 |

TABLE 14

Murine SEQ ID correspondence table

| SEQ ID # | microRNA-previous ID | Sequence |
|---|---|---|
| SEQ ID NO: 98 | mmu-miR-330-5p | UCUCUGGGCCUGUGUCUUAGGC |
| SEQ ID NO: 99 | mmu-miR-30b-5p | UGUAAACAUCCUACACUCAGCU |
| SEQ ID NO: 100 | mmu-miR-31-5p | AGGCAAGAUGCUGGCAUAGCUG |
| SEQ ID NO: 69 | mmu-miR-29a-3p | UAGCACCAUCUGAAAUCGGUUA |
| SEQ ID NO: 101 | mmu-miR-874-3p | CUGCCCUGGCCCGAGGGACCGA |
| SEQ ID NO: 102 | mmu-miR-99a-5p | AACCCGUAGAUCCGAUCUUGUG |
| SEQ ID NO: 25 | mmu-miR-125b-5p | UCCCUGAGACCCUAACUUGUGA |
| SEQ ID NO: 103 | mmu-miR-149-5p | UCUGGCUCCGUGUCUUCACUCCC |
| SEQ ID NO: 41 | mmu-miR-30a-5p | UGUAAACAUCCUCGACUGGAAG |

TABLE 14-continued

Murine SEQ ID correspondence table

| SEQ ID # | microRNA-previous ID | Sequence |
|---|---|---|
| SEQ ID NO: 104 | mmu-miR-152-3p | UCAGUGCAUGACAGAACUUGG |
| SEQ ID NO: 105 | mmu-miR-362-3p | AACACACCUGUUCAAGGAUUCA |
| SEQ ID NO: 106 | mmu-miR-378a-5p | CUCCUGACUCCAGGUCCUGUGU |
| SEQ ID NO: 107 | mmu-miR-130a-3p | CAGUGCAAUGUUAAAAGGGCAU |
| SEQ ID NO: 108 | mmu-miR-30a-3p | CUUUCAGUCGGAUGUUUGCAGC |
| SEQ ID NO: 109 | mmu-miR-29b-3p | UAGCACCAUUUGAAAUCAGUGUU |
| SEQ ID NO: 85 | mmu-miR-378a-3p | ACUGGACUUGGAGUCAGAAGG |
| SEQ ID NO: 110 | mmu-miR-30e-3p | CUUUCAGUCGGAUGUUUACAGC |
| SEQ ID NO: 111 | mmu-miR-32-5p | UAUUGCACAUUACUAAGUUGCA |
| SEQ ID NO: 112 | mmu-let-7f-1-3p | CUAUACAAUCUAUUGCCUUCCC |
| SEQ ID NO: 113 | mmu-miR-331-3p | GCCCCUGGGCCUAUCCUAGAA |
| SEQ ID NO: 114 | mmu-miR-22-5p | AGUUCUUCAGUGGCAAGCUUUA |
| SEQ ID NO: 115 | mmu-miR-671-5p | AGGAAGCCCUGGAGGGGCUGGAG |
| SEQ ID NO: 84 | mmu-miR-22-3p | AAGCUGCCAGUUGAAGAACUGU |
| SEQ ID NO: 116 | mmu-miR-194-5p | UGUAACAGCAACUCCAUGUGGA |
| SEQ ID NO: 117 | mmu-miR-29c-3p | UAGCACCAUUUGAAAUCGGUUA |
| SEQ ID NO: 67 | mmu-miR-192-5p | CUGACCUAUGAAUUGACAGCC |
| SEQ ID NO: 118 | mmu-miR-1249-3p | ACGCCCUUCCCCCCCUUCUUCA |
| SEQ ID NO: 119 | mmu-miR-676-3p | CCGUCCUGAGGUUGUUGAGCU |
| SEQ ID NO: 26 | mmu-miR-34a-5p | UGGCAGUGUCUUAGCUGGUUGU |
| SEQ ID NO: 120 | mmu-miR-744-3p | CUGUUGCCACUAACCUCAACCU |
| SEQ ID NO: 15 | mmu-miR-148a-3p | UCAGUGCACUACAGAACUUUGU |
| SEQ ID NO: 121 | mmu-let-7f-2-3p | CUAUACAGUCUACUGUCUUUC |
| SEQ ID NO: 122 | mmu-miR-676-5p | ACUCUACAACCUUAGGACUUGC |
| SEQ ID NO: 123 | mmu-miR-192-3p | CUGCCAAUUCCAUAGGUCACAG |
| SEQ ID NO: 124 | mmu-miR-1247-5p | ACCCGUCCCGUUCGUCCCCGGA |
| SEQ ID NO: 125 | mmu-miR-31-3p | UGCUAUGCCAACAUAUUGCCAUC |
| SEQ ID NO: 126 | mmu-miR-671-3p | UCCGGUUCUCAGGGCUCCACC |
| SEQ ID NO: 127 | mmu-miR-30d-3p | CUUUCAGUCAGAUGUUUGCUGC |
| SEQ ID NO: 128 | mmu-miR-455-5p | UAUGUGCCUUUGGACUACAUCG |
| SEQ ID NO: 61 | mmu-miR-122-5p | UGGAGUGUGACAAUGGUGUUUG |
| SEQ ID NO: 129 | mmu-miR-26b-3p | CCUGUUCUCCAUUACUUGGCUC |
| SEQ ID NO: 130 | mmu-miR-188-3p | CUCCCACAUGCAGGGUUUGCA |
| SEQ ID NO: 131 | mmu-miR-193a-3p | AACUGGCCUACAAAGUCCCAGU |
| SEQ ID NO: 132 | mmu-miR-455-3p | GCAGUCCACGGGCAUAUACAC |
| SEQ ID NO: 133 | mmu-let-7g-3p | ACUGUACAGGCCACUGCCUUGC |
| SEQ ID NO: 134 | mmu-miR-148a-5p | AAAGUUCUGAGACACUCCGACU |

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of treating nonalcoholic steatohepatitis (NASH) in a human, the method comprising:
   (a) detecting in a sample from the human increased levels of one or more microRNAs (miRNAs) selected from the group consisting of hsa-miR-34a-p and hsa-miR-122-p, and
   (b) administering an apoptosis signal-regulating kinase 1 (ASK1) inhibitor to the human.

2. A method of treating nonalcoholic steatohepatitis (NASH) in a human in need thereof, comprising:
   (a) detecting in a sample from the human increased levels of miRNAs hsa-miR-34a-p and hsa-miR-122-p, wherein the human has NASH, is suspected of having NASH, or has a risk for NASH, and wherein the human has a nonalcoholic fatty liver disease (NAFLD) Activity Score (NAS) of 5 or above; and
   (b) administering an apoptosis signal-regulating kinase 1 (ASK1) inhibitor.

3. The method of claim 1 or claim 2, further comprising performing a magnetic resonance elastography (MRE) on the human.

4. The method of claim 1 or claim 2, wherein the human has liver fibrosis.

5. The method of claim 4, wherein the stage of the liver fibrosis is not determined.

6. The method of claim 1 or claim 2, wherein the human has liver inflammation.

7. The method of claim 1, wherein the human has a nonalcoholic fatty liver disease (NAFLD Activity Score (NAS) of 5 or above.

8. The method of claim 1 or claim 2, wherein the human has three or more features of metabolic syndrome, wherein the metabolic syndrome comprises elevated blood pressure, abdominal obesity, elevated fasting plasma glucose, high serum triglycerides, low high-density lipoprotein cholesterol or any combination thereof.

9. The method of claim 1 or claim 2, wherein the human has a serum alanine aminotransferase (ALT) level between 1.5-fold to 5-fold of upper limit of normal (ULN).

10. The method of claim 1 or claim 2, wherein the human has a liver stiffness by FibroScan (Echosens®, Paris, France) of between 7 kPa and 12 kPa.

11. A method of treating nonalcoholic steatohepatitis (NASH) in a human, the method comprising:
    administering an apoptosis signal-regulating kinase 1 (ASK1) inhibitor to the human,
    wherein the human has been identified as having an increase in the levels of miRNAs hsa-miR-134-p and hsa-miR-122-p.

12. The method of any one of claim 1, 2 or 11, wherein the increase is identified by comparing one or more of the levels of the one or more miRNAs in a second sample from the human to one or more of the levels of the one or more miRNAs in a first sample from the human.

13. The method of any one of claim 1, 2 or 11, wherein the increase is identified by comparing one or more of the levels of the one or more miRNAs in a first sample from the human to control levels of the one or more miRNAs.

14. The method of claim 13, wherein the control levels of the one or more miRNAs are the levels of the one or more miRNAs in one or more control samples.

15. The method of any one of claim 1, 2 or 11, further comprising detecting increased levels of hsa-miR-1260b.

16. The method of any one of claim 1, 2 or 11, further comprising detecting the levels of one or more miRNAs selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, and hsa-miR-132.

17. The method of any one of claim 1, 2 or 11, further comprising detecting the levels of one or more miRNAs selected from the group consisting of hsa-miR-15b, hsa-miR-17, hsa-miR-451, hsa-miR-15a, hsa-miR-20b, hsa-miR-16, hsa-miR-195, hsa-miR-25, hsa-miR-320b, hsa-miR-320c, hsa-miR-101, hsa-miR-21, hsa-miR-150, hsa-miR-20a, hsa-miR-148a, hsa-miR-191, hsa-miR-106a, hsa-miR-24, hsa-miR-26b, hsa-miR-424, hsa-miR-483-3p, hsa-miR-499-3p, hsa-miR-181d, hsa-miR-124, hsa-miR-125b, hsa-miR-34a, hsa-miR-362-5p, hsa-miR-512-3p, hsa-miR-485-3p, hsa-miR-132, hsa-miR-92a, hsa-let-7b, hsa-miR-19b, hsa-miR-93, hsa-miR-19a, hsa-miR-142-3p, hsa-let-7e, hsa-miR-223, hsa-miR-148b, hsa-miR-30e, hsa-miR-30a, hsa-miR-26a, hsa-let-7a, hsa-miR-30d, hsa-miR-18b, hsa-miR-92b, hsa-miR-135a, hsa-miR-135b, hsa-miR-375, hsa-miR-181a, hsa-miR-346, hsa-miR-181c, hsa-miR-539, hsa-miR-320d, hsa-miR-523, hsa-miR-28-3p, hsa-miR-219-1-3p, hsa-miR-323-5p, hsa-miR-339-3p, hsa-miR-324-3p, hsa-miR-27a, hsa-let-7g, hsa-miR-486-5p, hsa-miR-425, hsa-let-7c, hsa-miR-192, hsa-miR-18a, hsa-miR-29a, hsa-miR-27b, hsa-let-7f, hsa-miR-151-5p, hsa-let-7d, hsa-miR-146a, hsa-miR-423-5p, hsa-miR-103, hsa-miR-30c, hsa-miR-23a, hsa-miR-106b, hsa-miR-23b, hsa-miR-151-3p, hsa-miR-185, hsa-miR-199a-3p, hsa-miR-22, hsa-miR-378, hsa-miR-28-5p, hsa-miR-370, hsa-miR-34c-3p, hsa-miR-181b, hsa-miR-493, hsa-miR-10a, hsa-miR-10b, hsa-miR-139-5p, hsa-miR-326, hsa-miR-423-3p, hsa-miR-187, hsa-miR-127-3p, hsa-miR-136-5p, hsa-miR-30a-5p, hsa-miR-29c-3p, hsa-miR-378a-3p, hsa-miR-99a-5p, hsa-miR-1260b, hsa-miR-365a-3p, hsa-miR-215-5p, hsa-miR-194-5p, hsa-let-7i-5p, hsa-miR-222-3p, hsa-miR-365a-3p, hsa-miR-22-5p, hsa-miR-505-3p, hsa-miR-885-5p, hsa-miR-107, hsa-miR-100-5p, hsa-miR-155-5p, and hsa-miR-874-3p.

18. The method of any one of claim 1, 2 or 11, further comprising evaluating one or more liver disease or condition correlates selected from the group consisting of: adiponectin, age, alanine aminotransferase (ALT), albumin, alpha 2 macroglobulin (A2M), apolipoprotein B (ApoB)/apolipoprotein A1 (ApoA1) ratio, aspartate aminotransferase (AST), bilirubin, body mass index (BMI); collagen type IV, al chain, degradation fragment (C4M2); cholesterol, C-reactive protein (CRP), cytokeratin-18 (CK-18), diabetes, blood glucose, glycated hemoglobin (Hb Ac1), haptogobin, hepatocellular ballooning, Homeostatic Model Assessment-Insulin Resistance (HOMA-IR), hyaluronic acid (HA), impaired fasting glycemia (IFG), Insulin, liver biopsy, lobular inflammation, Lumican (LUM), Lysyl Oxidase Like 2 (sLOXL2), macroglobulin, Magnetic Resonance Elastography (MRE), Magnetic Resonance Imaging-Estimated Proton Density Fat Fraction (MRI-PDFF), collagen type IV formation fragment (P4NP7S), Plasma Pro-C3 (N-terminal type III collagen propeptide), platelet count, procollagen type III-terminal peptide (PIIINP), prothrombin time, steatosis, tissue inhibitor of metalloproteinases-1 (TIMP-1), Transforming Growth Factor Beta-Induced Protein (TGFBI), transient elastography (Liver Stiffness), triglycerides, urea, waist:hip ratio, γ-glutamyl transferase (GGT), and combination(s) thereof.

19. The method of any one of claim 1, 2 or 11, wherein the sample is selected from the group consisting of bile, blood, blood plasma, serum, breast milk, feces, pus, saliva, sebum, semen, sweat, tears, urine, and vomit.

20. The method of any one of claim 1, 2 or 11, further comprising evaluating the liver disease or condition according to one or more scoring systems selected from the group consisting of: Fibrosis-4 (FIB-4), BAAT (Body Mass Index, Age at liver biopsy, Alanine aminotransferase, and serum Triglycerides), Non-Alcoholic Fatty Liver Disease (NAFLD) Fibrosis Score (NFS), BARD (Body Mass Index, Aspartate Aminotransferase/Alanine Aminotransferase Ratio, Diabetes), Enhanced Liver Fibrosis (ELF®), Fibrosure Fibrotest®, Fibrometer®, or Fibroscan®, AST to Platelet Ratio Index (APRI), and combination(s) thereof.

21. The method claim 4, wherein the human has fibrosis stage F1 to F2.

22. The method claim 4, wherein the human has fibrosis stage F2 to F3.

23. The method claim 4, wherein the human has fibrosis stage F3 to F4.

24. The method of any one of claim 1, 2 or 11, wherein the apoptosis signal-regulating kinase 1 (ASK1) inhibitor comprises selonsertib.

25. The method of any one of claim 1, 2 or 11, further comprising administering to the human one or more therapeutic agents selected from the group consisting of:
    an ACE inhibitor;
    an Acetyl CoA carboxylase (ACC) inhibitor;
    an Adenosine receptor agonist;
    an Adiponectin receptor agonist;
    an Amylin/calcitonin receptor agonist;
    an AMP activated protein kinase stimulator;

an Angiotensin II AT-1 receptor antagonist;
an Autotaxin inhibitor;
a Bioactive lipid;
a Cannabinoid receptor type 1 (CNR1) inhibitors;
a Caspase inhibitor;
a cathepsin B inhibitor;
a pan cathepsin inhibitor;
a CCR2/CCR5 chemokine antagonist;
a CCR2 chemokine antagonist;
a CCR3 chemokine antagonist;
a Chloride channel stimulator;
a Diglyceride acyltransferase 2 (DGAT2) inhibitor;
a Dipeptidyl peptidase IV inhibitor;
an Eotaxin ligand inhibitor;
an Extracellular matrix protein modulator;
a Farnesoid X receptor (FXR) agonist;
a Farnesoid X receptor (FXR)/G-protein coupled bile acid receptor 1(TGR5) agonist;
a Fatty acid synthase inhibitor;
a Fibroblast growth factor 19 (rhFGF19)/cytochrome P450 (CYP) 7A1 inhibitor;
a Fibroblast growth factor 21(FGF-21) ligand;
a Fibroblast growth factor 21(FGF-21)/glucagon like peptide 1 (GLP-1) agonist;
a Galectin-3 inhibitor;
a Glucagon-like peptide 1(GLP1R) agonists;
a G-protein coupled bile acid receptor 1(TGR5) agonists;
a Heat shock protein 47 (HSP47) inhibitor;
a HMG CoA reductase inhibitor;
an IL-10 agonist;
an Ileal sodium bile acid cotransporter inhibitor;
an Insulin sensitizer;
a beta Klotho (KLB)-FGF1c agonist;
a 5-Lipoxygenase inhibitors;
a Lipoprotein lipase inhibitors;
a LPL gene stimulators;
a Liver X receptor (LXR) inhibitor;
a Lysophosphatidate-1 receptor antagonist;
a Lysyl oxidase homolog 2 inhibitor;
a Semicarbazide-Sensitive Amine Oxidase/Vascular Adhesion Protein-1 (SSAO/VAP-1) Inhibitor;
a Methionine aminopeptidase-2 inhibitor;
a Methyl CpG binding protein 2 modulator;
a Mitochondrial uncoupler;
a Myelin basic protein stimulator;
a NADPH oxidase 1/4 inhibitor;
a Nicotinic acid receptor 1 agonist;
a NACHT LRR PYD domain protein 3 (NLRP3) inhibitor;
a Nuclear receptor modulator;
a P2Y13 purinoceptor stimulator;
a PDE 3/4 inhibitor;
a PDE 5 inhibitor;
a PDGF receptor beta modulator;
a PPAR agonist;
a Protease-activated receptor-2 antagonist;
a Protein kinase modulator;
a Rho associated protein kinase (ROCK) inhibitor;
a Sodium glucose transporter-2(SGLT2) inhibitor;
a SREBP transcription factor inhibitor;
a Stearoyl CoA desaturase-1 inhibitor;
a Thyroid hormone receptor beta agonist;
a TLR-4 antagonist;
a Tyrosine kinase receptor modulator;
a GPCR modulator; and
a Nuclear hormone receptor modulator.

26. The method of any one of claim 1, 2 or 11, further comprising administering to the human one or more therapeutic agents selected from the group consisting of:
an Acetyl CoA carboxylase (ACC) inhibitor;
a Farnesoid X receptor (FXR) agonist; and
a Lysyl oxidase homolog 2 inhibitor.

27. The method of any one of claim 1, 2 or 11, further comprising administering to the human one or more therapeutic agents selected from the group consisting of: simtuzumab (SIM); GS-9674; GS-0976; A-4250, AC-3174, acetylsalicylic acid, AK-20, alipogene tiparvovec, aramchol, ARI-3037M0, ASP-8232, bertilimumab, Betaine anhydrous, BI-1467335, BMS-986036, BMS-986171, BMT-053011, BOT-191, BTT-1023, CAT-2003, cenicriviroc, CER-209, CF-102, CGS21680, CNX-014, CNX-023, CNX-024, CNX-025, cobiprostone, colesevelam, dapagliflozin, deuterated pioglitazone R-enantiomer, 2,4-dinitrophenol, DRX-065, DS-102, DUR-928, EDP-305, elafibranor (GFT-505), emricasan, enalapril, ertugliflozin, evogliptin, F-351, GKT-831, GNF-5120, GR-MD-02, hydrochlorothiazide, icosapent ethyl ester, IMM-124-E, INT-767, IONIS-DGAT2Rx, ipragliflozin, Irbesarta, propagermanium, IVA-337, JKB-121, KB-GE-001, KBP-042, KD-025, M790, M780, M450, metformin, sildenafil, LC-280126, linagliptin, liraglutide, LJN-452, LMB-763, MBX-8025, MDV-4463, mercaptamine, MGL-3196, MGL-3745, MSDC-0602K, namacizumab, NC-101, NDI-010976, ND-L02-s0201, NGM-282, NGM-313, NGM-386, NGM-395, norursodeoxycholic acid, 0-304, obeticholic acid, 25HC3S, olesoxime, PAT-505, PAT-048, PEG-ilodecakin, pioglitazone, pirfenidone, PRI-724, PX20606, Px-102, PX-L603, PX-L493, PXS-4728A, PZ-235, RDX-009, remogliflozin etabonate, RG-125 (AZD4076), saroglitazar, semaglutide, solithromycin, sotagliflozin, a statin, TCM-606F, TEV-45478, tipelukast (MN-001), TLY-012, TRX-318, TVB-2640, UD-009, ursodeoxycholic acid, VBY-376, VBY-825, VK-2809, vismodegib, volixibat potassium ethanolate hydrate (SHP-626), VVP-100X, WAV-301, WNT-974, and ZGN-839.

28. The method of any one of claim 1, 2 or 11, further comprising administering to the human one or more therapeutic agents selected from the group consisting of: simtuzumab (SIM); GS-9674 and GS-0976.

* * * * *

```
                           SEQUENCE LISTING

<160> NUMBER OF SEQ ID NOS: 149

<210> SEQ ID NO 1
<211> LENGTH: 22
<212> TYPE: RNA
<213> ORGANISM: Homo sapiens

<400> SEQUENCE: 1
uagcagcaca ucaugguuua ca                                               22

<210> SEQ ID NO 2
<211> LENGTH: 23
<212> TYPE: RNA
<213> ORGANISM: Homo sapiens

<400> SEQUENCE: 2
caaagugcuu acagugcagg uag                                              23

<210> SEQ ID NO 3
<211> LENGTH: 22
<212> TYPE: RNA
<213> ORGANISM: Homo sapiens

<400> SEQUENCE: 3
aaaccguuac cauuacugag uu                                               22

<210> SEQ ID NO 4
<211> LENGTH: 22
<212> TYPE: RNA
<213> ORGANISM: Homo sapiens

<400> SEQUENCE: 4
uagcagcaca uaaugguuug ug                                               22

<210> SEQ ID NO 5
<211> LENGTH: 23
<212> TYPE: RNA
<213> ORGANISM: Homo sapiens

<400> SEQUENCE: 5
caaagugcuc auagugcagg uag                                              23

<210> SEQ ID NO 6
<211> LENGTH: 22
<212> TYPE: RNA
<213> ORGANISM: Homo sapiens

<400> SEQUENCE: 6
uagcagcacg uaaauauugg cg                                               22

<210> SEQ ID NO 7
<211> LENGTH: 21
<212> TYPE: RNA
<213> ORGANISM: Homo sapiens

<400> SEQUENCE: 7
uagcagcaca gaaauauugg c                                                21
```

```
<210> SEQ ID NO 8
<211> LENGTH: 22
<212> TYPE: RNA
<213> ORGANISM: Homo sapiens

<400> SEQUENCE: 8
cauugcacuu gucucggucu ga                                              22

<210> SEQ ID NO 9
<211> LENGTH: 22
<212> TYPE: RNA
<213> ORGANISM: Homo sapiens

<400> SEQUENCE: 9
aaaagcuggg uugagagggc aa                                              22

<210> SEQ ID NO 10
<211> LENGTH: 20
<212> TYPE: RNA
<213> ORGANISM: Homo sapiens

<400> SEQUENCE: 10
aaaagcuggg uugagagggu                                                 20

<210> SEQ ID NO 11
<211> LENGTH: 21
<212> TYPE: RNA
<213> ORGANISM: Homo sapiens

<400> SEQUENCE: 11
uacaguacug ugauaacuga a                                               21

<210> SEQ ID NO 12
<211> LENGTH: 22
<212> TYPE: RNA
<213> ORGANISM: Homo sapiens

<400> SEQUENCE: 12
uagcuuauca gacugauguu ga                                              22

<210> SEQ ID NO 13
<211> LENGTH: 22
<212> TYPE: RNA
<213> ORGANISM: Homo sapiens

<400> SEQUENCE: 13
ucucccaacc cuuguaccag ug                                              22

<210> SEQ ID NO 14
<211> LENGTH: 23
<212> TYPE: RNA
<213> ORGANISM: Homo sapiens

<400> SEQUENCE: 14
uaaagugcuu auagugcagg uag                                             23

<210> SEQ ID NO 15
<211> LENGTH: 22
<212> TYPE: RNA
<213> ORGANISM: Homo sapiens

<400> SEQUENCE: 15
ucagugcacu acagaacuuu gu                                              22
```

```
<210> SEQ ID NO 16
<211> LENGTH: 23
<212> TYPE: RNA
<213> ORGANISM: Homo sapiens

<400> SEQUENCE: 16
caacggaauc ccaaaagcag cug                                              23

<210> SEQ ID NO 17
<211> LENGTH: 23
<212> TYPE: RNA
<213> ORGANISM: Homo sapiens

<400> SEQUENCE: 17
aaaagugcuu acagugcagg uag                                              23

<210> SEQ ID NO 18
<211> LENGTH: 22
<212> TYPE: RNA
<213> ORGANISM: Homo sapiens

<400> SEQUENCE: 18
uggcucaguu cagcaggaac ag                                               22

<210> SEQ ID NO 19
<211> LENGTH: 21
<212> TYPE: RNA
<213> ORGANISM: Homo sapiens

<400> SEQUENCE: 19
uucaaguaau ucaggauagg u                                                21

<210> SEQ ID NO 20
<211> LENGTH: 22
<212> TYPE: RNA
<213> ORGANISM: Homo sapiens

<400> SEQUENCE: 20
cagcagcaau ucauguuuug aa                                               22

<210> SEQ ID NO 21
<211> LENGTH: 21
<212> TYPE: RNA
<213> ORGANISM: Homo sapiens

<400> SEQUENCE: 21
ucacuccucu ccucccgucu u                                                21

<210> SEQ ID NO 22
<211> LENGTH: 22
<212> TYPE: RNA
<213> ORGANISM: Homo sapiens

<400> SEQUENCE: 22
aacaucacag caagucugug cu                                               22

<210> SEQ ID NO 23
<211> LENGTH: 23
<212> TYPE: RNA
<213> ORGANISM: Homo sapiens

<400> SEQUENCE: 23
aacauucauu guugucggug ggu                                              23
```

```
<210> SEQ ID NO 24
<211> LENGTH: 20
<212> TYPE: RNA
<213> ORGANISM: Homo sapiens

<400> SEQUENCE: 24
uaaggcacgc ggugaaugcc                                              20

<210> SEQ ID NO 25
<211> LENGTH: 22
<212> TYPE: RNA
<213> ORGANISM: Homo sapiens

<400> SEQUENCE: 25
ucccugagac ccuaacuugu ga                                           22

<210> SEQ ID NO 26
<211> LENGTH: 22
<212> TYPE: RNA
<213> ORGANISM: Homo sapiens

<400> SEQUENCE: 26
uggcaguguc uuagcugguu gu                                           22

<210> SEQ ID NO 27
<211> LENGTH: 24
<212> TYPE: RNA
<213> ORGANISM: Homo sapiens

<400> SEQUENCE: 27
aauccuugga accuaggugu gagu                                         24

<210> SEQ ID NO 28
<211> LENGTH: 22
<212> TYPE: RNA
<213> ORGANISM: Homo sapiens

<400> SEQUENCE: 28
aagugcuguc auagcugagg uc                                           22

<210> SEQ ID NO 29
<211> LENGTH: 22
<212> TYPE: RNA
<213> ORGANISM: Homo sapiens

<400> SEQUENCE: 29
gucauacacg gcucuccucu cu                                           22

<210> SEQ ID NO 30
<211> LENGTH: 22
<212> TYPE: RNA
<213> ORGANISM: Homo sapiens

<400> SEQUENCE: 30
uaacagucua cagccauggu cg                                           22

<210> SEQ ID NO 31
<211> LENGTH: 22
<212> TYPE: RNA
<213> ORGANISM: Homo sapiens

<400> SEQUENCE: 31
uauugcacuc gucccggccu cc                                           22
```

```
<210> SEQ ID NO 32
<211> LENGTH: 22
<212> TYPE: RNA
<213> ORGANISM: Homo sapiens

<400> SEQUENCE: 32
ugagguagua gguugugugg uu                                              22

<210> SEQ ID NO 33
<211> LENGTH: 23
<212> TYPE: RNA
<213> ORGANISM: Homo sapiens

<400> SEQUENCE: 33
ugugcaaauc caugcaaaac uga                                             23

<210> SEQ ID NO 34
<211> LENGTH: 23
<212> TYPE: RNA
<213> ORGANISM: Homo sapiens

<400> SEQUENCE: 34
caaagugcug uucgugcagg uag                                             23

<210> SEQ ID NO 35
<211> LENGTH: 23
<212> TYPE: RNA
<213> ORGANISM: Homo sapiens

<400> SEQUENCE: 35
ugugcaaauc uaugcaaaac uga                                             23

<210> SEQ ID NO 36
<211> LENGTH: 23
<212> TYPE: RNA
<213> ORGANISM: Homo sapiens

<400> SEQUENCE: 36
uguaguguuu ccuacuuuau gga                                             23

<210> SEQ ID NO 37
<211> LENGTH: 22
<212> TYPE: RNA
<213> ORGANISM: Homo sapiens

<400> SEQUENCE: 37
ugagguagga gguuguauag uu                                              22

<210> SEQ ID NO 38
<211> LENGTH: 22
<212> TYPE: RNA
<213> ORGANISM: Homo sapiens

<400> SEQUENCE: 38
ugucaguuug ucaaauaccc ca                                              22

<210> SEQ ID NO 39
<211> LENGTH: 22
<212> TYPE: RNA
<213> ORGANISM: Homo sapiens

<400> SEQUENCE: 39
ucagugcauc acagaacuuu gu                                              22
```

```
<210> SEQ ID NO 40
<211> LENGTH: 22
<212> TYPE: RNA
<213> ORGANISM: Homo sapiens

<400> SEQUENCE: 40
uguaaacauc cuugacugga ag                                              22

<210> SEQ ID NO 41
<211> LENGTH: 22
<212> TYPE: RNA
<213> ORGANISM: Homo sapiens

<400> SEQUENCE: 41
uguaaacauc cucgacugga ag                                              22

<210> SEQ ID NO 42
<211> LENGTH: 22
<212> TYPE: RNA
<213> ORGANISM: Homo sapiens

<400> SEQUENCE: 42
uucaaguaau ccaggauagg cu                                              22

<210> SEQ ID NO 43
<211> LENGTH: 22
<212> TYPE: RNA
<213> ORGANISM: Homo sapiens

<400> SEQUENCE: 43
ugagguagua gguuguauag uu                                              22

<210> SEQ ID NO 44
<211> LENGTH: 22
<212> TYPE: RNA
<213> ORGANISM: Homo sapiens

<400> SEQUENCE: 44
uguaaacauc cccgacugga ag                                              22

<210> SEQ ID NO 45
<211> LENGTH: 23
<212> TYPE: RNA
<213> ORGANISM: Homo sapiens

<400> SEQUENCE: 45
uaaggugcau cuagugcagu uag                                             23

<210> SEQ ID NO 46
<211> LENGTH: 22
<212> TYPE: RNA
<213> ORGANISM: Homo sapiens

<400> SEQUENCE: 46
uauugcacuc gucccggccu cc                                              22

<210> SEQ ID NO 47
<211> LENGTH: 23
<212> TYPE: RNA
<213> ORGANISM: Homo sapiens

<400> SEQUENCE: 47
uauggcuuuu uauuccuaug uga                                             23
```

```
<210> SEQ ID NO 48
<211> LENGTH: 23
<212> TYPE: RNA
<213> ORGANISM: Homo sapiens

<400> SEQUENCE: 48
uauggcuuuu cauuccuaug uga                                              23

<210> SEQ ID NO 49
<211> LENGTH: 22
<212> TYPE: RNA
<213> ORGANISM: Homo sapiens

<400> SEQUENCE: 49
uuuguucguu cggcucgcgu ga                                               22

<210> SEQ ID NO 50
<211> LENGTH: 23
<212> TYPE: RNA
<213> ORGANISM: Homo sapiens

<400> SEQUENCE: 50
aacauucaac gcugucggug agu                                              23

<210> SEQ ID NO 51
<211> LENGTH: 23
<212> TYPE: RNA
<213> ORGANISM: Homo sapiens

<400> SEQUENCE: 51
ugucugcccg caugccugcc ucu                                              23

<210> SEQ ID NO 52
<211> LENGTH: 22
<212> TYPE: RNA
<213> ORGANISM: Homo sapiens

<400> SEQUENCE: 52
aacauucaac cugucggaga gu                                               22

<210> SEQ ID NO 53
<211> LENGTH: 22
<212> TYPE: RNA
<213> ORGANISM: Homo sapiens

<400> SEQUENCE: 53
ggagaaauua uccuuggugu gu                                               22

<210> SEQ ID NO 54
<211> LENGTH: 19
<212> TYPE: RNA
<213> ORGANISM: Homo sapiens

<400> SEQUENCE: 54
aaaagcuggg uugagagga                                                   19

<210> SEQ ID NO 55
<211> LENGTH: 23
<212> TYPE: RNA
<213> ORGANISM: Homo sapiens

<400> SEQUENCE: 55
gaacgcgcuu cccuauagag ggu                                              23
```

```
<210> SEQ ID NO 56
<211> LENGTH: 22
<212> TYPE: RNA
<213> ORGANISM: Homo sapiens

<400> SEQUENCE: 56
cacuagauug ugagcuccug ga                                              22

<210> SEQ ID NO 57
<211> LENGTH: 22
<212> TYPE: RNA
<213> ORGANISM: Homo sapiens

<400> SEQUENCE: 57
agaguugagu cuggacglucc cg                                             22

<210> SEQ ID NO 58
<211> LENGTH: 22
<212> TYPE: RNA
<213> ORGANISM: Homo sapiens

<400> SEQUENCE: 58
aggugguccg uggcgcguuc gc                                              22

<210> SEQ ID NO 59
<211> LENGTH: 23
<212> TYPE: RNA
<213> ORGANISM: Homo sapiens

<400> SEQUENCE: 59
ugagcgccuc gacgacagag ccg                                             23

<210> SEQ ID NO 60
<211> LENGTH: 20
<212> TYPE: RNA
<213> ORGANISM: Homo sapiens

<400> SEQUENCE: 60
acugccccag gugcugcugg                                                 20

<210> SEQ ID NO 61
<211> LENGTH: 22
<212> TYPE: RNA
<213> ORGANISM: Homo sapiens

<400> SEQUENCE: 61
uggaguguga caauggiuguu ug                                             22

<210> SEQ ID NO 62
<211> LENGTH: 21
<212> TYPE: RNA
<213> ORGANISM: Homo sapiens

<400> SEQUENCE: 62
uucacagugg cuaaguuccg c                                               21

<210> SEQ ID NO 63
<211> LENGTH: 22
<212> TYPE: RNA
<213> ORGANISM: Homo sapiens

<400> SEQUENCE: 63
ugagguagua guuuguacag uu                                              22
```

```
<210> SEQ ID NO 64
<211> LENGTH: 22
<212> TYPE: RNA
<213> ORGANISM: Homo sapiens

<400> SEQUENCE: 64
uccuguacug agcugccccg ag                                              22

<210> SEQ ID NO 65
<211> LENGTH: 23
<212> TYPE: RNA
<213> ORGANISM: Homo sapiens

<400> SEQUENCE: 65
aaugacacga ucacucccgu uga                                             23

<210> SEQ ID NO 66
<211> LENGTH: 22
<212> TYPE: RNA
<213> ORGANISM: Homo sapiens

<400> SEQUENCE: 66
ugagguagua gguuguaugg uu                                              22

<210> SEQ ID NO 67
<211> LENGTH: 21
<212> TYPE: RNA
<213> ORGANISM: Homo sapiens

<400> SEQUENCE: 67
cugaccuaug aauugacagc c                                               21

<210> SEQ ID NO 68
<211> LENGTH: 23
<212> TYPE: RNA
<213> ORGANISM: Homo sapiens

<400> SEQUENCE: 68
uaaggugcau cuagugcaga uag                                             23

<210> SEQ ID NO 69
<211> LENGTH: 22
<212> TYPE: RNA
<213> ORGANISM: Homo sapiens

<400> SEQUENCE: 69
uagcaccauc ugaaaucggu ua                                              22

<210> SEQ ID NO 70
<211> LENGTH: 21
<212> TYPE: RNA
<213> ORGANISM: Homo sapiens

<400> SEQUENCE: 70
uucacagugg cuaaguucug c                                               21

<210> SEQ ID NO 71
<211> LENGTH: 22
<212> TYPE: RNA
<213> ORGANISM: Homo sapiens

<400> SEQUENCE: 71
ugagguagua gauuguauag uu                                              22
```

```
<210> SEQ ID NO 72
<211> LENGTH: 21
<212> TYPE: RNA
<213> ORGANISM: Homo sapiens

<400> SEQUENCE: 72
ucgaggagcu cacagucuag u                                              21

<210> SEQ ID NO 73
<211> LENGTH: 22
<212> TYPE: RNA
<213> ORGANISM: Homo sapiens

<400> SEQUENCE: 73
agagguagua gguugcauag uu                                             22

<210> SEQ ID NO 74
<211> LENGTH: 22
<212> TYPE: RNA
<213> ORGANISM: Homo sapiens

<400> SEQUENCE: 74
ugagaacuga auuccauggg uu                                             22

<210> SEQ ID NO 75
<211> LENGTH: 23
<212> TYPE: RNA
<213> ORGANISM: Homo sapiens

<400> SEQUENCE: 75
ugaggggcag agagcgagac uuu                                            23

<210> SEQ ID NO 76
<211> LENGTH: 23
<212> TYPE: RNA
<213> ORGANISM: Homo sapiens

<400> SEQUENCE: 76
agcagcauug uacagggcua uga                                            23

<210> SEQ ID NO 77
<211> LENGTH: 23
<212> TYPE: RNA
<213> ORGANISM: Homo sapiens

<400> SEQUENCE: 77
uguaaacauc cuacacucuc agc                                            23

<210> SEQ ID NO 78
<211> LENGTH: 21
<212> TYPE: RNA
<213> ORGANISM: Homo sapiens

<400> SEQUENCE: 78
aucacauugc cagggauuuc c                                              21

<210> SEQ ID NO 79
<211> LENGTH: 21
<212> TYPE: RNA
<213> ORGANISM: Homo sapiens

<400> SEQUENCE: 79
uaaagugcug acagugcaga u                                              21
```

```
<210> SEQ ID NO 80
<211> LENGTH: 21
<212> TYPE: RNA
<213> ORGANISM: Homo sapiens

<400> SEQUENCE: 80
aucacauugc cagggauuac c                                             21

<210> SEQ ID NO 81
<211> LENGTH: 21
<212> TYPE: RNA
<213> ORGANISM: Homo sapiens

<400> SEQUENCE: 81
cuagacugaa gcuccuugag g                                             21

<210> SEQ ID NO 82
<211> LENGTH: 22
<212> TYPE: RNA
<213> ORGANISM: Homo sapiens

<400> SEQUENCE: 82
uggagagaaa ggcaguuccu ga                                            22

<210> SEQ ID NO 83
<211> LENGTH: 22
<212> TYPE: RNA
<213> ORGANISM: Homo sapiens

<400> SEQUENCE: 83
acaguagucu gcacauuggu ua                                            22

<210> SEQ ID NO 84
<211> LENGTH: 22
<212> TYPE: RNA
<213> ORGANISM: Homo sapiens

<400> SEQUENCE: 84
aagcugccag uugaagaacu gu                                            22

<210> SEQ ID NO 85
<211> LENGTH: 21
<212> TYPE: RNA
<213> ORGANISM: Homo sapiens

<400> SEQUENCE: 85
acuggacuug gagucagaag g                                             21

<210> SEQ ID NO 86
<211> LENGTH: 22
<212> TYPE: RNA
<213> ORGANISM: Homo sapiens

<400> SEQUENCE: 86
aaggagcuca cagucuauug ag                                            22

<210> SEQ ID NO 87
<211> LENGTH: 22
<212> TYPE: RNA
<213> ORGANISM: Homo sapiens

<400> SEQUENCE: 87
gccugcuggg guggaaccug gu                                            22
```

<210> SEQ ID NO 88
<211> LENGTH: 22
<212> TYPE: RNA
<213> ORGANISM: Homo sapiens

<400> SEQUENCE: 88
aaucacuaac cacacggcca gg                                    22

<210> SEQ ID NO 89
<211> LENGTH: 23
<212> TYPE: RNA
<213> ORGANISM: Homo sapiens

<400> SEQUENCE: 89
aacauucauu gcugucggug ggu                                   23

<210> SEQ ID NO 90
<211> LENGTH: 22
<212> TYPE: RNA
<213> ORGANISM: Homo sapiens

<400> SEQUENCE: 90
ugaaggucua cugugugcca gg                                    22

<210> SEQ ID NO 91
<211> LENGTH: 23
<212> TYPE: RNA
<213> ORGANISM: Homo sapiens

<400> SEQUENCE: 91
uacccuguag auccgaauuu gug                                   23

<210> SEQ ID NO 92
<211> LENGTH: 23
<212> TYPE: RNA
<213> ORGANISM: Homo sapiens

<400> SEQUENCE: 92
uacccuguag aaccgaauuu gug                                   23

<210> SEQ ID NO 93
<211> LENGTH: 22
<212> TYPE: RNA
<213> ORGANISM: Homo sapiens

<400> SEQUENCE: 93
ucuacagugc acgugucucc ag                                    22

<210> SEQ ID NO 94
<211> LENGTH: 20
<212> TYPE: RNA
<213> ORGANISM: Homo sapiens

<400> SEQUENCE: 94
ccucugggcc cuuccuccag                                       20

<210> SEQ ID NO 95
<211> LENGTH: 23
<212> TYPE: RNA
<213> ORGANISM: Homo sapiens

<400> SEQUENCE: 95
agcucggucu gaggccccuc agu                                   23

```
<210> SEQ ID NO 96
<211> LENGTH: 22
<212> TYPE: RNA
<213> ORGANISM: Homo sapiens

<400> SEQUENCE: 96
ucgugucuug uguugcagcc gg                                              22

<210> SEQ ID NO 97
<211> LENGTH: 22
<212> TYPE: RNA
<213> ORGANISM: Homo sapiens

<400> SEQUENCE: 97
ucggauccgu cugagcuugg cu                                              22

<210> SEQ ID NO 98
<211> LENGTH: 22
<212> TYPE: RNA
<213> ORGANISM: Mus musculus

<400> SEQUENCE: 98
ucucugggcc ugugucuuag gc                                              22

<210> SEQ ID NO 99
<211> LENGTH: 22
<212> TYPE: RNA
<213> ORGANISM: Mus musculus

<400> SEQUENCE: 99
uguaaacauc cuacacucag cu                                              22

<210> SEQ ID NO 100
<211> LENGTH: 22
<212> TYPE: RNA
<213> ORGANISM: Mus musculus

<400> SEQUENCE: 100
aggcaagaug cuggcauagc ug                                              22

<210> SEQ ID NO 101
<211> LENGTH: 22
<212> TYPE: RNA
<213> ORGANISM: Mus musculus

<400> SEQUENCE: 101
cugcccuggc ccgagggacc ga                                              22

<210> SEQ ID NO 102
<211> LENGTH: 22
<212> TYPE: RNA
<213> ORGANISM: Mus musculus

<400> SEQUENCE: 102
aacccguaga uccgaucuug ug                                              22

<210> SEQ ID NO 103
<211> LENGTH: 23
<212> TYPE: RNA
<213> ORGANISM: Mus musculus

<400> SEQUENCE: 103
ucuggcuccg ugucuucacu ccc                                             23
```

```
<210> SEQ ID NO 104
<211> LENGTH: 21
<212> TYPE: RNA
<213> ORGANISM: Mus musculus

<400> SEQUENCE: 104
ucagugcaug acagaacuug g                                               21

<210> SEQ ID NO 105
<211> LENGTH: 22
<212> TYPE: RNA
<213> ORGANISM: Mus musculus

<400> SEQUENCE: 105
aacacaccug uucaaggauu ca                                              22

<210> SEQ ID NO 106
<211> LENGTH: 22
<212> TYPE: RNA
<213> ORGANISM: Mus musculus

<400> SEQUENCE: 106
cuccugacuc cagguccugu gu                                              22

<210> SEQ ID NO 107
<211> LENGTH: 22
<212> TYPE: RNA
<213> ORGANISM: Mus musculus

<400> SEQUENCE: 107
cagugcaaug uuaaaagggc au                                              22

<210> SEQ ID NO 108
<211> LENGTH: 22
<212> TYPE: RNA
<213> ORGANISM: Mus musculus

<400> SEQUENCE: 108
cuuucagucg gauguuugca gc                                              22

<210> SEQ ID NO 109
<211> LENGTH: 23
<212> TYPE: RNA
<213> ORGANISM: Mus musculus

<400> SEQUENCE: 109
uagcaccauu ugaaaucagu guu                                             23

<210> SEQ ID NO 110
<211> LENGTH: 22
<212> TYPE: RNA
<213> ORGANISM: Mus musculus

<400> SEQUENCE: 110
cuuucagucg gauguuuaca gc                                              22

<210> SEQ ID NO 111
<211> LENGTH: 22
<212> TYPE: RNA
<213> ORGANISM: Mus musculus

<400> SEQUENCE: 111
uauugcacau uacuaaguug ca                                              22
```

```
<210> SEQ ID NO 112
<211> LENGTH: 22
<212> TYPE: RNA
<213> ORGANISM: Mus musculus

<400> SEQUENCE: 112
cuauacaauc uauugccuuc cc                                              22

<210> SEQ ID NO 113
<211> LENGTH: 21
<212> TYPE: RNA
<213> ORGANISM: Mus musculus

<400> SEQUENCE: 113
gccccugggc cuauccuaga a                                               21

<210> SEQ ID NO 114
<211> LENGTH: 22
<212> TYPE: RNA
<213> ORGANISM: Mus musculus

<400> SEQUENCE: 114
aguucuucag uggcaagcuu ua                                              22

<210> SEQ ID NO 115
<211> LENGTH: 23
<212> TYPE: RNA
<213> ORGANISM: Mus musculus

<400> SEQUENCE: 115
aggaagcccu ggaggggcug gag                                             23

<210> SEQ ID NO 116
<211> LENGTH: 22
<212> TYPE: RNA
<213> ORGANISM: Mus musculus

<400> SEQUENCE: 116
uguaacagca acuccaugug ga                                              22

<210> SEQ ID NO 117
<211> LENGTH: 22
<212> TYPE: RNA
<213> ORGANISM: Mus musculus

<400> SEQUENCE: 117
uagcaccauu ugaaaucggu ua                                              22

<210> SEQ ID NO 118
<211> LENGTH: 22
<212> TYPE: RNA
<213> ORGANISM: Mus musculus

<400> SEQUENCE: 118
acgcccuucc ccccuucuu ca                                               22

<210> SEQ ID NO 119
<211> LENGTH: 21
<212> TYPE: RNA
<213> ORGANISM: Mus musculus

<400> SEQUENCE: 119
ccguccugag guuguugagc u                                               21
```

```
<210> SEQ ID NO 120
<211> LENGTH: 22
<212> TYPE: RNA
<213> ORGANISM: Mus musculus

<400> SEQUENCE: 120
cguuugccac uaaccucaac cu                                             22

<210> SEQ ID NO 121
<211> LENGTH: 21
<212> TYPE: RNA
<213> ORGANISM: Mus musculus

<400> SEQUENCE: 121
cuauacaguc uacugucuuu c                                              21

<210> SEQ ID NO 122
<211> LENGTH: 22
<212> TYPE: RNA
<213> ORGANISM: Mus musculus

<400> SEQUENCE: 122
acucuacaac cuuaggacuu gc                                             22

<210> SEQ ID NO 123
<211> LENGTH: 22
<212> TYPE: RNA
<213> ORGANISM: Mus musculus

<400> SEQUENCE: 123
cugccaauuc cauaggucac ag                                             22

<210> SEQ ID NO 124
<211> LENGTH: 22
<212> TYPE: RNA
<213> ORGANISM: Mus musculus

<400> SEQUENCE: 124
acccgucccg uucgucccg ga                                              22

<210> SEQ ID NO 125
<211> LENGTH: 23
<212> TYPE: RNA
<213> ORGANISM: Mus musculus

<400> SEQUENCE: 125
ugcuaugcca acauauugcc auc                                            23

<210> SEQ ID NO 126
<211> LENGTH: 21
<212> TYPE: RNA
<213> ORGANISM: Mus musculus

<400> SEQUENCE: 126
uccgguucuc agggcuccac c                                              21

<210> SEQ ID NO 127
<211> LENGTH: 22
<212> TYPE: RNA
<213> ORGANISM: Mus musculus

<400> SEQUENCE: 127
cuuucaguca gauguuugcu gc                                             22
```

```
<210> SEQ ID NO 128
<211> LENGTH: 22
<212> TYPE: RNA
<213> ORGANISM: Mus musculus

<400> SEQUENCE: 128
uaugugccuu uggacuacau cg                                              22

<210> SEQ ID NO 129
<211> LENGTH: 22
<212> TYPE: RNA
<213> ORGANISM: Mus musculus

<400> SEQUENCE: 129
ccuguucucc auuacuuggc uc                                              22

<210> SEQ ID NO 130
<211> LENGTH: 21
<212> TYPE: RNA
<213> ORGANISM: Mus musculus

<400> SEQUENCE: 130
cucccacaug caggguuugc a                                               21

<210> SEQ ID NO 131
<211> LENGTH: 22
<212> TYPE: RNA
<213> ORGANISM: Mus musculus

<400> SEQUENCE: 131
aacuggccua caaaguccca gu                                              22

<210> SEQ ID NO 132
<211> LENGTH: 21
<212> TYPE: RNA
<213> ORGANISM: Mus musculus

<400> SEQUENCE: 132
gcaguccacg ggcauauaca c                                               21

<210> SEQ ID NO 133
<211> LENGTH: 22
<212> TYPE: RNA
<213> ORGANISM: Mus musculus

<400> SEQUENCE: 133
acuguacagg ccacugccuu gc                                              22

<210> SEQ ID NO 134
<211> LENGTH: 22
<212> TYPE: RNA
<213> ORGANISM: Mus musculus

<400> SEQUENCE: 134
aaaguucuga gacacuccga cu                                              22

<210> SEQ ID NO 135
<211> LENGTH: 23
<212> TYPE: RNA
<213> ORGANISM: Homo sapiens

<400> SEQUENCE: 135
acuccauuug uuuugaugau gga                                             23
```

```
<210> SEQ ID NO 136
<211> LENGTH: 22
<212> TYPE: RNA
<213> ORGANISM: Homo sapiens

<400> SEQUENCE: 136
uguaaacauc cucgacugga ag                                              22

<210> SEQ ID NO 137
<211> LENGTH: 22
<212> TYPE: RNA
<213> ORGANISM: Homo sapiens

<400> SEQUENCE: 137
acuggacuug gagucagaag gc                                              22

<210> SEQ ID NO 138
<211> LENGTH: 19
<212> TYPE: RNA
<213> ORGANISM: Homo sapiens

<400> SEQUENCE: 138
aucccaccac ugccaccau                                                  19

<210> SEQ ID NO 139
<211> LENGTH: 22
<212> TYPE: RNA
<213> ORGANISM: Homo sapiens

<400> SEQUENCE: 139
uaaugccccu aaaaauccuu au                                              22

<210> SEQ ID NO 140
<211> LENGTH: 21
<212> TYPE: RNA
<213> ORGANISM: Homo sapiens

<400> SEQUENCE: 140
augaccuaug aauugacaga c                                               21

<210> SEQ ID NO 141
<211> LENGTH: 22
<212> TYPE: RNA
<213> ORGANISM: Homo sapiens

<400> SEQUENCE: 141
ugagguagua guuugugcug uu                                              22

<210> SEQ ID NO 142
<211> LENGTH: 21
<212> TYPE: RNA
<213> ORGANISM: Homo sapiens

<400> SEQUENCE: 142
agcuacaucu ggcuacuggg u                                               21

<210> SEQ ID NO 143
<211> LENGTH: 22
<212> TYPE: RNA
<213> ORGANISM: Homo sapiens

<400> SEQUENCE: 143
uaaugccccu aaaaauccuu au                                              22
```

```
<210> SEQ ID NO 144
<211> LENGTH: 22
<212> TYPE: RNA
<213> ORGANISM: Homo sapiens

<400> SEQUENCE: 144
cgucaacacu ugcugguuuc cu                                              22

<210> SEQ ID NO 145
<211> LENGTH: 22
<212> TYPE: RNA
<213> ORGANISM: Homo sapiens

<400> SEQUENCE: 145
uccauuacac uacccugccu cu                                              22

<210> SEQ ID NO 146
<211> LENGTH: 23
<212> TYPE: RNA
<213> ORGANISM: Homo sapiens

<400> SEQUENCE: 146
agcagcauug uacagggcua uca                                             23

<210> SEQ ID NO 147
<211> LENGTH: 22
<212> TYPE: RNA
<213> ORGANISM: Homo sapiens

<400> SEQUENCE: 147
aacccguaga uccgaacuug ug                                              22

<210> SEQ ID NO 148
<211> LENGTH: 23
<212> TYPE: RNA
<213> ORGANISM: Homo sapiens

<400> SEQUENCE: 148
uuaaugcuaa ucgugauagg ggu                                             23

<210> SEQ ID NO 149
<211> LENGTH: 22
<212> TYPE: RNA
<213> ORGANISM: Homo sapiens

<400> SEQUENCE: 149
cugcccuggc ccgagggacc ga                                              22
```